United States Patent
Beckmann et al.

(10) Patent No.: US 11,732,036 B2
(45) Date of Patent: Aug. 22, 2023

(54) ANTIBODY THAT BINDS TO VEGF-A AND ANG2 AND METHODS OF USE

(71) Applicant: Hoffmann-La Roche Inc., Little Falls, NJ (US)

(72) Inventors: Roland Beckmann, Penzberg (DE); Sebastian Fenn, Penzberg (DE); Guido Hartmann, Basel (CH); Sabine Imhof-Jung, Penzberg (DE); Kristian Hobolt-Jensen, Penzberg (DE); Joerg Moelleken, Penzberg (DE); Michael Molhoj, Penzberg (DE); Christian Schantz, Penzberg (DE); Janina Speck, Penzberg (DE); Christoph Ullmer, Basel (CH); Barbara Weiser, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 17/466,276

(22) Filed: Sep. 3, 2021

(65) Prior Publication Data

US 2022/0073599 A1 Mar. 10, 2022

(30) Foreign Application Priority Data

Sep. 4, 2020 (EP) .................... 20194610
Nov. 24, 2020 (EP) .................... 20209591

(51) Int. Cl.
*C07K 16/22* (2006.01)
*A61K 9/00* (2006.01)
*A61P 27/02* (2006.01)

(52) U.S. Cl.
CPC ............. *C07K 16/22* (2013.01); *A61P 27/02* (2018.01); *A61K 9/0019* (2013.01); *C07K 2317/31* (2013.01); *C07K 2317/33* (2013.01); *C07K 2317/55* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

2020/0102381 A1 4/2020 Lu et al.
2020/0199214 A1 6/2020 Beckmann et al.

FOREIGN PATENT DOCUMENTS

| KR | 10-2015-0063847 | | 6/2015 |
|---|---|---|---|
| WO | 2008/027236 A2 | | 3/2008 |
| WO | 2008/027236 A3 | | 3/2008 |
| WO | 2010/108127 A1 | | 9/2010 |
| WO | 2012/163520 A1 | | 12/2012 |
| WO | 2014/009465 A1 | | 1/2014 |
| WO | 2015/107015 A1 | | 7/2015 |
| WO | 2016/122996 A1 | | 8/2016 |
| WO | 2018/037000 A1 | | 3/2018 |
| WO | 2019/154776 A1 | | 8/2019 |
| WO | 2019/200006 A2 | | 10/2019 |
| WO | 2020/089051 A1 | | 5/2020 |
| WO | WO 2022/049165 | * | 3/2022 |

OTHER PUBLICATIONS

Bostrom, J., et al., "Variants of the Antibody Herceptin That Interact with HER2 and VEGF at the Antigen Binding Site" Science 323(5921):1610-1614 (Mar. 20, 2009).
"International Search Report—PCT/EP2021/074195" (w/Written Opinion),:pp. 1-14 (dated Nov. 25, 2021).
Kabat, E.A., et al. Sequences of Proteins of Immunological Interest: Tabulation and Analysis of Amino Acid and Nucleic Acid Sequences of Precursors, V-Regions, C-Regions, J-Chain T-Cell Receptors for Antigen, T-Cell Surface Antigens, β-2 Microglobulins, Major Histocompatibility Antigens, Thy-1, Complement, C-Reactive Protein, Thymopoietin, Integrins, Post-gamma Globulin, α2-Macroglobulins, and Other Related Proteins (NIH Publication No. 91-3242), Fifth edition, Bethesda, MD-US:: Table of Contents (1991).
Sharma, A., et al., "Faricimab: exppanding horizon beyond VEGF" EYE (London) 34(5):802-804 (May 1, 2020).

* cited by examiner

*Primary Examiner* — Marianne P Allen
(74) *Attorney, Agent, or Firm* — Grant Kalinowski

(57) ABSTRACT

The present invention relates to anti-VEGF-A/anti-ANG2 antibodies, e.g. in the form of a bispecific Fab fragment, and methods of using the same.

9 Claims, 10 Drawing Sheets

Specification includes a Sequence Listing.

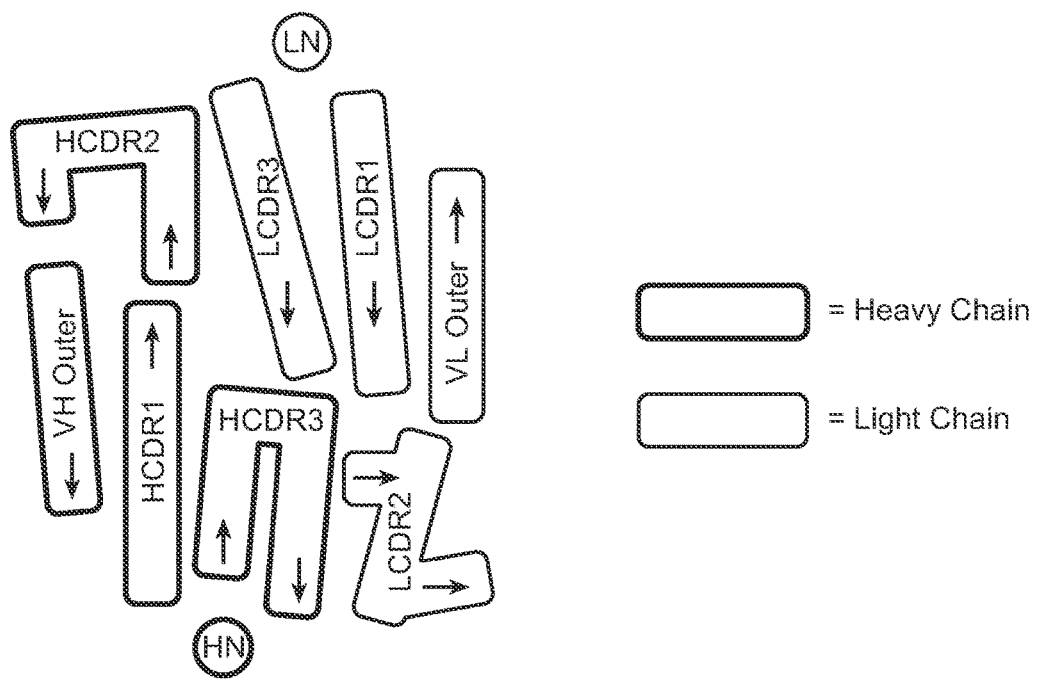
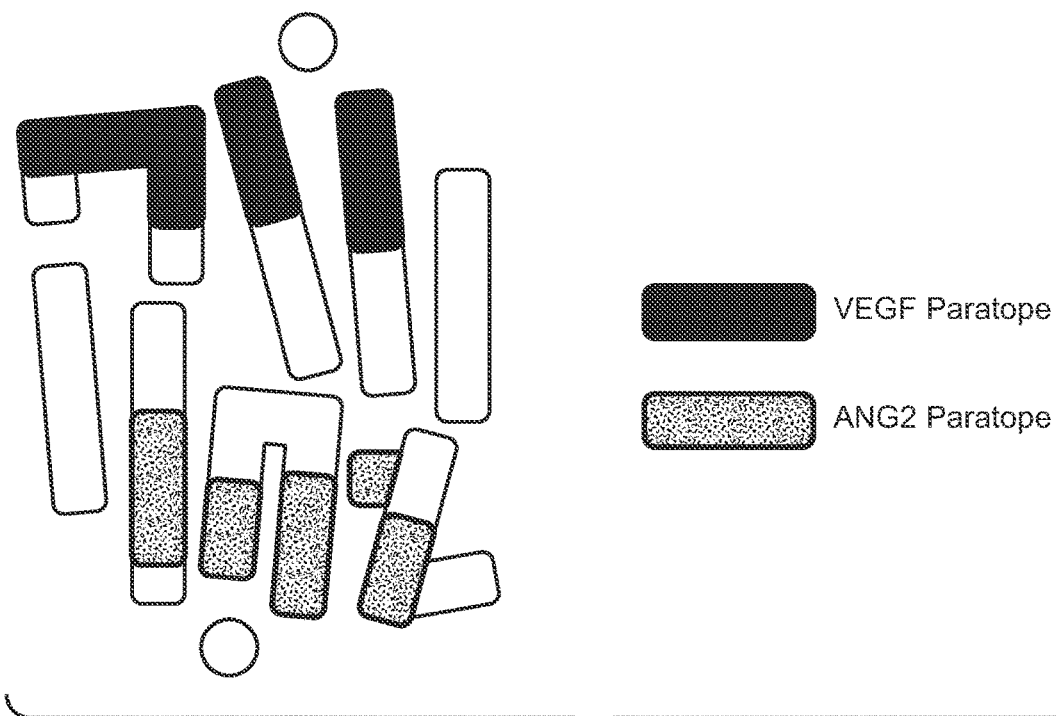
FIG. 1

Positions 1–52:

| Kabat VL | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 27a | 27b | 27c | 27d | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
|  | FR1 |   |   |   |   |   |   |   |   |   |   |   |   |   |   |   |   |   |   |   |   |   |   | LCDR1 |   |   |   |   |   |   |   |   |   |   |   |   |   |   | FR2 |   |   |   |   |   |   |   |   |   |   |   |   |   |   | LCDR2 |   |   |
| P1AA8906 | A | I | Y | M | H | Q | E | P | S | S | L | S | A | S | V | G | D | R | V | T | I | T | C | H | G | S | Y | W | L | S | N | Y | L | A | W | Y | Q | Q | K | P | G | K | A | P | K | L | L | I | F | D | A | R |
| P1AA0902 | A | I | Y | M | H | Q | E | P | S | S | L | S | A | S | V | G | D | R | V | T | I | T | C | H | G | S | Y | W | L | N | S | E | L | A | W | Y | Q | Q | K | P | G | K | A | P | K | L | L | I | F | D | G | D |
| P1AD9820 | A | I | Y | M | H | Q | E | P | S | S | L | S | A | S | V | G | D | R | V | T | I | T | C | H | G | S | Y | W | L | N | S | E | V | A | W | Y | Q | Q | K | P | G | K | A | P | K | L | L | I | F | D | G | D |
| ANG2 par. |   |   |   |   |   |   |   |   |   |   |   |   |   |   |   |   |   |   |   |   |   |   |   |   |   |   |   |   |   |   |   |   |   |   |   |   |   |   |   |   |   |   |   |   |   |   |   |   |   |   |   |   |
| VEGF par. |   |   | ■ |   |   |   |   |   |   |   |   |   |   |   |   |   |   |   |   |   |   |   |   |   |   |   | ■ |   |   |   |   |   | ■ |   |   |   |   |   |   |   |   |   |   |   |   |   |   |   | ■ |   |   |   |

Positions 53–104:

| Kabat VL | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
|  | LCDR2 |   |   |   |   | | | | | | | | | | | | | | | FR3 | | | | | | | | | | | | | | | | | LCDR3 | | | | | | | | | FR4 | | | | | |
| P1AA8906 | W | L | F | K | V | P | S | R | F | S | G | S | G | S | G | H | E | D | Y | T | L | T | I | S | S | L | Q | P | E | D | F | A | T | Y | Y | C | Q | Q | Y | R | Y | H | P | Y | T | F | G | H | G | T | K | V |
| P1AA0902 | W | L | F | K | V | P | S | R | F | S | G | S | G | S | G | H | E | D | Y | T | L | T | I | S | S | L | Q | P | E | D | F | A | T | Y | Y | C | Q | Q | Y | R | Y | H | P | Y | T | F | G | H | G | T | K | V |
| P1AD9820 | W | L | F | K | V | P | S | R | F | S | G | S | G | S | G | H | E | D | Y | T | L | T | I | S | S | L | Q | P | E | D | F | A | T | Y | Y | C | Q | Q | Y | R | Y | H | P | Y | T | F | G | H | G | T | K | V |
| ANG2 par. |   |   | ■ | ■ |   |   |   |   |   |   |   |   |   |   |   |   |   |   |   |   |   |   |   |   |   |   |   |   |   |   |   |   |   |   |   |   |   |   |   |   |   |   |   |   |   |   |   |   |   |   |   |   |
| VEGF par. |   |   |   |   |   |   |   |   |   |   |   |   |   |   |   |   |   |   |   |   |   |   |   |   |   |   |   |   |   |   |   |   |   |   |   |   |   |   |   |   |   |   | ■ |   |   |   |   |   |   |   |   |   |

Positions 105–107:

| Kabat VL | 105 | 106 | 107/106A |
|---|---|---|---|
|  | FR4 |   |   |
| P1AA8906 | E | I | K |
| P1AA0902 | E | I | K |
| P1AD9820 | E | I | K |
| ANG2 par. |   |   |   |
| VEGF par. |   |   |   |

SEQUENCE LISTING

<160> NUMBER OF SEQ ID NOS: 30

<210> SEQ ID NO 1
<211> LENGTH: 115
<212> TYPE: PRT
<213> ORGANISM: Artificial Sequence

```
<220> FEATURE:
<223> OTHER INFORMATION: VH domain of P1AA8906

<400> SEQUENCE: 1

Asp Phe Gln Leu Val Glu Ser Gly Gly Gly Leu Val Lys Pro Gly Gly
1               5                   10                  15

Ser Leu Arg Leu Ser Cys Ala Ala Ser Tyr Glu Phe Glu Tyr Asp Asp
            20                  25                  30

Met Ser Trp Val Arg Gln Ala Pro Gly Lys Gly Leu Glu Trp Val Gly
        35                  40                  45

Ser Ile Ser Pro Lys Gly Gly Ser Thr Tyr Tyr Asn Thr Lys Phe Ile
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Val Gly Phe Phe Asp Met Trp Gly Gln Gly Thr Leu Val Thr
            100                 105                 110

Val Ser Ser
        115

<210> SEQ ID NO 2
<211> LENGTH: 107
<212> TYPE: PRT
<213> ORGANISM: Artificial Sequence
<220> FEATURE:
<223> OTHER INFORMATION: VL domain of P1AA8906

<400> SEQUENCE: 2

Ala Ile Tyr Met His Gln Glu Pro Ser Ser Leu Ser Ala Ser Val Gly
1               5                   10                  15

Asp Arg Val Thr Ile Thr Cys His Gly Ser Tyr Trp Leu Ser Asn Tyr
            20                  25                  30

Leu Ala Trp Tyr Gln Gln Lys Pro Gly Lys Ala Pro Lys Leu Leu Ile
        35                  40                  45

Phe Asp Ala Arg Trp Leu Val His Gly Val Pro Ser Arg Phe Ser Gly
    50                  55                  60

Ser Gly Ser His Glu Asp Tyr Thr Leu Thr Ile Ser Ser Leu Gln Pro
65                  70                  75                  80

Glu Asp Phe Ala Thr Tyr Tyr Cys Gln Gln Tyr Arg Tyr His Pro Tyr
                85                  90                  95

Thr Phe Gly His Gly Thr Lys Val Glu Ile Lys
            100                 105

<210> SEQ ID NO 3
<211> LENGTH: 4
<212> TYPE: PRT
<213> ORGANISM: Artificial Sequence
<220> FEATURE:
<223> OTHER INFORMATION: H-CDR1 of P1AA8906, P1AA0902 and P1AD9820

<400> SEQUENCE: 3

Asp Asp Met Ser
1

<210> SEQ ID NO 4
<211> LENGTH: 17
<212> TYPE: PRT
<213> ORGANISM: Artificial Sequence
```

```
<220> FEATURE:
<223> OTHER INFORMATION: H-CDR2 of P1AA8906

<400> SEQUENCE: 4

Ser Ile Ser Pro Lys Gly Gly Ser Thr Tyr Tyr Asn Thr Lys Phe Ile
1               5                   10                  15
Gly

<210> SEQ ID NO 5
<211> LENGTH: 7
<212> TYPE: PRT
<213> ORGANISM: Artificial Sequence
<220> FEATURE:
<223> OTHER INFORMATION: H-CDR3 of P1AA8906

<400> SEQUENCE: 5

Asp Val Gly Phe Phe Asp Met
1               5

<210> SEQ ID NO 6
<211> LENGTH: 11
<212> TYPE: PRT
<213> ORGANISM: Artificial Sequence
<220> FEATURE:
<223> OTHER INFORMATION: L-CDR1 of P1AA8906

<400> SEQUENCE: 6

His Gly Ser Tyr Trp Leu Ser Asn Tyr Leu Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: L-CDR2 of P1AA8906

<400> SEQUENCE: 7

Asp Ala Arg Trp Leu Val His
1               5

<210> SEQ ID NO 8
<211> LENGTH: 9
<212> TYPE: PRT
<213> ORGANISM: Artificial Sequence
<220> FEATURE:
<223> OTHER INFORMATION: L-CDR3 of P1AA8906, P1AA0902 and P1AD9820

<400> SEQUENCE: 8

Gln Gln Tyr Arg Tyr His Pro Tyr Thr
1               5

<210> SEQ ID NO 9
<211> LENGTH: 223
<212> TYPE: PRT
<213> ORGANISM: Artificial Sequence
<220> FEATURE:
<223> OTHER INFORMATION: heavy chain of P1AA8906 Fab fragment

<400> SEQUENCE: 9

Asp Phe Gln Leu Val Glu Ser Gly Gly Gly Leu Val Lys Pro Gly Gly
1               5                   10                  15

Ser Leu Arg Leu Ser Cys Ala Ala Ser Tyr Glu Phe Glu Tyr Asp Asp
            20                  25                  30
```

```
Met Ser Trp Val Arg Gln Ala Pro Gly Lys Gly Leu Glu Trp Val Gly
             35                  40                  45

Ser Ile Ser Pro Lys Gly Ser Thr Tyr Tyr Asn Thr Lys Phe Ile
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Asp Val Gly Phe Phe Asp Met Trp Gly Gln Gly Thr Leu Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Lys Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr
        210                 215                 220

<210> SEQ ID NO 10
<211> LENGTH: 214
<212> TYPE: PRT
<213> ORGANISM: Artificial Sequence
<220> FEATURE:
<223> OTHER INFORMATION: light chain of P1AA8906 Fab fragment

<400> SEQUENCE: 10

Ala Ile Tyr Met His Gln Glu Pro Ser Ser Leu Ser Ala Ser Val Gly
 1               5                  10                  15

Asp Arg Val Thr Ile Thr Cys His Gly Ser Tyr Trp Leu Ser Asn Tyr
                 20                  25                  30

Leu Ala Trp Tyr Gln Gln Lys Pro Gly Lys Ala Pro Lys Leu Leu Ile
             35                  40                  45

Phe Asp Ala Arg Trp Leu Val His Gly Val Pro Ser Arg Phe Ser Gly
 50                  55                  60

Ser Gly Ser His Glu Asp Tyr Thr Leu Thr Ile Ser Ser Leu Gln Pro
65                   70                  75                  80

Glu Asp Phe Ala Thr Tyr Tyr Cys Gln Gln Tyr Arg Tyr His Pro Tyr
                 85                  90                  95

Thr Phe Gly His Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
    210

<210> SEQ ID NO 11
<211> LENGTH: 115
<212> TYPE: PRT
<213> ORGANISM: Artificial Sequence
<220> FEATURE:
<223> OTHER INFORMATION: VH domain of P1AA0902

<400> SEQUENCE: 11

Asp Asp His Leu Val Glu Ser Gly Gly Leu Val Lys Pro Gly Gly
1               5                   10                  15

Ser Leu Arg Leu Ser Cys Ala Thr Ala Asp Phe Phe Glu Tyr Asp Asp
            20                  25                  30

Met Ser Trp Val Arg Gln Ala Pro Gly Lys Gly Leu Glu Trp Val Gly
        35                  40                  45

Ser Ile Ser Gly Arg Gly Asp His Lys Tyr Leu Asn Thr Lys Phe Ile
    50                  55                  60

Gly Arg Phe Thr Ile Ser Arg Asp Asp Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Val Gly Phe Phe Asp Trp Trp Gly Gln Gly Thr Leu Val Thr
            100                 105                 110

Val Ser Ser
        115

<210> SEQ ID NO 12
<211> LENGTH: 107
<212> TYPE: PRT
<213> ORGANISM: Artificial Sequence
<220> FEATURE:
<223> OTHER INFORMATION: VL domain of P1AA0902

<400> SEQUENCE: 12

Ala Ile Tyr Met His Gln Glu Pro Ser Ser Leu Ser Ala Ser Val Gly
1               5                   10                  15

Asp Arg Val Thr Ile Thr Cys His Gly Ser Tyr Trp Leu Asn Ser Glu
            20                  25                  30

Leu Ala Trp Tyr Gln Gln Lys Pro Gly Lys Ala Pro Lys Leu Leu Ile
        35                  40                  45

Phe Asp Gly Asp Phe Lys Val Phe Asp Val Pro Ser Arg Phe Ser Gly
    50                  55                  60

Ser Gly Ser His Glu Asp Tyr Thr Leu Thr Ile Ser Ser Leu Gln Pro
65                  70                  75                  80

Glu Asp Phe Ala Thr Tyr Tyr Cys Gln Gln Tyr Arg Tyr His Pro Tyr
                85                  90                  95

Thr Phe Gly His Gly Thr Lys Val Glu Ile Lys
            100                 105

<210> SEQ ID NO 13
<211> LENGTH: 17
<212> TYPE: PRT
<213> ORGANISM: Artificial Sequence
```

```
<220> FEATURE:
<223> OTHER INFORMATION: H-CDR2 of P1AA0902

<400> SEQUENCE: 13

Ser Ile Ser Gly Arg Gly Asp His Lys Tyr Leu Asn Thr Lys Phe Ile
1               5                   10                  15
Gly

<210> SEQ ID NO 14
<211> LENGTH: 7
<212> TYPE: PRT
<213> ORGANISM: Artificial Sequence
<220> FEATURE:
<223> OTHER INFORMATION: H-CDR3 of P1AA0902 and P1AD9820

<400> SEQUENCE: 14

Asp Val Gly Phe Phe Asp Trp
1               5

<210> SEQ ID NO 15
<211> LENGTH: 11
<212> TYPE: PRT
<213> ORGANISM: Artificial Sequence
<220> FEATURE:
<223> OTHER INFORMATION: L-CDR1 of P1AA0902

<400> SEQUENCE: 15

His Gly Ser Tyr Trp Leu Asn Ser Glu Leu Ala
1               5                   10

<210> SEQ ID NO 16
<211> LENGTH: 7
<212> TYPE: PRT
<213> ORGANISM: Artificial Sequence
<220> FEATURE:
<223> OTHER INFORMATION: L-CDR2 of P1AA0902

<400> SEQUENCE: 16

Asp Gly Asp Phe Lys Val Phe
1               5

<210> SEQ ID NO 17
<211> LENGTH: 223
<212> TYPE: PRT
<213> ORGANISM: Artificial Sequence
<220> FEATURE:
<223> OTHER INFORMATION: heavy chain of P1AA0902 Fab fragment

<400> SEQUENCE: 17

Asp Asp His Leu Val Glu Ser Gly Gly Gly Leu Val Lys Pro Gly Gly
1               5                   10                  15

Ser Leu Arg Leu Ser Cys Ala Thr Ala Asp Phe Phe Glu Tyr Asp Asp
                20                  25                  30

Met Ser Trp Val Arg Gln Ala Pro Gly Lys Gly Leu Glu Trp Val Gly
            35                  40                  45

Ser Ile Ser Gly Arg Gly Asp His Lys Tyr Leu Asn Thr Lys Phe Ile
        50                  55                  60

Gly Arg Phe Thr Ile Ser Arg Asp Asp Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Val Gly Phe Phe Asp Trp Gly Gln Gly Thr Leu Val Thr
            100                 105                 110
```

```
Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr
210                 215                 220

<210> SEQ ID NO 18
<211> LENGTH: 214
<212> TYPE: PRT
<213> ORGANISM: Artificial Sequence
<220> FEATURE:
<223> OTHER INFORMATION: light chain of P1AA0902 Fab fragment

<400> SEQUENCE: 18

Ala Ile Tyr Met His Gln Glu Pro Ser Ser Leu Ser Ala Ser Val Gly
1               5                   10                  15

Asp Arg Val Thr Ile Thr Cys His Gly Ser Tyr Trp Leu Asn Ser Glu
            20                  25                  30

Leu Ala Trp Tyr Gln Gln Lys Pro Gly Lys Ala Pro Lys Leu Leu Ile
        35                  40                  45

Phe Asp Gly Asp Phe Lys Val Phe Asp Val Pro Ser Arg Phe Ser Gly
    50                  55                  60

Ser Gly Ser His Glu Asp Tyr Thr Leu Thr Ile Ser Ser Leu Gln Pro
65                  70                  75                  80

Glu Asp Phe Ala Thr Tyr Tyr Cys Gln Gln Tyr Arg Tyr His Pro Tyr
                85                  90                  95

Thr Phe Gly His Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 19
<211> LENGTH: 115
<212> TYPE: PRT
<213> ORGANISM: Artificial Sequence
```

<220> FEATURE:
<223> OTHER INFORMATION: VH domain of P1AD9820

<400> SEQUENCE: 19

Ser Glu His Leu Val Glu Ser Gly Gly Gly Leu Val Lys Pro Gly Gly
1               5                   10                  15

Ser Leu Arg Leu Ser Cys Ala Thr Ala Asp Phe Phe Glu Tyr Asp Asp
            20                  25                  30

Met Ser Trp Val Arg Gln Ala Pro Gly Lys Gly Leu Glu Trp Val Gly
        35                  40                  45

Ser Ile Ser Pro Lys Gly Asp His Lys Tyr Leu Asn Thr Lys Phe Ile
    50                  55                  60

Gly Arg Phe Thr Ile Ser Arg Asp Asp Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Val Gly Phe Phe Asp Trp Trp Gly Gln Gly Thr Leu Val Thr
            100                 105                 110

Val Ser Ser
        115

<210> SEQ ID NO 20
<211> LENGTH: 107
<212> TYPE: PRT
<213> ORGANISM: Artificial Sequence
<220> FEATURE:
<223> OTHER INFORMATION: VL domain of P1AD9820

<400> SEQUENCE: 20

Ala Ile Tyr Met His Gln Glu Pro Ser Ser Leu Ser Ala Ser Val Gly
1               5                   10                  15

Asp Arg Val Thr Ile Thr Cys His Gly Ser Tyr Trp Leu Asn Ser Glu
            20                  25                  30

Val Ala Trp Tyr Gln Gln Lys Pro Gly Lys Ala Pro Lys Leu Leu Ile
        35                  40                  45

Phe Asp Gly Asp Phe Lys Val Tyr Glu Val Pro Ser Arg Phe Ser Gly
    50                  55                  60

Ser Gly Ser His Glu Asp Tyr Thr Leu Thr Ile Ser Ser Leu Gln Pro
65                  70                  75                  80

Glu Asp Phe Ala Thr Tyr Tyr Cys Gln Gln Tyr Arg Tyr His Pro Tyr
                85                  90                  95

Thr Phe Gly His Gly Thr Lys Val Glu Ile Lys
            100                 105

<210> SEQ ID NO 21
<211> LENGTH: 17
<212> TYPE: PRT
<213> ORGANISM: Artificial Sequence
<220> FEATURE:
<223> OTHER INFORMATION: H-CDR2 of P1AD9820

<400> SEQUENCE: 21

Ser Ile Ser Pro Lys Gly Asp His Lys Tyr Leu Asn Thr Lys Phe Ile
1               5                   10                  15

Gly

```
<210> SEQ ID NO 22
<211> LENGTH: 11
<212> TYPE: PRT
<213> ORGANISM: Artificial Sequence
<220> FEATURE:
<223> OTHER INFORMATION: L-CDR1 of P1AD9820

<400> SEQUENCE: 22

His Gly Ser Tyr Trp Leu Asn Ser Glu Val Ala
1               5                   10

<210> SEQ ID NO 23
<211> LENGTH: 7
<212> TYPE: PRT
<213> ORGANISM: Artificial Sequence
<220> FEATURE:
<223> OTHER INFORMATION: L-CDR2 of P1AD9820

<400> SEQUENCE: 23

Asp Gly Asp Phe Lys Val Tyr
1               5

<210> SEQ ID NO 24
<211> LENGTH: 223
<212> TYPE: PRT
<213> ORGANISM: Artificial Sequence
<220> FEATURE:
<223> OTHER INFORMATION: heavy chain of P1AD9820 Fab fragment

<400> SEQUENCE: 24

Ser Glu His Leu Val Glu Ser Gly Gly Leu Val Lys Pro Gly Gly
1               5                   10                  15

Ser Leu Arg Leu Ser Cys Ala Thr Ala Asp Phe Phe Glu Tyr Asp Asp
                20                  25                  30

Met Ser Trp Val Arg Gln Ala Pro Gly Lys Gly Leu Glu Trp Val Gly
            35                  40                  45

Ser Ile Ser Pro Lys Gly Asp His Lys Tyr Leu Asn Thr Lys Phe Ile
        50                  55                  60

Gly Arg Phe Thr Ile Ser Arg Asp Asp Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Val Gly Phe Phe Asp Trp Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr
    210                 215                 220
```

<210> SEQ ID NO 25
<211> LENGTH: 214
<212> TYPE: PRT
<213> ORGANISM: Artificial Sequence
<220> FEATURE:
<223> OTHER INFORMATION: light chain of P1AD9820 Fab fragment

<400> SEQUENCE: 25

Ala Ile Tyr Met His Gln Glu Pro Ser Ser Leu Ser Ala Ser Val Gly
1               5                   10                  15

Asp Arg Val Thr Ile Thr Cys His Gly Ser Tyr Trp Leu Asn Ser Glu
            20                  25                  30

Val Ala Trp Tyr Gln Gln Lys Pro Gly Lys Ala Pro Lys Leu Leu Ile
        35                  40                  45

Phe Asp Gly Asp Phe Lys Val Tyr Glu Val Pro Ser Arg Phe Ser Gly
    50                  55                  60

Ser Gly Ser His Glu Asp Tyr Thr Leu Thr Ile Ser Ser Leu Gln Pro
65                  70                  75                  80

Glu Asp Phe Ala Thr Tyr Tyr Cys Gln Gln Tyr Arg Tyr His Pro Tyr
                85                  90                  95

Thr Phe Gly His Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 26
<211> LENGTH: 232
<212> TYPE: PRT
<213> ORGANISM: Homo sapiens

<400> SEQUENCE: 26

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

```
Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Lys Lys Ser Val
        130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys
            180                 185                 190

His Leu Phe Val Gln Asp Pro Gln Thr Cys Lys Cys Ser Cys Lys Asn
        195                 200                 205

Thr Asp Ser Arg Cys Lys Ala Arg Gln Leu Glu Leu Asn Glu Arg Thr
    210                 215                 220

Cys Arg Cys Asp Lys Pro Arg Arg
225                 230
```

<210> SEQ ID NO 27
<211> LENGTH: 496
<212> TYPE: PRT
<213> ORGANISM: Homo sapiens

<400> SEQUENCE: 27

```
Met Trp Gln Ile Val Phe Phe Thr Leu Ser Cys Asp Leu Val Leu Ala
1               5                   10                  15

Ala Ala Tyr Asn Asn Phe Arg Lys Ser Met Asp Ser Ile Gly Lys Lys
            20                  25                  30

Gln Tyr Gln Val Gln His Gly Ser Cys Ser Tyr Thr Phe Leu Leu Pro
        35                  40                  45

Glu Met Asp Asn Cys Arg Ser Ser Ser Ser Pro Tyr Val Ser Asn Ala
    50                  55                  60

Val Gln Arg Asp Ala Pro Leu Glu Tyr Asp Asp Ser Val Gln Arg Leu
65                  70                  75                  80

Gln Val Leu Glu Asn Ile Met Glu Asn Asn Thr Gln Trp Leu Met Lys
                85                  90                  95

Leu Glu Asn Tyr Ile Gln Asp Asn Met Lys Lys Glu Met Val Glu Ile
            100                 105                 110

Gln Gln Asn Ala Val Gln Asn Gln Thr Ala Val Met Ile Glu Ile Gly
        115                 120                 125

Thr Asn Leu Leu Asn Gln Thr Ala Glu Gln Thr Arg Lys Leu Thr Asp
    130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
            180                 185                 190

Lys Lys Val Leu Ala Met Glu Asp Lys His Ile Ile Gln Leu Gln Ser
        195                 200                 205

Ile Lys Glu Glu Lys Asp Gln Leu Gln Val Leu Val Ser Lys Gln Asn
    210                 215                 220

Ser Ile Ile Glu Glu Leu Glu Lys Lys Ile Val Thr Ala Thr Val Asn
225                 230                 235                 240

Asn Ser Val Leu Gln Lys Gln Gln His Asp Leu Met Glu Thr Val Asn
                245                 250                 255
```

```
Asn Leu Leu Thr Met Met Ser Thr Ser Asn Ser Ala Lys Asp Pro Thr
            260                 265                 270

Val Ala Lys Glu Glu Gln Ile Ser Phe Arg Asp Cys Ala Glu Val Phe
        275                 280                 285

Lys Ser Gly His Thr Thr Asn Gly Ile Tyr Thr Leu Thr Phe Pro Asn
    290                 295                 300

Ser Thr Glu Glu Ile Lys Ala Tyr Cys Asp Met Glu Ala Gly Gly Gly
305                 310                 315                 320

Gly Trp Thr Ile Ile Gln Arg Arg Glu Asp Gly Ser Val Asp Phe Gln
                325                 330                 335

Arg Thr Trp Lys Glu Tyr Lys Val Gly Phe Gly Asn Pro Ser Gly Glu
            340                 345                 350

Tyr Trp Leu Gly Asn Glu Phe Val Ser Gln Leu Thr Asn Gln Gln Arg
        355                 360                 365

Tyr Val Leu Lys Ile His Leu Lys Asp Trp Glu Gly Asn Glu Ala Tyr
    370                 375                 380

Ser Leu Tyr Glu His Phe Tyr Leu Ser Ser Glu Glu Leu Asn Tyr Arg
385                 390                 395                 400

Ile His Leu Lys Gly Leu Thr Gly Thr Ala Gly Lys Ile Ser Ser Ile
                405                 410                 415

Ser Gln Pro Gly Asn Asp Phe Ser Thr Lys Asp Gly Asp Asn Asp Lys
            420                 425                 430

Cys Ile Cys Lys Cys Ser Gln Met Leu Thr Gly Gly Trp Trp Phe Asp
        435                 440                 445

Ala Cys Gly Pro Ser Asn Leu Asn Gly Met Tyr Tyr Pro Gln Arg Gln
    450                 455                 460

Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
                485                 490                 495

<210> SEQ ID NO 28
<211> LENGTH: 147
<212> TYPE: PRT
<213> ORGANISM: Homo sapiens

<400> SEQUENCE: 28

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125
```

Glu Cys Arg Pro Lys Lys Asp Arg Ala Arg Gln Glu Lys Cys Asp Lys
        130                 135                 140
Pro Arg Arg
145

<210> SEQ ID NO 29
<211> LENGTH: 213
<212> TYPE: PRT
<213> ORGANISM: Artificial Sequence
<220> FEATURE:
<223> OTHER INFORMATION: Nesvacumab Mab LC

<400> SEQUENCE: 29

Ile Val Leu Thr Gln Ser Pro Gly Thr Leu Ser Leu Ser Pro Gly Glu
1               5                   10                  15

Arg Ala Thr Leu Ser Cys Arg Ala Ser Gln Ser Val Ser Ser Thr Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln His Tyr Asp Asn Ser Gln Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 30
<211> LENGTH: 452
<212> TYPE: PRT
<213> ORGANISM: Artificial Sequence
<220> FEATURE:
<223> OTHER INFORMATION: Nesvacumab Mab HC

<400> SEQUENCE: 30

Ala Val Gln Leu Val Ala Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Ile His Trp Val Arg Gln Ala Thr Gly Lys Gly Leu Glu Trp Val
        35                  40                  45

```
Ser Ala Ile Gly Pro Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
 65                  70                  75                  80

Gln Met Asn Ser Leu Arg Ala Gly Asp Thr Ala Val Tyr Tyr Cys Ala
                 85                  90                  95

Arg Gly Leu Ile Thr Phe Gly Gly Leu Ile Ala Pro Phe Asp Tyr Trp
                100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
    275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Gly Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
    355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
    435                 440                 445

Ser Pro Gly Lys
    450
```

ANTIBODY THAT BINDS TO VEGF-A AND ANG2 AND METHODS OF USE

CROSS REFERENCE TO RELATED APPLICATIONS

This application claims priority to European Application No. 20194610.0 filed Sep. 4, 2020 and European Application No. 20209591.5, filed Nov. 24, 2020, which are incorporated herein by reference in their entirety.

SEQUENCE LISTING

This application contains a Sequence Listing which has been submitted electronically in ASCII format and is hereby incorporated by reference in its entirety. Said ASCII copy, created on Aug. 18, 2021, is named Sequence_Listing.txt and is 34,879 bytes in size.

FIELD OF THE INVENTION

The present invention relates to anti-VEGF-A/anti-ANG2 antibodies and methods of using the same.

BACKGROUND OF THE INVENTION

Bispecific antibodies binding to VEGF and ANG2 have been reported previously and have been suggested for therapy of ocular vascular diseases like age related macular degeneration. Faricimab (INN), a full length IgG1 antibody comprising a Fab binding arm specifically binding to VEGF and a second Fab binding arm specifically binding to ANG2, is the most advanced bispecific therapeutic being currently evaluated in clinical phase III studies for treatment of DME and nAMD (Sharma, A., Kumar, N., Kuppermann, B. D. et al. Eye 34, 802-804 (2020)).

Further combination treatments targeting VEGF and ANG2 for treatment of ocular vascular diseases have been suggested in the last years (e.g. WO2016/122996 A1, WO2018/037000A1, WO2019/200006A2, US 2020/0102381 A1).

Multispecific antibodies comprising two paratopes in one pair of a variable heavy chain domain (VH) and a variable light chain domain (VL) have been described in WO2008/027236; WO2010/108127 and Bostrom, J., et al., Science 323 (2009) 1610-1614 as well as in WO2012/163520.

WO2012/163520 discloses bispecific antibodies comprising two paratopes in one pair of VH and VL domains ("DutaFabs"). Each paratope of the bispecific antibody of WO2012/163520 comprises amino acids from the heavy chain and from the light chain CDRs, wherein heavy chain CDR-H1 and CDR-H3 as well as light chain CDR-L2 contribute to the first paratope and light chain CDR-L1 and CDR-L3 as well as heavy chain CDR-H2 contribute to the second paratope Monospecific antibodies comprising the individual paratopes are isolated independently from different Fab-libraries, which are diversified in either the first or the second paratope. The amino acid sequences of said monospecific antibodies are identified and merged into the biparatopic VH and VL pair. One exemplary Fab fragment specifically binding to VEGF and IL-6 is disclosed in WO2012/163520.

Yet there is a need for improved therapeutic antibodies that bind to VEGF and ANG2, e.g. by improving efficacy vs. standard-of-care and by improving duration of action and in turn, reducing frequency of intravitral injections, leading to less administration burden for the patient.

SUMMARY OF THE INVENTION

The present invention relates to bispecific anti-VEGF-A/anti-ANG2 antibodies and methods of using the same.

In one aspect the invention provides an antibody that binds to human VEGF-A and to human ANG2, comprising a VEGF-A paratope and an ANG2 paratope within one cognate pair of a variable light chain domain (VL domain) and a variable heavy chain domain (VH domain), wherein the VEGF-A paratope comprises amino acid residues from CDR-H2, CDR-L1 and CDR-L3 of the antibody, wherein the ANG2 paratope comprises amino acid residues from the CDR-H1, CDR-H3 and CDR-L2 of the antibody.

In one aspect the invention provides an antibody that binds to human VEGF-A and to human ANG2, comprising a VEGF-A paratope and an ANG2 paratope within one cognate pair of a variable light chain domain (VL domain) and a variable heavy chain domain (VH domain), wherein the pair of the variable light chain domain and the variable heavy chain domain simultaneously binds to human VEGF-A and human ANG2.

In one aspect the invention provides an antibody that binds to human VEGF-A and to human ANG2, comprising a VEGF-A paratope and an ANG2 paratope within one cognate pair of a variable light chain domain (VL domain) and a variable heavy chain domain (VH domain), wherein the antibody binds to the same epitope on human VEGF-A and to the same epitope on human ANG2 as an antibody with a variable heavy chain domain of SEQ ID NO: 19 and a variable light chain domain of SEQ ID NO: 20.

In one aspect the invention provides an antibody that binds to human VEGF-A and to human ANG2, wherein an antibody Fab fragment of the antibody binds (i) to human VEGF-A121 with a $K_D$ of less than 50 pM as measured by KinExA®, and (ii) to human ANG2 with a $K_D$ of less than 50 pM as measured by KinExA®.

In one aspect the invention provides an antibody that binds to human VEGF-A and to human ANG2, wherein an antibody Fab fragment of the antibody exhibits an aggregation onset temperature of 70° C. or more as measured by static light scattering (SLS), in one embodiment as measured by SLS as described in the chapter "Thermal stability" in the Materials & general methods section.

In one aspect the invention provides an antibody that binds to human VEGF-A and to human ANG2, wherein an antibody Fab fragment of the antibody exhibits a melting temperature of more than 80° C. as measured by static light scattering (SLS), in one embodiment as measured by SLS as described in the chapter "Thermal stability" in the Materials & general methods section.

In one aspect the invention provides an antibody that binds to human VEGF-A and to human ANG2, wherein a 20 mM His/HisHCl, pH 6.0 solution comprising 180 mg/ml of the antibody Fab fragment has a viscosity of less than 20 cP at 20° C. as detected by dynamic light scattering with a latex-bead DLS method as described in Example 8.

In one aspect the invention provides an antibody that binds to human VEGF-A and to human ANG2, wherein the antibody comprises a VH domain comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, and a VL domain comprising (d) CDR-L1 comprising the amino acid sequence of SEQ ID NO:22, (e) CDR-L2 comprising the amino acid sequence of SEQ ID NO:23, and (f) CDR-L3 comprising the amino acid sequence of SEQ ID NO:8.

In one aspect the invention provides an antibody that binds to human VEGF-A and to human ANG2, wherein the amino acid sequence of SEQ ID NO:21, and (c) CDR-H3 comprising the amino acid sequence of SEQ ID NO:14, (d) a human heavy chain framework with (i) FR1 comprising amino acid residues H3, D26, F27, E29, and Y30, (ii) FR3 comprising amino acid residues R66 and R94; and a VL domain comprising (e) CDR-L1 comprising the amino acid sequence of SEQ ID NO:22, (f) CDR-L2 comprising the amino acid sequence of SEQ ID NO:23, (g) CDR-L3 comprising the amino acid sequence of SEQ ID NO:8, and (h) a human light chain framework with (i) FR1 comprising amino acid residues 12 and Y3, (ii) FR2 comprising amino acid residues L46 and F49, (iii) FR3 comprising amino acid residue E57, wherein the numbering of the VH and VL domains is according to the Kabat numbering system.

In one aspect the invention provides an antibody that binds to human VEGF-A and to human ANG2 comprising a VH domain comprising amino acid residues H3, D26, F27, E29, Y30, D35b, D35c, D55, H56, K57, Y58, T61, K62, F63, 164, G65, R66, R94, D95, V96, F98, and F99, and a VL domain comprising amino acid residues I2, Y3, Y27, W27a, E32, L46, F49, D50, F53, K54, V55, Y56, E57, Y91, R92, Y93, H94, and P95, wherein the numbering of the VH and VL domains is according to the Kabat numbering system. In one embodiment the antibody comprises a VEGF-A paratope comprising the following amino acid residues in the VH domain D35c, D55, H56, K57, Y58, T61, K62, F63, 164, G65, R66, and D95, and the following amino acid residues in the VL domain I2, Y3, Y27, W27a, E32, R92, Y93, H94, and P95; and an ANG2 paratope comprising the following amino acid residues in the VH domain H3, D26, F27, E29, Y30, D35b, R94, V96, F98, and F99, and the following amino acid residues in the VL domain E32, L46, F49, D50, F53, K54, V55, Y56, E57, and Y91.

In one aspect the invention provides an antibody that binds to human VEGF-A and to human ANG2 comprising (a) a VH domain comprising an amino acid sequence having at least 90% sequence identity to the amino acid sequence of SEQ ID NO:19; and (b) a VL domain comprising an amino acid sequence having at least 90% sequence identity to the amino acid sequence of SEQ ID NO:20.

In one aspect the invention provides an antibody that binds to human VEGF-A and to human ANG2 comprising a VH domain comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, and a VL domain comprising (d) CDR-L1 comprising the amino acid sequence of SEQ ID NO:22, (e) CDR-L2 comprising the amino acid sequence of SEQ ID NO:23, and (f) CDR-L3 comprising the amino acid sequence of SEQ ID NO:8, comprising (a) a VH domain comprising an amino acid sequence having at least 90% sequence identity to the amino acid sequence of SEQ ID NO:19; and (b) a VL domain comprising an amino acid sequence having at least 90% sequence identity to the amino acid sequence of SEQ ID NO:20.

In one aspect the invention provides an antibody that binds to human VEGF-A and to human ANG2 comprising a VH domain comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, and a VL domain comprising (d) CDR-L1 comprising the amino acid sequence of SEQ ID NO:22, (e) CDR-L2 comprising the amino acid sequence of SEQ ID NO:23, and (f) CDR-L3 comprising the amino acid sequence of SEQ ID NO:8, comprising (a) a VH domain comprising an amino acid sequence having at least 90% sequence identity to the amino acid sequence of SEQ ID NO:19, wherein the VH domain comprises amino acid residues H3, D26, F27, E29, Y30, R66 and R94; and (b) a VL domain comprising an amino acid sequence having at least 90% sequence identity to the amino acid sequence of SEQ ID NO:20, wherein the VL domain comprises amino acid residues I2, Y3, L46, F49, and E57, wherein the numbering of the VH and VL domains is according to the Kabat numbering system.

In one aspect the invention provides an antibody that binds to human VEGF-A and to human ANG2 comprising a VH domain comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, (d) a human heavy chain framework with (i) FR1 comprising amino acid residues H3, D26, F27, E29, and Y30, (ii) FR3 comprising amino acid residues R66 and R94; and a VL domain comprising (e) CDR-L1 comprising the amino acid sequence of SEQ ID NO:22, (f) CDR-L2 comprising the amino acid sequence of SEQ ID NO:23, (g) CDR-L3 comprising the amino acid sequence of SEQ ID NO:8, and (h) a human light chain framework with (i) FR1 comprising amino acid residues 12 and Y3, (ii) FR2 comprising amino acid residues L46 and F49, (iii) FR3 comprising amino acid residue E57, wherein the numbering of the VH and VL domains is according to the Kabat numbering system, comprising (a) a VH domain comprising an amino acid sequence having at least 90% sequence identity to the amino acid sequence of SEQ ID NO:19; and (b) a VL domain comprising an amino acid sequence having at least 90% sequence identity to the amino acid sequence of SEQ ID NO:20.

In one aspect the invention provides an antibody that binds to human VEGF-A and to human ANG2 comprising (a) a VH domain comprising an amino acid sequence of SEQ ID NO:19 with up to 15 amino acid substitutions, wherein the amino acid substitutions are located at one or more pf positions 1, 2, 4 to 25, 28, 35d to 54, 59, 60, 67 to 93, 97, 101 to 113 of SEQ ID NO:19; and (b) a variable light chain domain comprising an amino acid sequence of SEQ ID NO:20 with up to 15 amino acid substitutions, wherein the amino acid substitutions are located at positions 1, 4 to 26, 27b to 27d, 33 to 45, 47, 48, 51, 52, 58 to 90, 96 to 107 of SEQ ID NO:20, wherein the numbering of the VH and VL domains is according to the Kabat numbering system.

In one aspect the invention provides an antibody that binds to human VEGF-A and to human ANG2 comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, and a VL domain (d) CDR-L1 comprising the amino acid sequence of SEQ ID NO:22, (e) CDR-L2 comprising the amino acid sequence of SEQ ID NO:23, and (f) CDR-L3 comprising the amino acid sequence of SEQ ID NO:8, comprising (a) a VH domain comprising an amino acid sequence of SEQ ID NO:19 with up to 15 amino acid substitutions; and (b) a variable light chain domain comprising an amino acid sequence of SEQ ID NO:20 with up to 15 amino acid substitutions.

In one aspect the invention provides an antibody that binds to human VEGF-A and to human ANG2 comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, (d) a human heavy chain framework with (i) FR1 comprising amino acid residues H3, D26, F27, E29, and Y30, (ii) FR3 comprising amino acid residues R66 and R94; and a VL domain comprising (e) CDR-L1 comprising the amino acid sequence of SEQ ID NO:22, (f) CDR-L2 comprising the amino acid sequence of SEQ ID NO:23, (g) CDR-L3 comprising the amino acid sequence of SEQ ID NO:8, and (h) a human light chain framework with (i) FR1 comprising amino acid residues 12 and Y3, (ii) FR2 comprising amino acid residues L46 and F49, (iii) FR3 comprising amino acid residue E57, wherein the numbering of the VH and VL domains is according to the Kabat numbering system, and comprising (a) a VH domain comprising an amino acid sequence of SEQ ID NO:19 with up to 15 amino acid substitutions; and (b) a variable light chain domain comprising an amino acid sequence of SEQ ID NO:20 with up to 15 amino acid substitutions.

In one aspect the invention provides an antibody that binds to human VEGF-A and to human ANG2 comprising a VH sequence of SEQ ID NO:19 and a VL sequence of SEQ ID NO:20.

In one aspect the invention provides an antibody that binds to human VEGF-A and to human ANG2 comprising a heavy chain amino acid sequence of SEQ ID NO:24 and a light chain amino acid sequence of SEQ ID NO:25.

In one aspect the invention provides an antibody that binds to human VEGF-A and to human ANG2 comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, and a VL domain comprising (d) CDR-L1 comprising the amino acid sequence of SEQ ID NO:22, (e) CDR-L2 comprising the amino acid sequence of SEQ ID NO:23, and (f) CDR-L3 comprising the amino acid sequence of SEQ ID NO:8, wherein an antibody Fab fragment of the antibody binds (i) to human VEGF-A121 with a $K_D$ of less than 50 pM as measured by KinExA®, and (ii) to human ANG2 with a $K_D$ of less than 50 pM as measured by KinExA®.

In one aspect the invention provides an antibody that binds to human VEGF-A and to human ANG2 comprising a VH domain comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, (d) a human heavy chain framework with (i) FR1 comprising amino acid residues H3, D26, F27, E29, and Y30, (ii) FR3 comprising amino acid residues R66 and R94; and a VL domain comprising (e) CDR-L1 comprising the amino acid sequence of SEQ ID NO:22, (f) CDR-L2 comprising the amino acid sequence of SEQ ID NO:23, (g) CDR-L3 comprising the amino acid sequence of SEQ ID NO:8, and (h) a human light chain framework with (i) FR1 comprising amino acid residues 12 and Y3, (ii) FR2 comprising amino acid residues L46 and F49, (iii) FR3 comprising amino acid residue E57, wherein the numbering of the VH and VL domains is according to the Kabat numbering system, wherein the antibody comprises (a) a VH domain comprising an amino acid sequence having at least 90% sequence identity to the amino acid sequence of SEQ ID NO:19; and (b) a VL domain comprising an amino acid sequence having at least 90% sequence identity to the amino acid sequence of SEQ ID NO:20; and wherein an antibody Fab fragment of the antibody binds (i) to human VEGF-A121 with a $K_D$ of less than 50 pM as measured by KinExA®, and (ii) to human ANG2 with a $K_D$ of less than 50 pM as measured by KinExA®.

In one aspect the invention provides an antibody that binds to human VEGF-A and to human ANG2 comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, and a VL domain comprising (d) CDR-L1 comprising the amino acid sequence of SEQ ID NO:22, (e) CDR-L2 comprising the amino acid sequence of SEQ ID NO:23, and (f) CDR-L3 comprising the amino acid sequence of SEQ ID NO:8, wherein an antibody Fab fragment of the antibody exhibits an aggregation onset temperature of 70° C. or more.

In one aspect the invention provides an antibody that binds to human VEGF-A and to human ANG2 comprising a VH domain comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, (d) a human heavy chain framework with (i) FR1 comprising amino acid residues H3, D26, F27, E29, and Y30, (ii) FR3 comprising amino acid residues R66 and R94; and a VL domain comprising (e) CDR-L1 comprising the amino acid sequence of SEQ ID NO:22, (f) CDR-L2 comprising the amino acid sequence of SEQ ID NO:23, (g) CDR-L3 comprising the amino acid sequence of SEQ ID NO:8, and (h) a human light chain framework with (i) FR1 comprising amino acid residues 12 and Y3, (ii) FR2 comprising amino acid residues L46 and F49, (iii) FR3 comprising amino acid residue E57, wherein the numbering of the VH and VL domains is according to the Kabat numbering system, wherein the antibody comprises (a) a VH domain comprising an amino acid sequence having at least 90% sequence identity to the amino acid sequence of SEQ ID NO:19; and (b) a VL domain comprising an amino acid sequence having at least 90% sequence identity to the amino acid sequence of SEQ ID NO:20; and wherein an antibody Fab fragment of the antibody exhibits an aggregation onset temperature of 70° C. or more.

In one aspect the invention provides an antibody that binds to human VEGF-A and to human ANG2 comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, and a VL domain comprising (d) CDR-L1 comprising the amino acid sequence of SEQ ID NO:22, (e) CDR-L2 comprising the amino acid sequence of SEQ ID NO:23, and (f) CDR-L3 comprising the amino acid sequence of SEQ ID NO:8, wherein an antibody Fab fragment of the antibody exhibits a melting temperature of more than 80° C. as measured by dynamic light scattering.

In one aspect the invention provides an antibody that binds to human VEGF-A and to human ANG2 comprising a VH domain comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, (d) a human heavy chain framework with (i) FR1 comprising amino acid residues H3, D26, F27, E29, and Y30, (ii) FR3 comprising amino acid residues R66 and R94; and a VL domain comprising (e) CDR-L1 comprising the amino acid sequence of SEQ ID NO:22, (f) CDR-L2 comprising the amino acid sequence of SEQ ID NO:23, (g) CDR-L3 comprising the amino acid sequence of SEQ ID NO:8, and (h) a human light chain framework with (i) FR1 comprising amino acid residues 12 and Y3, (ii) FR2 comprising amino acid residues L46 and F49, (iii) FR3 comprising amino acid residue E57, wherein the numbering of the VH and VL domains is according to the Kabat numbering system, wherein the antibody comprises (a) a VH domain comprising an amino acid sequence having at least 90% sequence identity to the amino acid sequence of SEQ ID NO:19; and (b) a VL domain comprising an amino acid sequence having at least 90% sequence identity to the amino acid sequence of SEQ ID NO:20; and an antibody Fab fragment of the antibody exhibits a melting temperature of more than 80° C. as measured by dynamic light scattering.

In one aspect the invention provides an antibody that binds to human VEGF-A and to human ANG2 comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, and a VL domain comprising (d) CDR-L1 comprising the amino acid sequence of SEQ ID NO:22, (e) CDR-L2 comprising the amino acid sequence of SEQ ID NO:23, and (f) CDR-L3 comprising the amino acid sequence of SEQ ID NO:8, wherein a 20 mM His/HisHCl, pH 6.0 solution comprising 180 mg/ml of the antibody Fab fragment has a viscosity of less than 20 cP at 20° C. as detected by dynamic light scattering with a latex-bead DLS method as described in Example 8.

In one aspect the invention provides an antibody that binds to human VEGF-A and to human ANG2 comprising a VH domain comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, (d) a human heavy chain framework with (i) FR1 comprising amino acid residues H3, D26, F27, E29, and Y30, (ii) FR3 comprising amino acid residues R66 and R94; and a VL domain comprising (e) CDR-L1 comprising the amino acid sequence of SEQ ID NO:22, (f) CDR-L2 comprising the amino acid sequence of SEQ ID NO:23, (g) CDR-L3 comprising the amino acid sequence of SEQ ID NO:8, and (h) a human light chain framework with (i) FR1 comprising amino acid residues 12 and Y3, (ii) FR2 comprising amino acid residues L46 and F49, (iii) FR3 comprising amino acid residue E57, wherein the numbering of the VH and VL domains is according to the Kabat numbering system, wherein the antibody comprises (a) a VH domain comprising an amino acid sequence having at least 90% sequence identity to the amino acid sequence of SEQ ID NO:19; and (b) a VL domain comprising an amino acid sequence having at least 90% sequence identity to the amino acid sequence of SEQ ID NO:20; and wherein a 20 mM His/HisHCl, pH 6.0 solution comprising 180 mg/ml of the antibody Fab fragment has a viscosity of less than 20 cP at 20° C. as detected by dynamic light scattering with a latex-bead DLS method as described in Example 8.

One embodiment of the invention relates to an antibody fragment that binds to human VEGF-A and to human ANG2. One embodiment of the invention relates to a bispecific antibody fragment that binds to human VEGF-A and to human ANG2. In one embodiment the antibody fragment is selected from Fv, Fab, Fab', Fab'-SH, F(ab')$_2$ or single chain antibodies derived therefrom. One embodiment of the invention relates to a Fab fragment that binds to human VEGF-A and to human ANG2. One embodiment of the invention relates to an Fv fragment that binds to human VEGF-A and to human ANG2.

One embodiment of the invention relates to a full length IgG antibody that binds to human VEGF-A and to human ANG2.

In one aspect the invention provides an isolated nucleic acid encoding the antibody of the invention.

In one aspect the invention provides a host cell comprising the nucleic acid of the invention. In one embodiment the host cell is a CHO cell. In one embodiment the host cell is an *E. coli* cell.

In one aspect the invention provides an expression vector comprising the nucleic acid of the invention.

In one aspect the invention provides a method of producing an antibody that binds to human VEGF-A and to human ANG2 comprising culturing the host cell of the invention so that the antibody is produced.

In one aspect the invention provides the antibody produced by the method of the invention.

In one aspect the invention provides a pharmaceutical formulation comprising the antibody of the invention and a pharmaceutically acceptable carrier.

In one aspect the invention provides a pre-filled syringe comprising the antibody of the invention and a pharmaceutically acceptable carrier.

In one aspect the invention provides an ocular implant comprising the antibody of the invention and a pharmaceutically acceptable carrier. In one embodiment, the invention comprises a port delivery device comprising the antibody of the invention.

In one aspect of the invention the antibody or the pharmaceutical formulation is administered by a port delivery device.

In one aspect the invention provides the antibody of the invention for use as a medicament, in one embodiment for use in the treatment of a vascular disease.

In one aspect the invention provides the use of the antibody of the invention or the pharmaceutical composition of the invention in the manufacture of a medicament, in one embodiment a medicament for the treatment of a vascular disease.

In one aspect the invention provides a method of treating an individual having a vascular disease comprising administering to the individual an effective amount of the antibody of the invention or the pharmaceutical composition of the invention.

In one aspect the invention provides a method of inhibiting angiogenesis in an individual comprising administering to the individual an effective amount of the antibody of the invention or the pharmaceutical composition of the invention to inhibit angiogenesis According to the invention a therapeutic anti-VEGF-A/anti-ANG2 antibody is provided that is capable of binding to its target antigens independently, even when it is provided in the form of an antibody Fab fragment. The antibody of the invention is suitable for the treatment of ocular vascular diseases. The antibody of the invention provides several valuable properties that allow its therapeutic application, like high affinities to both targets supporting a low efficacious dose, and a high stability advantageous for long duration. Compared to non-antibody approaches the antibody of the invention tends to be more acceptable due to its high humanness and lack of artificial domains and linkers. Also, the antibody of the invention is advantageous to be provided in high concentrations liquid formulations with a viscosity suitable for ocular application. Due to being providable in high concentrations, treatment with an antibody of the invention is more acceptable for a patient as a higher dose of the therapeutic can be applied at one treatment allowing for a longer treatment cycle. Furthermore, When used as a bispecific Fab fragment for therapy the antibody of the invention allows more binding sites per dose when compared to a bispecific full length IgG antibody.

DESCRIPTION OF THE FIGURES

FIG. 1: Schematic illustration of the Fab fragment of an anti-VEGF-A/anti-ANG2 antibody of the invention. Shown is a top down view of a cognate VH/VL pair including the arrangement of CDR amino acid (upper image). VH domain is indicated in grey, VL domain is indicated in white. Furthermore, the spatial arrangement of the CDR regions is indicated. Paratope regions of an antibody of the invention is highlighted (lower image), with the VEGF-A paratope being arranged in the regions of H-CDR2, L-CDR1 and L-CDR2 and the ANG2 paratope being arranged in the regions of H-CDR1, H-CDR3 and L-CDR2.

Figure 2:
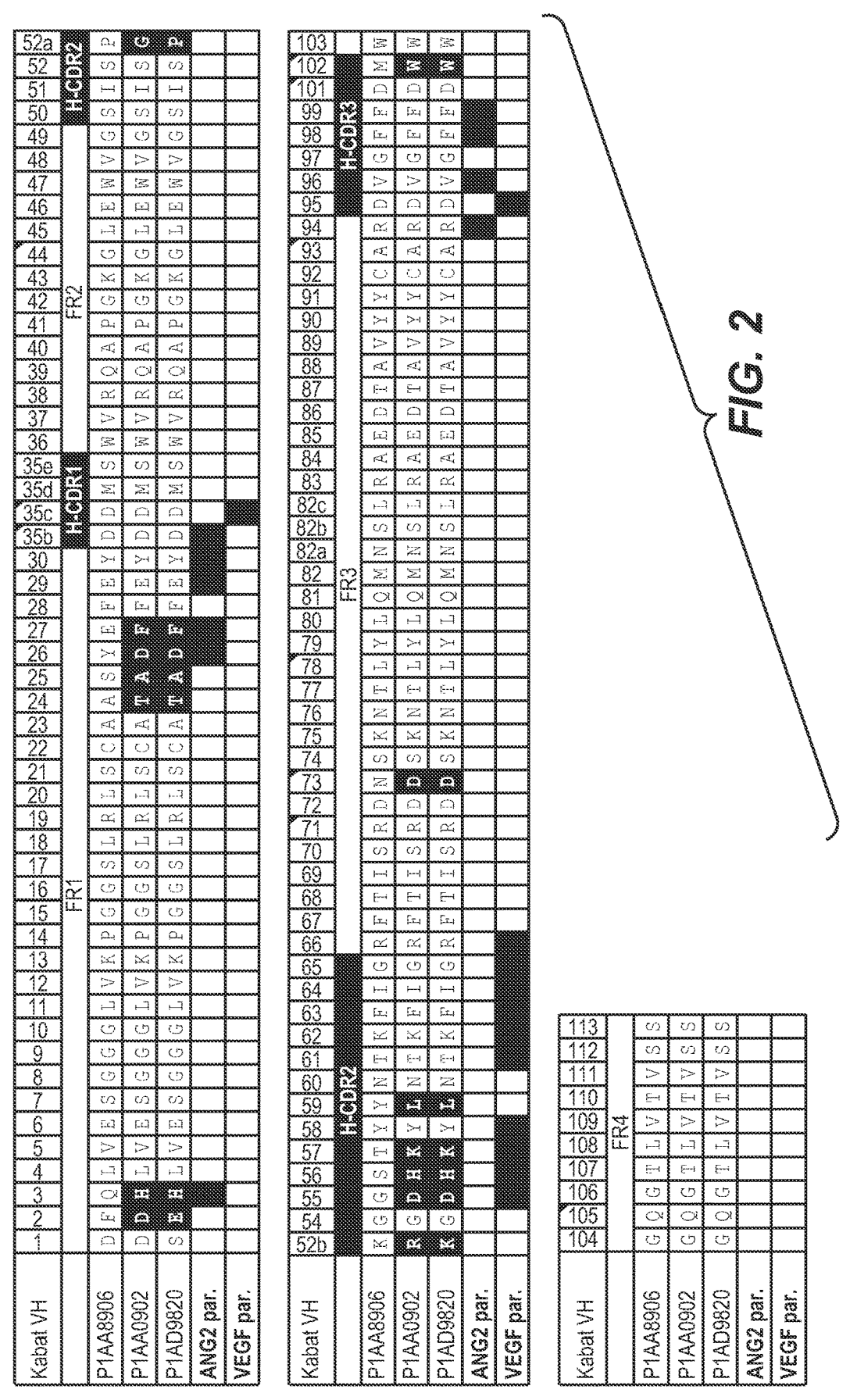

FIG. 2: Amino acid sequences of VH domains of exemplary anti-VEGF-A/anti-ANG2 antibodies of the invention. Kabat numbering of the amino acid position is indicated, as well as the CDR and FR regions. Amino acid positions contributing to the VEGF-A paratope, as well as the ANG2 paratope as identified in Example 13 are highlighted.

FIG. 3: Amino acid sequences of VL domains of exemplary anti-VEGF-A/anti-ANG2 antibodies of the invention. Kabat numbering of the amino acid position is indicated, as well as the CDR and FR regions. Amino acid positions contributing to the VEGF-A paratope, as well as the ANG2 paratope as identified in Example 13 are highlighted.

DETAILED DESCRIPTION OF THE INVENTION

1. Definitions

Figure 4:
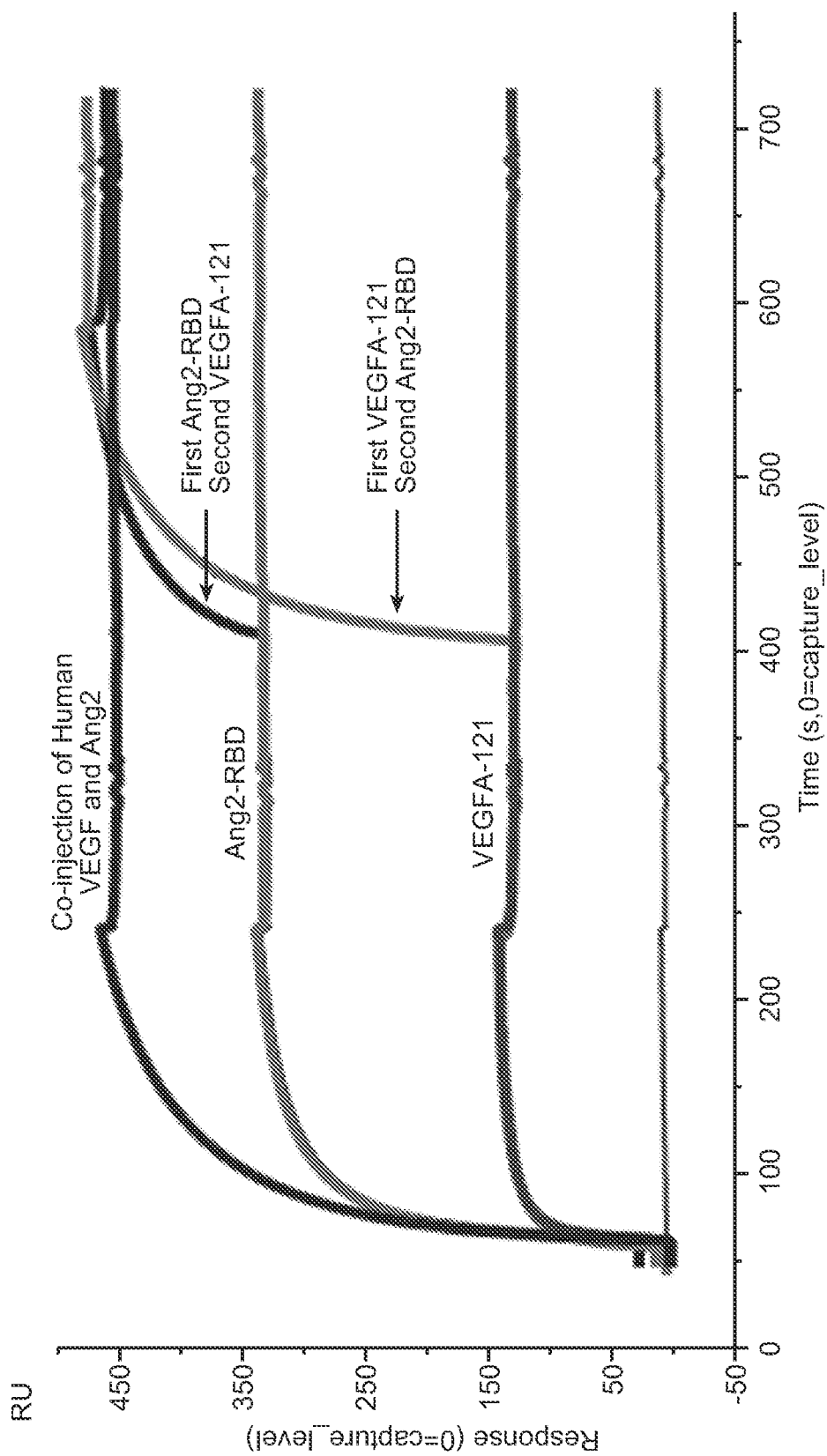
FIG. 4: Independent antigen binding of bispecific antibody P1AD9820 to VEGF-A and ANG2 as assessed via SPR according to Example 5.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The methods and techniques of the present disclosure are generally performed according to conventional methods well known in the art. Generally, nomenclatures used in connection with, and techniques of biochemistry, enzymology, molecular, and cellular biology, microbiology, genetics and protein and nucleic acid chemistry and hybridization described herein are those well-known and commonly used in the art.

Unless otherwise defined herein the term "comprising of" shall include the term "consisting of".

The term "about" as used herein in connection with a specific value (e.g. temperature, concentration, time and others) shall refer to a variation of +/−1% of the specific value that the term "about" refers to.

The term "antibody" herein is used in the broadest sense and encompasses various antibody structures, including but not limited to monoclonal antibodies, multispecific antibodies (e.g., bispecific antibodies), and antibody fragments so long as they exhibit the desired antigen-binding activity.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC) methods. For a review of methods for assessment of antibody purity, see, e.g., Flatman et al., J. Chromatogr. B 848:79-87 (2007).

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method.

The terms "full length antibody", "intact antibody", and "whole antibody" are used herein interchangeably to refer to an antibody having a structure substantially similar to a native antibody structure or having heavy chains that contain an Fc region as defined herein.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. In certain embodiments, the antibody is of the IgG1 isotype. In certain embodiments, the antibody is of the IgG1 isotype with the P329G, L234A and L235A mutation to reduce Fc-region effector function. In other embodiments, the antibody is of the IgG2 isotype. In certain embodiments, the antibody is of the IgG4 isotype with the S228P mutation in the hinge region to improve stability of IgG4 antibody. The heavy chain constant domains that correspond to the different classes of immunoglobulins are called α, δ, ε, γ, and μ, respectively. The light chain of an antibody may be assigned to one of two types, called kappa (κ) and lambda (λ), based on the amino acid sequence of its constant domain.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs) (see, e.g., Kindt et al. Kuby Immunology, 6th ed., W.H. Freeman and Co., page 91 (2007)). In the antibody of the invention, a single pair of a VH domain and a VL domain, i.e. a cognate VH/VL pair, specifically binds to its two targets: VEGF-A and ANG2.

A "DutaFab" is a bispecific antibody as disclosed in WO2012/163520. In a DutaFab a single pair of a VH domain and a VL domain specifically binds to two different epitopes, wherein one paratope comprises amino acid residues from CDR-H2, CDR-L1 and CDR-L3 and the other paratope comprises amino residues from CDR-H1, CDR-H3 and CDR-L2. DutaFabs comprise two non-overlapping paratopes within a cognate VH/VL pair and may simultaneously bind to the two different epitopes. DutaFabs and methods for their generation by screening of libraries comprising monospecific Fab fragments are disclosed in WO2012/163520.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. Antibodies or antibody fragments isolated from human antibody libraries are considered human antibodies or human antibody fragments herein.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

A "paratope" or "antigen binding site", as used interchangeably herein, refers to a part of an antibody which recognizes and binds to an antigen. A paratope is formed by several individual amino acid residues from the antibody's heavy and light chain variable domains arranged that are arranged in spatial proximity in the tertiary structure of the Fv region. The antibodies of the invention comprise two paratopes in one cognate VH/VL pair.

As used herein a "VEGF-A paratope" is a paratope or antigen binding site that binds to VEGF-A. The VEGF-A paratope of an antibody of the invention comprises amino acid residues from CDR-H2, CDR-L1 and CDR-L3 of the antibody.

As used herein an "ANG2 paratope" is a paratope or antigen binding site that binds to ANG2. The ANG2 paratope of an antibody of the invention comprises amino acid residues from CDR-H1, CDR-H3 and CDR-L2 of the antibody.

The term "vascular endothelial growth factor", abbreviated "VEGF", as used herein, refers to any native VEGF from any vertebrate source, including mammals such as primates (e.g. humans) and rodents (e.g., mice and rats), unless otherwise indicated. The term encompasses "full-length", unprocessed VEGF as well as any form of VEGF that results from processing in the cell. The term also encompasses naturally occurring variants of VEGF, e.g., splice variants or allelic variants. The amino acid sequence of an exemplary human VEGF is shown in SEQ ID NO:26.

The terms "anti-VEGF-A antibody" and "an antibody that binds to VEGF-A" refer to an antibody that is capable of binding VEGF-A with sufficient affinity such that the antibody is useful as a diagnostic and/or therapeutic agent in targeting VEGF-A. In one embodiment, the extent of binding of an anti-VEGF-A antibody to an unrelated, non-VEGF-A protein is less than about 10% of the binding of the antibody to VEGF-A as measured, e.g., by surface plasmon resonance (SPR). In certain embodiments, an antibody that binds to VEGF-A has a dissociation constant ($K_D$) of $\leq 1$ nM, $\leq 0.1$ nM, or $\leq 0.01$ nM. An antibody is said to "specifically bind" to VEGF-A when the antibody has a $K_D$ of 1 µM or less.

The term "Angiopoietin-2", abbreviated "ANG2", as used herein, refers to any native ANG2 from any vertebrate source, including mammals such as primates (e.g. humans) and rodents (e.g., mice and rats), unless otherwise indicated. The term encompasses "full-length", unprocessed ANG2 as well as any form of ANG2 that results from processing in the cell. The term also encompasses naturally occurring variants of ANG2, e.g., splice variants or allelic variants. The amino acid sequence of an exemplary human ANG2 is shown in SEQ ID NO:27.

The terms "anti-ANG2 antibody" and "an antibody that binds to anti-ANG2" refer to an antibody that is capable of binding anti-ANG2 with sufficient affinity such that the antibody is useful as a diagnostic and/or therapeutic agent in targeting anti-ANG2. In one embodiment, the extent of binding of an anti-anti-ANG2 antibody to an unrelated, non-anti-ANG2 protein is less than about 10% of the binding of the antibody to anti-ANG2 as measured, e.g., by surface plasmon resonance (SPR). In certain embodiments, an antibody that binds to ANG2 has a dissociation constant ($K_D$) of $\leq 1$ nM, $\leq 0.1$ nM, or $\leq 0.03$ nM. An antibody is said to "specifically bind" to anti-ANG2 when the antibody has a $K_D$ of 1 µM or less.

An antibody of the invention "simultaneously binds to human VEGF-A and human ANG2", which means that (a) an antibody Fab fragment of the invention that is bound to human ANG2 (also) specifically binds to human VEGF-A, and (b) an antibody Fab fragment of the invention that is bound to human VEGF-A (also) specifically binds to human ANG2. Simultaneous binding may be assessed with methods known in the art, e.g. by surface plasmon resonance as described herein.

The term "complementarity determining regions" or "CDRs" as used herein refers to each of the regions of an antibody variable domain which are hypervariable in sequence and contain antigen-contacting residues. Generally, antibodies comprise six CDRs: three in the VH domain (CDR-H1, CDR-H2, CDR-H3), and three in the VL domain (CDR-L1, CDR-L2, CDR-L3). Unless otherwise indicated, CDR residues and other residues in the variable domain (e.g., FR residues) are numbered herein according to the Kabat numbering system (Kabat et al., Sequences of Proteins of Immunological Interest, 5th Ed. Public Health Service, National Institutes of Health, Bethesda, Md., 1991).

"Framework" or "FR" as used herein refers to variable domain amino acid residues other than CDR residues. The framework of a variable domain generally consists of four framework domains: FR1, FR2, FR3, and FR4. Accordingly, the CDR and FR amino acid sequences generally appear in the following sequence in the (a) VH domain: FR1-CDR-H1-FR2-CDR-H2-FR3-CDR-H3-FR4; and (b) in the VL domain: FR1-CDR-L1-FR2-CDR-L2-FR3-CDR-L3-FR4.

According to the Kabat numbering system, as is used herein, framework and CDR regions are located at the following regions of the variable domains:

|    | FR1  | CDR-1   | FR2   | CDR2  | FR3   | CDR3   | FR4     |
|----|------|---------|-------|-------|-------|--------|---------|
| VH | 1-30 | 31-35b* | 36-49 | 50-65 | 66-94 | 95-102 | 103-113 |
| VL | 1-23 | 24-34   | 35-49 | 50-56 | 57-88 | 89-97  | 98-107  |

*in CDR-H1 additional amino acids between position 35b and 36 may be present, herein referred to as positions "35c", "35d" and "35e" as illustrated in FIGS. 2 and 3

The amino acid positions according to the Kabat numbering system referred to herein are illustrated in FIGS. 2 and 3 in an alignment with the amino acid sequences of antibodies of the invention. References to amino acids at a certain position within the amino acid sequence are herein made as well known in the art by stating the respective amino acid and the amino acid position, e.g. "E2" refers to a glutamic acid residue located at Kabat position 2 of the amino acid sequence of the respective antibody domain.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Specific illustrative and exemplary embodiments for measuring binding affinity are described herein.

The term "epitope" denotes the site on an antigen, either proteinaceous or non-proteinaceous, to which an antibody binds. Epitopes can be formed both from contiguous amino acid stretches (linear epitope) or comprise non-contiguous amino acids (conformational epitope), e.g. coming in spatial proximity due to the folding of the antigen, i.e. by the tertiary folding of a proteinaceous antigen. Linear epitopes are typically still bound by an antibody after exposure of the proteinaceous antigen to denaturing agents, whereas conformational epitopes are typically destroyed upon treatment with denaturing agents. An epitope comprises at least 3, at least 4, at least 5, at least 6, at least 7, or 8-10 amino acids in a unique spatial conformation.

Screening for antibodies binding to a particular epitope (i.e., those binding to the same epitope) can be done using methods routine in the art such as, e.g., without limitation, alanine scanning, peptide blots (see Meth. Mol. Biol. 248 (2004) 443-463), peptide cleavage analysis, epitope excision, epitope extraction, chemical modification of antigens (see Prot. Sci. 9 (2000) 487-496), and cross-blocking (see "Antibodies", Harlow and Lane (Cold Spring Harbor Press, Cold Spring Harb., N.Y.).

Antigen Structure-based Antibody Profiling (ASAP), also known as Modification-Assisted Profiling (MAP), allows to bin a multitude of monoclonal antibodies specifically binding to VEGF-A or ANG2 based on the binding profile of each of the antibodies from the multitude to chemically or enzymatically modified antigen surfaces (see, e.g., US 2004/0101920). The antibodies in each bin bind to the same epitope which may be a unique epitope either distinctly different from or partially overlapping with epitope represented by another bin.

Also competitive binding can be used to easily determine whether an antibody binds to the same epitope of VEGF-A or ANG2 as, or competes for binding with, a reference antibody of the invention. For example, an "antibody that binds to the same epitopes on VEGF-A and ANG2" as a reference-antibody refers to an antibody that blocks binding of the reference-antibody to its antigens in respective competition assays by 50% or more, and conversely, the reference antibody blocks binding of the antibody to its antigen in respective competition assays by 50% or more. Also for example, to determine if an antibody binds to the same epitope as a reference-antibody, the reference-antibody is allowed to bind to VEGF-A or ANG2 under saturating conditions. After removal of the excess of the reference-antibody, the ability of an antibody in question to bind to VEGF-A or ANG2 is assessed. If the antibody in question is able to bind to VEGF-A or ANG2 after saturation binding of the reference-antibody, it can be concluded that the antibody in question binds to a different epitope than the reference-antibody. But, if the antibody in question is not able to bind to VEGF-A or ANG2 after saturation binding of the reference-antibody, then the antibody in question may bind to the same epitope as the epitope bound by the reference-antibody. To confirm whether the antibody in question binds to the same epitope or is just hampered from binding by steric reasons routine experimentation can be used (e.g., peptide mutation and binding analyses using ELISA, RIA, surface plasmon resonance, flow cytometry or any other quantitative or qualitative antibody-binding assay available in the art). This assay should be carried out in two set-ups, i.e. with both of the antibodies being the saturating antibody. If, in both set-ups, only the first (saturating) antibody is capable of binding to VEGF-A or ANG2, then it can be concluded that the antibody in question and the reference-antibody compete for binding to VEGF-A or ANG2.

In some embodiments two antibodies are deemed to bind to the same or an overlapping epitope if a 1-, 5-, 10-, 20- or 100-fold excess of one antibody inhibits binding of the other by at least 50%, at least 75%, at least 90% or even 99% or more as measured in a competitive binding assay (see, e.g., Junghans et al., Cancer Res. 50 (1990) 1495-1502).

In some embodiments two antibodies are deemed to bind to the same epitope if essentially all amino acid mutations in the antigen that reduce or eliminate binding of one antibody also reduce or eliminate binding of the other. Two antibodies are deemed to have "overlapping epitopes" if only a subset of the amino acid mutations that reduce or eliminate binding of one antibody reduce or eliminate binding of the other.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity for the purposes of the alignment. Alignment for purposes of determining percent amino acid sequence identity can be achieved in various ways that are within the skill in the art, for instance, using publicly available computer software such as BLAST, BLAST-2, Clustal W, Megalign (DNASTAR) software or the FASTA program package. Those skilled in the art can determine appropriate parameters for aligning sequences, including any algorithms needed to achieve maximal alignment over the full length of the sequences being compared. Alternatively, the percent identity values can be generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087 and is described in WO 2000/005319.

Unless otherwise indicated, for purposes herein, however, % amino acid sequence identity values are generated using the ggsearch program of the FASTA package version 36.3.8c or later with a BLOSUM50 comparison matrix. The FASTA program package was authored by W. R. Pearson and D. J. Lipman (1988), "Improved Tools for Biological Sequence Analysis", PNAS 85:2444-2448; W. R. Pearson (1996) "Effective protein sequence comparison" Meth. Enzymol. 266:227-258; and Pearson et. al. (1997) Genomics 46:24-36 and is publicly available from www.fasta.bioch.virginia.edu/fasta_www2/fasta_down.shtml or www.ebi.ac.uk/Tools/sss/fasta. Alternatively, a public server accessible at fasta.bioch.virginia.edu/fasta_www2/index.cgi can be used to compare the sequences, using the ggsearch (global protein:protein) program and default options (BLOSUM50; open: −10; ext: −2; Ktup=2) to ensure a global, rather than local, alignment is performed. Percent amino acid identity is given in the output alignment header.

An "immunoconjugate" is an antibody conjugated to one or more heterologous molecule(s), including but not limited to a cytotoxic agent.

The term "nucleic acid molecule" or "polynucleotide" includes any compound and/or substance that comprises a polymer of nucleotides. Each nucleotide is composed of a base, specifically a purine- or pyrimidine base (i.e. cytosine (C), guanine (G), adenine (A), thymine (T) or uracil (U)), a sugar (i.e. deoxyribose or ribose), and a phosphate group. Often, the nucleic acid molecule is described by the sequence of bases, whereby said bases represent the primary structure (linear structure) of a nucleic acid molecule. The sequence of bases is typically represented from 5' to 3'. Herein, the term nucleic acid molecule encompasses deoxyribonucleic acid (DNA) including e.g. complementary DNA (cDNA) and genomic DNA, ribonucleic acid (RNA), in particular messenger RNA (mRNA), synthetic forms of DNA or RNA, and mixed polymers comprising two or more of these molecules. The nucleic acid molecule may be linear or circular. In addition, the term nucleic acid molecule includes both, sense and antisense strands, as well as single stranded and double stranded forms. Moreover, the herein described nucleic acid molecule can contain naturally occurring or non-naturally occurring nucleotides. Examples of non-naturally occurring nucleotides include modified nucleotide bases with derivatized sugars or phosphate backbone linkages or chemically modified residues. Nucleic acid molecules also encompass DNA and RNA molecules which are suitable as a vector for direct expression of an antibody of the invention in vitro and/or in vivo, e.g. in a host or patient. Such DNA (e.g. cDNA) or RNA (e.g. mRNA) vectors, can be unmodified or modified. For example, mRNA can be chemically modified to enhance the stability of the RNA vector and/or expression of the encoded molecule so that mRNA can be injected into a subject to generate the antibody in vivo (see e.g. Stadler ert al, Nature Medicine 2017, published online 12 Jun. 2017, doi:10.1038/nm.4356 or EP 2 101 823 BO.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding" an antibody refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

The terms "host cell", "host cell line", and "host cell culture" are used interchangeably and refer to cells into which exogenous nucleic acid has been introduced, including the progeny of such cells. Host cells include "transformants" and "transformed cells", which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "pharmaceutical composition" or "pharmaceutical formulation" refers to a preparation which is in such form as to permit the biological activity of an active ingredient contained therein to be effective, and which contains no additional components which are unacceptably toxic to a subject to which the pharmaceutical composition would be administered.

A "pharmaceutically acceptable carrier" refers to an ingredient in a pharmaceutical composition or formulation, other than an active ingredient, which is nontoxic to a subject. A pharmaceutically acceptable carrier includes, but is not limited to, a buffer, excipient, stabilizer, or preservative.

An "effective amount" of an agent, e.g., a pharmaceutical composition, refers to an amount effective, at dosages and for periods of time necessary, to achieve the desired therapeutic or prophylactic result.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "ocular disease," as used herein, includes any ocular disease associated with pathological angiogenesis and/or atrophy. An ocular disease may be characterized by altered or unregulated proliferation and/or invasion of new blood vessels into the structures of ocular tissues such as the retina or cornea. An ocular disease may be characterized by atrophy of retinal tissue (photoreceptors and the underlying retinal pigment epithelium (RPE) and choriocapillaris). Non-limiting ocular diseases include, for example, AMD (e.g., wet AMD, dry AMD, intermediate AMD, advanced AMD, and geographic atrophy (GA)), macular degeneration, macular edema, DME (e.g., focal, non-center DME and diffuse, center-involved DME), retinopathy, diabetic retinopathy (DR) (e.g., proliferative DR (PDR), non-proliferative DR (NPDR), and high-altitude DR), other ischemia-related retinopathies, ROP, retinal vein occlusion (RVO) (e.g., central (CRVO) and branched (BRVO) forms), CNV (e.g., myopic CNV), corneal neovascularization, diseases associated with corneal neovascularization, retinal neovascularization, diseases associated with retinal/choroidal neovascularization, central serous retinopathy (CSR), pathologic myopia, von Hippel-Lindau disease, histoplasmosis of the eye, FEVR, Coats' disease, Norrie Disease, retinal abnormalities associated with osteoporosis-pseudoglioma syndrome (OPPG), subconjunctival hemorrhage, rubeosis, ocular neovascular disease, neovascular glaucoma, retinitis pigmentosa (RP), hypertensive retinopathy, retinal angiomatous proliferation, macular telangiectasia, iris neovascularization, intraocular neovascularization, retinal degeneration, cystoid macular edema (CME), vasculitis, papilloedema, retinitis, including but not limited to CMV retinitis, ocular melanoma, retinal blastoma, conjunctivitis (e.g., infectious conjunctivitis and non-infectious (e.g, allergic) conjunctivitis), Leber congenital amaurosis (also known as Leber's congenital amaurosis or LCA), uveitis (including infectious and non-infectious uveitis), choroiditis (e.g., multifocal choroiditis), ocular histoplasmosis, blepharitis, dry eye, traumatic eye injury, Sjögren's disease, and other ophthalmic diseases wherein the disease or disease is associated with ocular neovascularization, vascular leakage, and/or retinal edema or retinal atrophy. Additional exemplary ocular diseases include retinoschisis (abnormal splitting of the retina neurosensory layers), diseases associated with rubeosis (neovascularization of the angle) and diseases caused by the abnormal proliferation of fibrovascular or fibrous tissue, including all forms of proliferative vitreoretinopathy. Exemplary diseases associated with corneal neovascularization include, but are not limited to, epidemic keratoconjunctivitis, vitamin A deficiency, contact lens overwear, atopic keratitis, superior limbic keratitis, terygium keratitis sicca, Sjögren's syndrome, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, marginal keratolysis, rheumatoid arthritis, systemic lupus, polyarteritis, trauma, Wegener's sarcoidosis, scleritis, Stevens-Johnson syndrome, periphigoid radial keratotomy, and corneal graph rejection. Exemplary diseases associated with choroidal neovascularization and defects in the retina vasculature, including increased vascular leak, aneurisms and capillary drop-out include, but are not limited to, diabetic retinopathy, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, retina edema (including macular edema), Eales disease, Behcet's disease, infections causing retinitis or choroiditis (e.g., multifocal choroidits), presumed ocular histoplasmosis, Best's disease (vitelliform macular degeneration), myopia, optic pits, pars planitis, retinal detachment (e.g., chronic retinal detachment), hyperviscosity syndromes, toxoplasmosis, trauma, and post-laser complications. Exemplary diseases associated with atrophy of retinal tissues (photoreceptors and the underlying RPE) include, but are not limited to, atrophic or nonexudative AMD (e.g., geographic atrophy or advanced dry AMD), macular atrophy (e.g., atrophy associated with neovascularization and/or geographic atrophy), diabetic retinopathy, Stargardt's disease, Sorsby Fundus Dystrophy, retinoschisis and retinitis pigmentosa.

The term "package insert" is used to refer to instructions customarily included in commercial packages of therapeutic products, that contain information about the indications, usage, dosage, administration, combination therapy, contraindications and/or warnings concerning the use of such therapeutic products.

2. Detailed Description of the Embodiments of the Invention

In one aspect, the invention is based, in part, on the provision of bispecific antibodies for therapeutic application. In certain aspects, antibodies that bind to human VEGF-A and human ANG2 are provided. Antibodies of the invention are useful, e.g., for the diagnosis or treatment of vascular diseases, e.g. ocular vascular diseases.

A. Exemplary Antibodies that Bind to Human VEGF-A and Human ANG2

In one aspect, the invention provides antibodies that bind to human VEGF-A and human ANG2. In one aspect, provided are isolated antibodies that bind to human VEGF-A and human ANG2. In one aspect, the invention provides antibodies that specifically bind to human VEGF-A and human ANG2.

In certain aspects, an antibody that binds to human VEGF-A and to human ANG2 is provided, wherein the antibody comprises a VEGF-A paratope (i.e. an antigen binding site that binds to VEGF-A) and an ANG2 paratope (i.e. an antigen binding site that binds to ANG2) within one cognate pair of a VL domain and a VH domain, wherein the VEGF-A paratope comprises amino acid residues from CDR-H2, CDR-L1 and CDR-L3 of the antibody, wherein the ANG2 paratope comprises amino acid residues from the CDR-H1, CDR-H3 and CDR-L2 of the antibody; and/or the pair of the variable light chain domain and the variable heavy chain domain simultaneously binds to human VEGF-A and human ANG2; and/or the antibody binds to the same epitope on human VEGF-A and to the same epitope on human ANG2 as an antibody with a variable heavy chain domain of SEQ ID NO: 19 and a variable light chain domain SEQ ID NO: 20; and/or an antibody Fab fragment of the antibody binds (i) to human VEGF-A121 with a $K_D$ of less than 50 pM as measured by KinExA®, and (ii) to human ANG2 with a $K_D$ of less than 50 pM as measured by KinExA®; and/or an antibody Fab fragment of the antibody exhibits an aggregation onset temperature of 70° C. or more; and/or an antibody Fab fragment of the antibody exhibits a melting temperature of more than 80° C. as measured by dynamic light scattering; and/or a 20 mM His/HisHCl, pH 6.0 solution comprising 180 mg/ml of the antibody Fab fragment has a viscosity of less than 20 cP at 20° C. as detected by dynamic light scattering with a latex-bead DLS method as described in Example 8.

In another aspect, the invention provides an antibody that binds to human VEGF-A and to human ANG2 comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, and a VL domain comprising (d) CDR-L1 comprising the amino acid sequence of SEQ ID NO:22, (e) CDR-L2 comprising the amino acid sequence of SEQ ID NO:23, and (f) CDR-L3 comprising the amino acid sequence of SEQ ID NO:8.

In another aspect, the invention provides an antibody that binds to human VEGF-A and to human ANG2 comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, (d) a human heavy chain framework with (i) FR1 comprising amino acid residues H3, D26, F27, E29, and Y30, (ii) FR3 comprising amino acid residues R66 and R94; and a VL domain comprising (e) CDR-L1 comprising the amino acid sequence of SEQ ID NO:22, (f) CDR-L2 comprising the amino acid sequence of SEQ ID NO:23, (g) CDR-L3 comprising the amino acid sequence of SEQ ID NO:8, and (h) a human light chain framework with (i) FR1 comprising amino acid residues I2 and Y3, (ii) FR2 comprising amino acid residues L46 and F49, (iii) FR3 comprising amino acid residue E57, wherein the numbering of the VH and VL domains is according to the Kabat numbering system.

In another aspect, the invention provides an antibody that binds to human VEGF-A and to human ANG2 comprising a VH domain comprising amino acid residues H3, D26, F27, E29, Y30, D35b, D35c, D55, H56, K57, Y58, T61, K62, F63, I64, G65, R66, R94, D95, V96, F98, and F99, and a VL domain comprising amino acid residues I2, Y3, Y27, W27a, E32, L46, F49, D50, F53, K54, V55, Y56, E57, Y91, R92, Y93, H94, and P95, wherein the numbering of the VH and VL domains is according to the Kabat numbering system. In one embodiment the antibody comprises a VEGF-A paratope comprising the following amino acid residues in the VH domain D35c, D55, H56, K57, Y58, T61, K62, F63, I64, G65, R66, and D95, and the following amino acid residues in the VL domain I2, Y3, Y27, W27a, E32, R92, Y93, H94, and P95; and an ANG2 paratope comprising the following amino acid residues in the VH domain H3, D26, F27, E29, Y30, D35b, R94, V96, F98, and F99, and the following amino acid residues in the VL domain E32, L46, F49, D50, F53, K54, V55, Y56, E57, and Y91.

In another aspect, the invention provides an antibody that binds to human VEGF-A and to human ANG2 comprising (a) a VH domain comprising an amino acid sequence having at least 85%, 86%, 87%, 88%, 89%, 90%, 91%, 92%, 93%, 94%, 95%, 96%, 97%, 98% or 99% sequence identity to the amino acid sequence of SEQ ID NO:19; and (b) a VL domain comprising an amino acid sequence having at least 85%, 86%, 87%, 88%, 89%, 90%, 91%, 92%, 93%, 94%, 95%, 96%, 97%, 98% or 99% sequence identity to the amino acid sequence of SEQ ID NO:20.

In another aspect, the invention provides an antibody that binds to human VEGF-A and to human ANG2 comprising (a) a VH domain comprising an amino acid sequence having at least 85%, 86%, 87%, 88%, 89%, 90%, 91%, 92%, 93%, 94%, 95%, 96%, 97%, 98% or 99% sequence identity to the amino acid sequence of SEQ ID NO:19, wherein the VH domain comprises amino acid residues H3, D26, F27, E29, Y30, D35b, D35c, D55, H56, K57, Y58, T61, K62, F63, I64, G65, R66, R94, D95, V96, F98, and F99; and (b) a VL domain comprising an amino acid sequence having at least 85%, 86%, 87%, 88%, 89%, 90%, 91%, 92%, 93%, 94%, 95%, 96%, 97%, 98% or 99% sequence identity to the amino acid sequence of SEQ ID NO:20, wherein the VL domain comprises amino acid residues I2, Y3, Y27, W27a, E32, L46, F49, D50, F53, K54, V55, Y56, E57, Y91, R92, Y93, H94, and P95, wherein the numbering of the VH and VL domains is according to the Kabat numbering system.

In another aspect, the invention provides an antibody that binds to human VEGF-A and to human ANG2 comprising a VH domain comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, and a VL domain comprising (d) CDR-L1 comprising the amino acid sequence of SEQ ID NO:22, (e) CDR-L2 comprising the amino acid sequence of SEQ ID NO:23, and (f) CDR-L3 comprising the amino acid sequence of SEQ ID NO:8, comprising (a) a VH domain comprising an amino acid sequence having at least 85%, 86%, 87%, 88%, 89%, 90%, 91%, 92%, 93%, 94%, 95%, 96%, 97%, 98% or 99% sequence identity to the amino acid sequence of SEQ ID NO:19; and (b) a VL domain comprising an amino acid sequence having at least 85%, 86%, 87%, 88%, 89%, 90%, 91%, 92%, 93%, 94%, 95%, 96%, 97%, 98% or 99% sequence identity to the amino acid sequence of SEQ ID NO:20.

In another aspect, the invention provides an antibody that binds to human VEGF-A and to human ANG2 comprising a VH domain comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, and a VL domain comprising (d) CDR-L1 comprising the amino acid sequence of SEQ ID NO:22, (e) CDR-L2 comprising the amino acid sequence of SEQ ID NO:23, and (f) CDR-L3 comprising the amino acid sequence of SEQ ID NO:8, comprising (a) a VH domain comprising an amino acid sequence having at least 85%, 86%, 87%, 88%, 89%, 90%, 91%, 92%, 93%, 94%, 95%, 96%, 97%, 98% or 99% sequence identity to the amino acid sequence of SEQ ID NO:19, wherein the VH domain comprises amino acid residues H3, D26, F27, E29, Y30, R66 and R94; and (b) a VL domain comprising an amino acid sequence having at least 90% sequence identity to the amino acid sequence of SEQ ID NO:20, wherein the VL domain comprises amino acid residues I2, Y3, L46, F49, and E57, wherein the numbering of the VH and VL domains is according to the Kabat numbering system.

In another aspect, the invention provides an antibody that binds to human VEGF-A and to human ANG2 comprising a VH domain comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, (d) a human heavy chain framework with (i) FR1 comprising amino acid residues H3, D26, F27, E29, and Y30, (ii) FR3 comprising amino acid residues R66 and R94; and a VL domain comprising (e) CDR-L1 comprising the amino acid sequence of SEQ ID NO:22, (f) CDR-L2 comprising the amino acid sequence of SEQ ID NO:23, (g) CDR-L3 comprising the amino acid sequence of SEQ ID NO:8, and (h) a human light chain framework with (i) FR1 comprising amino acid residues 12 and Y3, (ii) FR2 comprising amino acid residues L46 and F49, (iii) FR3 comprising amino acid residue E57, wherein the numbering of the VH and VL domains is according to the Kabat numbering system, comprising (a) a VH domain comprising an amino acid sequence having at least 85%, 86%, 87%, 88%, 89%, 90%, 91%, 92%, 93%, 94%, 95%, 96%, 97%, 98% or 99% sequence identity to the amino acid sequence of SEQ ID NO:19; and (b) a VL domain comprising an amino acid sequence having at least 85%, 86%, 87%, 88%, 89%, 90%, 91%, 92%, 93%, 94%, 95%, 96%, 97%, 98% or 99% sequence identity to the amino acid sequence of SEQ ID NO:20.

In another aspect, the invention provides an antibody that binds to human VEGF-A and to human ANG2 comprising (a) a VH domain comprising an amino acid sequence of SEQ ID NO:19 with 1 to 15, 1 to 10, or 1 to 5 amino acid substitutions; and (b) a variable light chain domain comprising an amino acid sequence of SEQ ID NO:20 with 1 to 15, 1 to 10, or 1 to 5 amino acid substitutions.

In another aspect, the invention provides an antibody that binds to human VEGF-A and to human ANG2 comprising (a) a VH domain comprising an amino acid sequence of SEQ ID NO:19 with 1 to 15, 1 to 10, or 1 to 5 amino acid substitutions, wherein the amino acid substitutions are located at one or more of positions 1, 2, 4 to 25, 28, 35d to 54, 59, 60, 67 to 93, 97, 101 to 113 of SEQ ID NO:19; and (b) a variable light chain domain comprising an amino acid sequence of SEQ ID NO:20 with 1 to 15, 1 to 10, or 1 to 5 amino acid substitutions, wherein the amino acid substitutions are located at positions 1, 4 to 26, 27b to 27d, 33 to 45, 47, 48, 51, 52, 58 to 90, 96 to 107 of SEQ ID NO:20, wherein the numbering of the VH and VL domains is according to the Kabat numbering system.

In another aspect, the invention provides an antibody that binds to human VEGF-A and to human ANG2 comprising a VH domain comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, and a VL domain comprising (d) CDR-L1 comprising the amino acid sequence of SEQ ID NO:22, (e) CDR-L2 comprising the amino acid sequence of SEQ ID NO:23, and (f) CDR-L3 comprising the amino acid sequence of SEQ ID NO:8, comprising (a) a VH domain comprising an amino acid sequence of SEQ ID NO:19 with 1 to 15, 1 to 10, or 1 to 5 amino acid substitutions; and (b) a variable light chain domain comprising an amino acid sequence of SEQ ID NO:20 with 1 to 15, 1 to 10, or 1 to 5 amino acid substitutions.

In another aspect, the invention provides an antibody that binds to human VEGF-A and to human ANG2 comprising a VH domain comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, (d) a human heavy chain framework with (i) FR1 comprising amino acid residues H3, D26, F27, E29, and Y30, (ii) FR3 comprising amino acid residues R66 and R94; and a VL domain comprising (e) CDR-L1 comprising the amino acid sequence of SEQ ID NO:22, (f) CDR-L2 comprising the amino acid sequence of SEQ ID NO:23, (g) CDR-L3 comprising the amino acid sequence of SEQ ID NO:8, and (h) a human light chain framework with (i) FR1 comprising amino acid residues 12 and Y3, (ii) FR2 comprising amino acid residues L46 and F49, (iii) FR3 comprising amino acid residue E57, wherein the numbering of the VH and VL domains is according to the Kabat numbering system, and comprising (a) a VH domain comprising an amino acid sequence of SEQ ID NO:19 with 1 to 15, 1 to 10, or 1 to 5 amino acid substitutions; and (b) a variable light chain domain comprising an amino acid sequence of SEQ ID NO:20 with 1 to 15, 1 to 10, or 1 to 5 amino acid substitutions.

In one aspect, the invention provides an antibody that binds to human VEGF-A and to human ANG2 comprising a VH domain having at least 90%, 91%, 92%, 93%, 94%, 95%, 96%, 97%, 98%, 99%, or 100% sequence identity to the amino acid sequence of SEQ ID NO:19. In certain aspects, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody that binds to human VEGF-A and human ANG2 comprising that sequence retains the ability to bind to to human VEGF-A and human ANG2. In certain aspects, a total of 1 to 10 amino acids have been substituted, inserted and/or deleted in SEQ ID NO:19. In certain aspects, substitutions, insertions, or deletions occur in regions outside the CDRs (i.e., in the FRs). In a particular aspect, the VH comprises a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14.

In one aspect, the invention provides an antibody that binds to human VEGF-A and to human ANG2 comprising a VL domain having at least 90%, 91%, 92%, 93%, 94%, 95%, 96%, 97%, 98%, 99%, or 100% sequence identity to the amino acid sequence of SEQ ID NO:20. In certain aspects, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody that binds to human VEGF-A and human ANG2 comprising that sequence retains the ability to bind to to human VEGF-A and human ANG2. In certain aspects, a total of 1 to 10 amino acids have been substituted, inserted and/or deleted in SEQ ID NO:20. In certain aspects, substitutions, insertions, or deletions occur in regions outside the CDRs (i.e., in the FRs). In a particular aspect, the VL comprises (d) CDR-L1 comprising the amino acid sequence of SEQ ID NO:22, (e) CDR-L2 comprising the amino acid sequence of SEQ ID NO:23, and (f) CDR-L3 comprising the amino acid sequence of SEQ ID NO:8.

In another aspect, an antibody that binds to human VEGF-A and human ANG2 is provided, wherein the antibody comprises a VH sequence as in any of the aspects provided above, and a VL sequence as in any of the aspects provided above. In one aspect, the antibody comprises the VH and VL sequences SEQ ID NO:19 and SEQ ID NO:20, respectively, including post-translational modifications of those sequences.

In another aspect, an antibody that binds to human VEGF-A and human ANG2 is provided, wherein the antibody comprises a heavy chain amino acid sequence of SEQ ID NO:24 and a light chain amino acid sequence of SEQ ID NO:25.

In another aspect, an antibody that binds to human VEGF-A and human ANG2 is provided, wherein the antibody comprises a heavy chain amino acid sequence of SEQ ID NO:17 and a light chain amino acid sequence of SEQ ID NO:18.

In a further aspect of the invention, an antibody that binds to human VEGF-A and human ANG2 according to any of the above aspects is a monoclonal antibody. In one aspect, an antibody that binds to human VEGF-A and human ANG2 is an antibody fragment, e.g., a Fv, Fab, Fab', scFv, diabody, or F(ab')2 fragment. In another aspect, the antibody is a full length antibody.

In a further aspect, an antibody that binds to human VEGF-A and human ANG2 according to any of the above aspects may incorporate any of the features, singly or in combination, as described in Sections 1-5 below:

1. Antibody Affinity

In certain embodiments, an antibody provided herein binds to VEGF-A with a dissociation constant ($K_D$) of ≤1 nM, ≤0.1 nM, or ≤0.01 nM. In a preferred embodiment an antibody provided herein binds to human VEGF-A with a dissociation constant ($K_D$) of ≤10 pM, in a preferred embodiment ≤5 pM. In a preferred embodiment an antibody provided herein binds to human VEGFA-121 with a dissociation constant ($K_D$) of ≤10 pM, in a preferred embodiment ≤5 pM. In a preferred embodiment an antibody provided herein binds to human VEGFA-165 with a dissociation constant ($K_D$) of ≤10 pM, in a preferred embodiment ≤5 pM.

In certain embodiments, an antibody that binds to ANG2 has a dissociation constant ($K_D$) of ≤1 nM, ≤0.1 nM, or ≤0.03 nM. In a preferred embodiment an antibody provided herein binds to human ANG2 with a dissociation constant ($K_D$) of ≤10 pM, in a preferred embodiment ≤5 pM.

In one aspect, $K_D$ is measured using a BIACORE® surface plasmon resonance assay.

In another aspect, $K_D$ is measured using a KinExA® assay. In one embodiment, $K_D$ is measured using a KinExA® assay under the conditions as described below in the Materials & general methods section for either detection of $K_D$ of VEGF-A binding or detection of $K_D$ of ANG2 binding.

For example, the $K_D$ of antibody binding to VEGF-A is measured in an assay using a KinExA® 3200 instrument from Sapidyne Instruments (Boise, Id.), PMMA beads are coated with antigen according to the KinExA® Handbook protocol (Adsorption coating, Sapidyne) using 30 µg of Anti-VEGF-Antibody MAB293 (R&D) in 1 ml PBS (pH7.4). KinExA® equilibrium assay is performed at room temperature using PBS pH 7.4 with 0.01% BSA and 0.01% Tween® 20 as running buffer, samples and beads are prepared in LowCross-Buffer® (Candor Bioscience). A flow rate of 0.25 ml/min is used. A constant amount of VEGFA-121-His (50 pM and in a second experiment 500 pM) is titrated with the tested antibody and equilibrated mixtures are drawn through a column of anti-VEGF antibody (Mab293) coupled beads in the KinExA® system at a volume of 750 µl for 50 pM constant VEGF and at a volume of 125 µl for 500 pM constant VEGF. Detection of bound VEGFA-121 is done using a second biotinylated anti-VEGF antibody (BAF293) with a concentration of 250 ng/ml and following by an injection of 250 ng/ml Streptavidin Alexa Fluor™ 647 conjugate in sample buffer. The $K_D$ is obtained from non-linear regression analysis of the data using a one-site homogeneous binding model contained within the KinExA® software (Version 4.0.11) using the "standard analysis" method. The software calculates the $K_D$ and determines the 95% confidence interval by fitting the data points to a theoretical $K_D$ curve. The 95% confidence interval is given as $K_D$ low and $K_D$ high.

For example, the $K_D$ of antibody binding to ANG2 is measured in an assay using a KinExA® 3200 instrument from Sapidyne Instruments (Boise, Id.), PMMA beads are coated with antigen according to the KinExA® Handbook protocol (Adsorption coating, Sapidyne) using 20 µg of anti-Ang2-Antibody MAB098 (R&D) in 1 ml PBS (pH7.4). KinExA® equilibrium assay is performed at room temperature using PBS pH 7.4 with 0.01% BSA and 0.01% Tween® 20 as running buffer, samples and beads are prepared in LowCross-Buffer® (Candor Bioscience). A flow rate of 0.25 ml/min is used. A constant amount Ang2-RBD-muFc (50 pM and in a second experiment 500 pM) is titrated with the tested antibody and equilibrated mixtures are drawn through a column of Anti-Ang2 antibody (MAB098) coupled beads in the KinExA® system at a volume of 750 µl for 50 pM constant Ang2 and at a volume of 188 µl for 500 pM constant Ang2. Detection of bound Ang2 is done using a second biotinylated anti-Ang2 antibody (BAM0981) with a concentration of 250 ng/ml and following by an injection of 250 ng/ml Streptavidin Alexa Fluor™ 647 conjugate in sample buffer. The $K_D$ is obtained from non-linear regression analysis of the data using a one-site homogeneous binding model contained within the KinExA® software (Version 4.0.11) using the "standard analysis" method. The software calculates the $K_D$ and determines the 95% confidence interval by fitting the data points to a theoretical $K_D$ curve. The 95% confidence interval is given as $K_D$ low and $K_D$ high.

2. Antibody Fragments

In certain aspects, an antibody provided herein is an antibody fragment.

In one aspect, the antibody fragment is a Fab, Fab', Fab'-SH, or F(ab')$_2$ fragment, in particular a Fab fragment. Papain digestion of intact antibodies produces two identical antigen-binding fragments, called "Fab" fragments containing each the heavy- and light-chain variable domains (VH and VL, respectively) and also the constant domain of the light chain (CL) and the first constant domain of the heavy chain (CH1). The term "Fab fragment" thus refers to an antibody fragment comprising a light chain comprising a VL domain and a CL domain, and a heavy chain fragment comprising a VH domain and a CH1 domain. "Fab' fragments" differ from Fab fragments by the addition of residues at the carboxy terminus of the CH1 domain including one or more cysteines from the antibody hinge region. Fab'-SH are Fab' fragments in which the cysteine residue(s) of the constant domains bear a free thiol group. Pepsin treatment yields an F(ab')2 fragment that has two antigen-binding sites (two Fab fragments) and a part of the Fc region. For discussion of Fab and F(ab')2 fragments comprising salvage receptor binding epitope residues and having increased in vivo half-life, see U.S. Pat. No. 5,869,046.

Antibody fragments can be made by various techniques, including but not limited to proteolytic digestion of an intact antibody as well as recombinant production by recombinant host cells (e.g., E. coli, CHO), as described herein.

In a preferred embodiment the antibody provided herein is a Fab fragment.

In one embodiment the VH domain of the antibody provided herein comprises a human VH3 framework.

In one embodiment the VL domain of the antibody provided herein comprises a human Vkappa1 framework.

In one embodiment the CL domain of the antibody provided herein is of kappa isotype.

In one embodiment the CH1 domain of the antibody provided herein is of human IgG1 isotype.

In a preferred embodiment, the antibody provided herein is a Fab fragment comprising a CL domain of kappa isotype and a CH1 domain of human IgG1 isotype.

3. Thermal Stability

Antibodies provided herein exhibit superior thermal stability. In certain embodiments, a Fab fragment of an antibody provided herein exhibits an aggregation onset temperature of 70° C. or more. In certain embodiments, a Fab fragment of an antibody provided herein exhibits a melting temperature of more than 80° C. as measured by dynamic light scattering.

4. Multispecific Antibodies

In certain aspects, an antibody provided herein is a multispecific antibody. "Multispecific antibodies" are monoclonal antibodies that have binding specificities for at least two different sites, i.e., different epitopes on different antigens or different epitopes on the same antigen. In certain aspects, the multispecific antibody has three or more binding specificities.

Multispecific antibodies with three or more binding specificities comprising antibodies provided herein may be provided in an asymmetric form with a domain crossover in one or more binding arms of the same antigen specificity, i.e. by exchanging the VH/VL domains (see e.g., WO 2009/080252 and WO 2015/150447), the CH1/CL domains (see e.g., WO 2009/080253) or the complete Fab arms (see e.g., WO 2009/080251, WO 2016/016299, also see Schaefer et al, PNAS, 108 (2011) 1187-1191, and Klein at al., MAbs 8 (2016) 1010-20). Various further molecular formats for multispecific antibodies are known in the art and are included herein (see e.g., Spiess et al., Mol Immunol 67 (2015) 95-106).

5. Antibody Variants

In certain aspects, amino acid sequence variants of the antibodies provided herein are contemplated. For example, it may be desirable to alter the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In certain aspects, antibody variants having one or more amino acid substitutions are provided. Sites of interest for substitutional mutagenesis include the CDRs and FRs. Conservative substitutions are shown in the Table beolw under the heading of "preferred substitutions". More substantial changes are provided in Table 1 under the heading of "exemplary substitutions", and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for a member of another class.

One type of substitutional variant involves substituting one or more CDR residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more CDR residues are mutated and the variant antibodies displayed on phage and screened for a particular biological activity (e.g., binding affinity).

In certain aspects, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in the CDRs. Such alterations may, for example, be outside of antigen contacting residues in the CDRs. In certain variant VH and VL sequences provided above, each CDR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex may be used to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT (antibody directed enzyme prodrug therapy)) or a polypeptide which increases the serum half-life of the antibody.

a) Glycosylation Variants

In certain aspects, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the oligosaccharide attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some aspects, modifications of the oligosaccharide in an antibody of the invention may be made in order to create antibody variants with certain improved properties.

In one aspect, antibody variants are provided having a non-fucosylated oligosaccharide, i.e. an oligosaccharide structure that lacks fucose attached (directly or indirectly) to an Fc region. Such non-fucosylated oligosaccharide (also referred to as "afucosylated" oligosaccharide) particularly is an N-linked oligosaccharide which lacks a fucose residue attached to the first GlcNAc in the stem of the biantennary oligosaccharide structure. In one aspect, antibody variants are provided having an increased proportion of non-fucosylated oligosaccharides in the Fc region as compared to a native or parent antibody. For example, the proportion of non-fucosylated oligosaccharides may be at least about 20%, at least about 40%, at least about 60%, at least about 80%, or even about 100% (i.e. no fucosylated oligosaccharides are present). The percentage of non-fucosylated oligosaccharides is the (average) amount of oligosaccharides lacking fucose residues, relative to the sum of all oligosaccharides attached to Asn 297 (e. g. complex, hybrid and high mannose structures) as measured by MALDI-TOF mass spectrometry, as described in WO 2006/082515, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such antibodies having an increased proportion of non-fucosylated oligosaccharides in the Fc region may have improved FcγRIIIa receptor binding and/or improved effector function, in particular improved ADCC function. See, e.g., US 2003/0157108; US 2004/0093621.

Examples of cell lines capable of producing antibodies with reduced fucosylation include Lec13 CHO cells deficient in protein fucosylation (Ripka et al. *Arch. Biochem. Biophys.* 249:533-545 (1986); US 2003/0157108; and WO 2004/056312, especially at Example 11), and knockout cell lines, such as alpha-1,6-fucosyltransferase gene, FUT8, knockout CHO cells (see, e.g., Yamane-Ohnuki et al. *Biotech. Bioeng.* 87:614-622 (2004); Kanda, Y. et al., *Biotechnol. Bioeng.*, 94(4):680-688 (2006); and WO 2003/085107), or cells with reduced or abolished activity of a GDP-fucose synthesis or transporter protein (see, e.g., US2004259150, US2005031613, US2004132140, US2004110282).

In a further aspect, antibody variants are provided with bisected oligosaccharides, e.g., in which a biantennary oligosaccharide attached to the Fc region of the antibody is bisected by GlcNAc. Such antibody variants may have reduced fucosylation and/or improved ADCC function as described above. Examples of such antibody variants are described, e.g., in Umana et al., Nat Biotechnol 17, 176-180 (1999); Ferrara et al., Biotechn Bioeng 93, 851-861 (2006); WO 99/54342; WO 2004/065540, WO 2003/011878.

Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

b) Fc Region Variants

In certain aspects, one or more amino acid modifications may be introduced into the Fc region of an antibody provided herein, thereby generating an Fc region variant. The Fc region variant may comprise a human Fc region sequence (e.g., a human $IgG_1$, $IgG_2$, $IgG_3$ or $IgG_4$ Fc region) comprising an amino acid modification (e.g., a substitution) at one or more amino acid positions.

In certain aspects, the invention contemplates an antibody variant that possesses some but not all effector functions, which make it a desirable candidate for applications in which the half life of the antibody in vivo is important yet certain effector functions (such as complement-dependent cytotoxicity (CDC) and antibody-dependent cell-mediated cytotoxicity (ADCC)) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g., Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:

1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006); WO 2013/120929 A1).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain aspects, an antibody variant comprises an Fc region with one or more amino acid substitutions which improve ADCC, e.g., substitutions at positions 298, 333, and/or 334 of the Fc region (EU numbering of residues).

In certain aspects, an antibody variant comprises an Fc region with one or more amino acid substitutions which diminish FcγR binding, e.g., substitutions at positions 234 and 235 of the Fc region (EU numbering of residues). In one aspect, the substitutions are L234A and L235A (LALA). In certain aspects, the antibody variant further comprises D265A and/or P329G in an Fc region derived from a human IgG$_1$ Fc region. In one aspect, the substitutions are L234A, L235A and P329G (LALA-PG) in an Fc region derived from a human IgG$_1$ Fc region. (See, e.g., WO 2012/130831). In another aspect, the substitutions are L234A, L235A and D265A (LALA-DA) in an Fc region derived from a human IgG$_1$ Fc region.

In some aspects, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934 (Hinton et al.). Those antibodies comprise an Fc region with one or more substitutions therein which improve binding of the Fc region to FcRn. Such Fc variants include those with substitutions at one or more of Fc region residues: 238, 252, 254, 256, 265, 272, 286, 303, 305, 307, 311, 312, 317, 340, 356, 360, 362, 376, 378, 380, 382, 413, 424 or 434, e.g., substitution of Fc region residue 434 (See, e.g., U.S. Pat. No. 7,371,826; Dall'Acqua, W. F., et al. J. Biol. Chem. 281 (2006) 23514-23524).

Fc region residues critical to the mouse Fc-mouse FcRn interaction have been identified by site-directed mutagenesis (see e.g. Dall'Acqua, W. F., et al. J. Immunol 169 (2002) 5171-5180). Residues I253, H310, H433, N434, and H435 (EU index numbering) are involved in the interaction (Medesan, C., et al., Eur. J. Immunol. 26 (1996) 2533; Firan, M., et al., Int. Immunol. 13 (2001) 993; Kim, J. K., et al., Eur. J. Immunol. 24 (1994) 542). Residues I253, H310, and H435 were found to be critical for the interaction of human Fc with murine FcRn (Kim, J. K., et al., Eur. J. Immunol. 29 (1999) 2819). Studies of the human Fc-human FcRn complex have shown that residues I253, S254, H435, and Y436 are crucial for the interaction (Firan, M., et al., Int. Immunol. 13 (2001) 993; Shields, R. L., et al., J. Biol. Chem. 276 (2001) 6591-6604). In Yeung, Y. A., et al. (J. Immunol. 182 (2009) 7667-7671) various mutants of residues 248 to 259 and 301 to 317 and 376 to 382 and 424 to 437 have been reported and examined.

In certain aspects, an antibody variant comprises an Fc region with one or more amino acid substitutions, which reduce FcRn binding, e.g., substitutions at positions 253, and/or 310, and/or 435 of the Fc-region (EU numbering of residues). In certain aspects, the antibody variant comprises an Fc region with the amino acid substitutions at positions 253, 310 and 435. In one aspect, the substitutions are I253A, H310A and H435A in an Fc region derived from a human IgG1 Fc-region. See, e.g., Grevys, A., et al., J. Immunol. 194 (2015) 5497-5508.

In certain aspects, an antibody variant comprises an Fc region with one or more amino acid substitutions, which reduce FcRn binding, e.g., substitutions at positions 310, and/or 433, and/or 436 of the Fc region (EU numbering of residues). In certain aspects, the antibody variant comprises an Fc region with the amino acid substitutions at positions 310, 433 and 436. In one aspect, the substitutions are H310A, H433A and Y436A in an Fc region derived from a human IgG1 Fc-region. (See, e.g., WO 2014/177460 A1).

In certain aspects, an antibody variant comprises an Fc region with one or more amino acid substitutions which increase FcRn binding, e.g., substitutions at positions 252, and/or 254, and/or 256 of the Fc region (EU numbering of residues). In certain aspects, the antibody variant comprises an Fc region with amino acid substitutions at positions 252, 254, and 256. In one aspect, the substitutions are M252Y, S254T and T256E in an Fc region derived from a human IgG$_1$ Fc-region. See also Duncan & Winter, *Nature* 322:738-40 (1988); U.S. Pat. Nos. 5,648,260; 5,624,821; and WO 94/29351 concerning other examples of Fc region variants.

The C-terminus of the heavy chain of the antibody as reported herein can be a complete C-terminus ending with the amino acid residues PGK. The C-terminus of the heavy chain can be a shortened C-terminus in which one or two of the C terminal amino acid residues have been removed. In one preferred aspect, the C-terminus of the heavy chain is a shortened C-terminus ending PG. In one aspect of all aspects as reported herein, an antibody comprising a heavy chain including a C-terminal CH3 domain as specified herein, comprises the C-terminal glycine-lysine dipeptide (G446 and K447, EU index numbering of amino acid positions). In one aspect of all aspects as reported herein, an antibody comprising a heavy chain including a C-terminal CH3 domain, as specified herein, comprises a C-terminal glycine residue (G446, EU index numbering of amino acid positions).

c) Cysteine Engineered Antibody Variants

In certain aspects, it may be desirable to create cysteine engineered antibodies, e.g., THIOMAB™ antibodies, in which one or more residues of an antibody are substituted with cysteine residues. In particular aspects, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. Cysteine engineered antibodies may be generated as described, e.g., in U.S. Pat. Nos. 7,521,541, 8,30,930, 7,855,275, 9,000,130, or WO 2016040856.

6. Immunoconjugates

The invention also provides immunoconjugates comprising an antibody provided herein conjugated (chemically bonded) to one or more agents; in one embodiment such as cytotoxic agents, chemotherapeutic agents, drugs, growth inhibitory agents, toxins (e.g., protein toxins, enzymatically active toxins of bacterial, fungal, plant, or animal origin, or fragments thereof), or radioactive isotopes.

In one embodiment the invention provides immunoconjugates comprising an antibody provided herein conjugated to a polymer. The term "polymer" used herein includes chemical polymers and protein polymers. In one embodiment the immunoconjugate comprises the antibody provided herein conjugated to an extended recombinant polypeptide (XTEN). "Extended recombinant polypeptides" are known in the art and are, e.g. disclosed in US20190083577. In one embodiment the immunoconjugate comprises an XTEN (a) comprising a sequence selected from GGSPAGSCTSP, GASASCAPSTG, TAEAAGCGTAEAA, and GPEPTCPAPSG. (b) being 36 to 3000 L-amino acid residues in length, and/or (c) wherein the sum of glycine (G), alanine (A), serine (S), threonine (T), glutamate (E) and proline (P) residues constitutes more than 90% of the total amino acid residues of the XTEN.

B. Recombinant Methods and Compositions

Antibodies may be produced using recombinant methods and compositions, e.g., as described in U.S. Pat. No. 4,816,567. For these methods one or more isolated nucleic acid(s) encoding an antibody are provided.

In one aspect, isolated nucleic acids encoding an antibody of the invention are provided.

In one aspect, a method of making an antibody that binds to human VEGF-A and human ANG2 is provided, wherein the method comprises culturing a host cell comprising nucleic acid(s) encoding the antibody, as provided above, under conditions suitable for expression of the antibody, and optionally recovering the antibody from the host cell (or host cell culture medium).

For recombinant production of an antibody that binds to human VEGF-A and human ANG2, nucleic acids encoding the antibody, e.g., as described above, are isolated and inserted into one or more vectors for further cloning and/or expression in a host cell. Such nucleic acids may be readily isolated and sequenced using conventional procedures (e.g., by using oligonucleotide probes that are capable of binding specifically to genes encoding the heavy and light chains of the antibody) or produced by recombinant methods or obtained by chemical synthesis.

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B. K. C. (ed.), Humana Press, Totowa, N.J. (2003), pp. 245-254, describing expression of antibody fragments in $E.\ coli$.) After expression, the antibody may be isolated from the bacterial cell paste in a soluble fraction and can be further purified. In one embodiment the host cell is an $E.\ coli$ cell.

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells (as described, e.g., in Mather, J. P. et al., Annals N.Y. Acad. Sci. 383 (1982) 44-68); MRC 5 cells; and FS4 cells. Other useful mammalian host cell lines include Chinese hamster ovary (CHO) cells, including DHFR– CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K C. (ed.), Humana Press, Totowa, N.J. (2004), pp. 255-268.

In one aspect, the host cell is eukaryotic, e.g., a Chinese Hamster Ovary (CHO) cell or lymphoid cell (e.g., Y0, NS0, Sp20 cell). In one preferred embodiment the host cell is a CHO cell. Production of antibodies of the invention in CHO cells may improve syringeability of the antibody.

C. Pharmaceutical Compositions

In a further aspect, provided are pharmaceutical compositions comprising any of the antibodies provided herein, e.g., for use in any of the below therapeutic methods. In one aspect, a pharmaceutical composition comprises any of the antibodies provided herein and a pharmaceutically acceptable carrier. In another aspect, a pharmaceutical composition comprises any of the antibodies provided herein and at least one additional therapeutic agent, e.g., as described below.

Pharmaceutical compositions of an antibody that binds to human VEGF-A and human ANG2 as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized compositions or aqueous solutions. Pharmaceutically acceptable carriers are generally nontoxic to recipients at the dosages and concentrations employed, and include, but are not limited to: buffers such as histidine, phosphate, citrate, acetate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Halozyme, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody compositions are described in U.S. Pat. No. 6,267,958. Aqueous antibody compositions include those described in U.S. Pat. No. 6,171,586 and WO 2006/044908, the latter compositions including a histidine-acetate buffer.

The pharmaceutical composition herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Pharmaceutical compositions for sustained-release may be prepared. Suitable examples of sustained-release preparations include semipermeable matrices of solid hydrophobic polymers containing the antibody, which matrices are in the form of shaped articles, e.g., films, or microcapsules.

The pharmaceutical compositions to be used for in vivo administration are generally sterile. Sterility may be readily accomplished, e.g., by filtration through sterile filtration membranes.

D. Therapeutic Methods and Routes of Administration

Any of the antibodies that bind to human VEGF-A and human ANG2 provided herein may be used in therapeutic methods.

In one aspect, an antibody that binds to human VEGF-A and human ANG2 for use as a medicament is provided. In further aspects, an antibody that binds to human VEGF-A and human ANG2 for use in treating a vascular disease is provided. In certain aspects, an antibody that binds to human VEGF-A and human ANG2 for use in a method of treatment is provided. In certain aspects, the invention provides an antibody that binds to human VEGF-A and human ANG2 for use in a method of treating an individual having a vascular disease comprising administering to the individual an effective amount of the antibody that binds to human VEGF-A and human ANG2. In one such aspect, the method further comprises administering to the individual an effective amount of at least one additional therapeutic agent (e.g., one, two, three, four, five, or six additional therapeutic agents), e.g., as described below. In further aspects, the invention provides an antibody that binds to human VEGF-A and human ANG2 for use in inhibiting angiogenesis. In certain aspects, the invention provides an antibody that binds to human VEGF-A and human ANG2 for use in a method inhibiting angiogenesis in an individual comprising administering to the individual an effective amount of the antibody that binds to human VEGF-A and human ANG2 to inhibit angiogenesis. An "individual" according to any of the above aspects is preferably a human.

In further aspects, an antibody that binds to human VEGF-A and human ANG2 for use in treating an ocular disease is provided. In one embodiment the ocular disease is selected from AMD (in one embodiment wet AMD, dry AMD, intermediate AMD, advanced AMD, and geographic atrophy (GA)), macular degeneration, macular edema, DME (in one embodiment focal, non-center DME and diffuse, center-involved DME), retinopathy, diabetic retinopathy (DR) (in one embodiment proliferative DR (PDR), non-proliferative DR (NPDR), and high-altitude DR), other ischemia-related retinopathies, ROP, retinal vein occlusion (RVO) (in one embodiment central (CRVO) and branched (BRVO) forms), CNV (in one embodiment myopic CNV), corneal neovascularization, diseases associated with corneal neovascularization, retinal neovascularization, diseases associated with retinal/choroidal neovascularization, central serous retinopathy (CSR), pathologic myopia, von Hippel-Lindau disease, histoplasmosis of the eye, FEVR, Coats' disease, Norrie Disease, retinal abnormalities associated with osteoporosis-pseudoglioma syndrome (OPPG), subconjunctival hemorrhage, rubeosis, ocular neovascular disease, neovascular glaucoma, retinitis pigmentosa (RP), hypertensive retinopathy, retinal angiomatous proliferation, macular telangiectasia, iris neovascularization, intraocular neovascularization, retinal degeneration, cystoid macular edema (CME), vasculitis, papilloedema, retinitis, including but not limited to CMV retinitis, ocular melanoma, retinal blastoma, conjunctivitis (in one embodiment infectious conjunctivitis and non-infectious (in one embodiment allergic) conjunctivitis), Leber congenital amaurosis (also known as Leber's congenital amaurosis or LCA), uveitis (including infectious and non-infectious uveitis), choroiditis (in one embodiment multifocal choroiditis), ocular histoplasmosis, blepharitis, dry eye, traumatic eye injury, Sjögren's disease, and other ophthalmic diseases wherein the disease or disease is associated with ocular neovascularization, vascular leakage, and/or retinal edema or retinal atrophy. In one embodiment the ocular disease is selected from AMD (in one embodiment wet AMD, dry AMD, intermediate AMD, advanced AMD, and geographic atrophy (GA)), macular degeneration, macular edema, DME (in one embodiment focal, non-center DME and diffuse, center-involved DME), retinopathy, diabetic retinopathy (DR) (in one embodiment proliferative DR (PDR), non-proliferative DR (NPDR), and high-altitude DR.

In a further aspect, the invention provides for the use of an antibody that binds to human VEGF-A and human ANG2 in the manufacture or preparation of a medicament. In one aspect, the medicament is for treatment of a vascular disease. In a further aspect, the medicament is for use in a method of treating a vascular disease comprising administering to an individual having a vascular disease an effective amount of the medicament. In one such aspect, the method further comprises administering to the individual an effective amount of at least one additional therapeutic agent, e.g., as described below.

In one aspect, the medicament is for treatment of an ocular disease. In a further aspect, the medicament is for use in a method of treating an ocular disease comprising administering to an individual having an ocular disease an effective amount of the medicament. In one such aspect, the method further comprises administering to the individual an effective amount of at least one additional therapeutic agent, e.g., as described below.

In a further aspect, the invention provides a method for treating a vascular disease. In one aspect, the method comprises administering to an individual having such vascular disease an effective amount of an antibody that binds to human VEGF-A and human ANG2. In one such aspect, the method further comprises administering to the individual an effective amount of at least one additional therapeutic agent, as described below.

In a further aspect, the invention provides a method for treating an ocular disease. In one aspect, the method comprises administering to an individual having such ocular disease an effective amount of an antibody that binds to human VEGF-A and human ANG2. In one such aspect, the method further comprises administering to the individual an effective amount of at least one additional therapeutic agent, as described below.

An "individual" according to any of the above aspects may be a human.

In a further aspect, the invention provides pharmaceutical compositions comprising any of the antibodies that bind to human VEGF-A and human ANG2 provided herein, e.g., for use in any of the above therapeutic methods. In one aspect, a pharmaceutical composition comprises any of the antibodies that bind to human VEGF-A and human ANG2 provided herein and a pharmaceutically acceptable carrier. In another aspect, a pharmaceutical composition comprises any of the antibodies that bind to human VEGF-A and human ANG2 provided herein and at least one additional therapeutic agent, e.g., as described below.

The antibody of the invention may be administered by intravitreal administration (e.g., intravitreal injection) or using a port delivery device. In one embodiment the antibody of the invention is administered using a port delivery device over a period of six months or more, in one embodiment 8 months or more, in one embodiment 9 months or more, in one embodiment 12 months or more, before the port delivery device is refilled. In one embodiment the antibody of the invention is administered using a port delivery device, wherein the antibody is applied into the port delivery device at a concentration of 150 mg/ml or more, in one embodiment at a concentration of 200 mg/ml or more.

Antibodies of the invention can be administered alone or used in a combination therapy. For instance, the combination therapy includes administering an antibody of the invention and administering at least one additional therapeutic agent (e.g. one, two, three, four, five, or six additional therapeutic agents).

In certain embodiments according to (or as applied to) any of the embodiments above, the ocular disorder is an intraocular neovascular disease selected from the group consisting of proliferative retinopathies, choroidal neovascularization (CNV), age-related macular degeneration (AMD), diabetic and other ischemia-related retinopathies, diabetic macular edema, pathological myopia, von Hippel-Lindau disease, histoplasmosis of the eye, retinal vein occlusion (RVO), including CRVO and BRVO, corneal neovascularization, retinal neovascularization, and retinopathy of prematurity (ROP).

In some instances, an antibody that binds to human VEGF-A and human ANG2 provided herein may be administered in combination with at least one additional therapeutic agent for treatment of an ocular disorder, for example, an ocular disorder described herein (e.g., AMD (e.g., wet AMD), DME, DR, RVO, or GA).

Any suitable AMD therapeutic agent can be administered as an additional therapeutic agent in combination with an antibody that binds to human VEGF and human ANG2 as provided herein for treatment of an ocular disorder (e.g., AMD, DME, DR, RVO, or GA), including, but not limited to, a VEGF antagonist, for example, an anti-VEGF antibody (e.g., LUCENTIS® (ranibizumab), RTH-258 (formerly ESBA-1008, an anti-VEGF single-chain antibody fragment; Novartis), or a bispecific anti-VEGF antibody (e.g., an anti-VEGF/anti-angiopoeitin 2 bispecific antibody such as faricimab; Roche)), a soluble VEGF receptor fusion protein (e.g., EYLEA® (aflibercept)), an anti-VEGF DARPin® (e.g., abicipar pegol; Molecular Partners AG/Allergan), or an anti-VEGF aptamer (e.g., MACUGEN® (pegaptanib sodium)); a platelet-derived growth factor (PDGF) antagonist, for example, an anti-PDGF antibody, an anti-PDGFR antibody (e.g., REGN2176-3), an anti-PDGF-BB pegylated aptamer (e.g., FOVISTA®; Ophthotech/Novartis), a soluble PDGFR receptor fusion protein, or a dual PDGF/VEGF antagonist (e.g., a small molecule inhibitor (e.g., DE-120 (Santen) or X-82 (TyrogeneX)) or a bispecific anti-PDGF/anti-VEGF antibody)); VISUDYNE® (verteporfin) in combination with photodynamic therapy; an antioxidant; a complement system antagonist, for example, a complement factor C5 antagonist (e.g., a small molecule inhitor (e.g., ARC-1905; Opthotech) or an anti-C5 antibody (e.g., LFG-316; Novartis), a properdin antagonist (e.g., an anti-properdin antibody, e.g., CLG-561; Alcon), or a complement factor D antagonist (e.g., an anti-complement factor D antibody, e.g., lampalizumab; Roche)); a C3 blocking peptide (e.g., APL-2, Appellis); a visual cycle modifier (e.g., emixustat hydrochloride); squalamine (e.g., OHR-102; Ohr Pharmaceutical); vitamin and mineral supplements (e.g., those described in the Age-Related Eye Disease Study 1 (AREDS1; zinc and/or antioxidants) and Study 2 (AREDS2; zinc, antioxidants, lutein, zeaxanthin, and/or omega-3 fatty acids)); a cell-based therapy, for example, NT-501 (Renexus); PH-05206388 (Pfizer), huCNS-SC cell transplantation (StemCells), CNTO-2476 (umbilical cord stem cell line; Janssen), OpRegen® (suspension of RPE cells; Cell Cure Neurosciences), or MA09-hRPE cell transplantation (Ocata Therapeutics); a tissue factor antagonist (e.g., hI-con1; Iconic Therapeutics); an alpha-adrenergic receptor agonist (e.g., brimonidine tartrate; Allergan); a peptide vaccine (e.g., S-646240; Shionogi); an amyloid beta antagonist (e.g., an anti-beta amyloid monoclonal antibody, e.g., GSK-933776); an SP antagonist (e.g., an anti-S1P antibody, e.g., iSONEP™; Lpath Inc); a ROBO4 antagonist (e.g., an anti-ROBO4 antibody, e.g., DS-7080a; Daiichi Sankyo); a lentiviral vector expressing endostatin and angiostatin (e.g., RetinoStat); and any combination thereof. In some instances, AMD therapeutic agents (including any of the preceding AMD therapeutic agents) can be co-formulated. For example, the anti-PDGFR antibody REGN2176-3 can be co-formulated with aflibercept (EYLEA®). In some instances, such a co-formulation can be administered in combination with an antibody that binds to human VEGF and human ANG2 of the invention. In some instances, the ocular disorder is AMD (e.g., wet AMD).

Any suitable DME and/or DR therapeutic agent can be administered in combination with an antibody that binds to human VEGF and human ANG2 of the invention for treatment of an ocular disorder (e.g., AMD, DME, DR, RVO, or GA), including, but not limited, to a VEGF antagonist (e.g., LUCENTIS® or EYLEA®), a corticosteroid (e.g., a corticosteroid implant (e.g., OZURDEX® (dexamethasone intravitreal implant) or ILUVIEN® (fluocinolone acetonide intravitreal implant)) or a corticosteroid formulated for administration by intravitreal injection (e.g., triamcinolone acetonide)), or combinations thereof. In some instances, the ocular disorder is DME and/or DR.

An antibody that binds to human VEGF and human ANG2 as provided herein may be administered in combination with a therapy or surgical procedure for treatment of an ocular disorder (e.g., AMD, DME, DR, RVO, or GA), including, for example, laser photocoagulation (e.g., panretinal photocoagulation (PRP)), drusen lasering, macular hole surgery, macular translocation surgery, implantable miniature telescopes, PHI-motion angiography (also known as micro-laser therapy and feeder vessel treatment), proton beam therapy, microstimulation therapy, retinal detachment and vitreous surgery, scleral buckle, submacular surgery, transpupillary thermotherapy, photosystem I therapy, use of RNA interference (RNAi), extracorporeal rheopheresis (also known as membrane differential filtration and rheotherapy), microchip implantation, stem cell therapy, gene replacement therapy, ribozyme gene therapy (including gene therapy for hypoxia response element, Oxford Biomedica; Lentipak™, Genetix; and PDEF gene therapy, GenVec), photoreceptor/retinal cells transplantation (including transplantable retinal epithelial cells, Diacrin, Inc.; retinal cell transplant, e.g., Astellas Pharma US, Inc., ReNeuron, CHA Biotech), acupuncture, and combinations thereof.

Such combination therapies noted above encompass combined administration (where two or more therapeutic agents are included in the same or separate formulations), and separate administration, in which case, administration of the antibody that binds to human VEGF and human ANG2 of the invention can occur prior to, simultaneously, and/or following, administration of the additional therapeutic agent or agents. In one embodiment, administration of the antibody that binds to human VEGF and human ANG2 of the invention and administration of an additional therapeutic agent occur within about one, two, three, four, or five months, or within about one, two or three weeks, or within about one, two, three, four, five, or six days, of each other.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g., by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the pharmaceutical composition, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 μg/kg to 15 mg/kg (e.g., 0.1 mg/kg-10 mg/kg) of antibody can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g., every week or every three weeks (e.g., such that the patient receives from about two to about twenty, or, e.g., about six doses of the antibody). An initial higher loading dose, followed by one or more lower doses may be administered. The progress of this therapy is easily monitored by conventional techniques and assays.

E. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, vials, syringes, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice.

Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this aspect of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

F. Devices

The antibody of the invention may be administered into the eye using an ocular implant, in one embodiment using a port delivery device.

A port delivery device is an implantable, refillable device that can release a therapeutic agent (e.g., an antibody of the invention) over a period of months (e.g., 1, 2, 3, 4, 5, 6, 7, 8, 9, 10, 11, 12, or more months). Exemplary port delivery devices that may be used include those from ForSight Labs, LLC and/or ForSight VISION4, for example, as described in International Patent Application Publication Nos. WO 2010/088548, WO2015/085234, WO 2013/116061, WO 2012/019176, WO 2013/040247, and WO 2012/019047, which are incorporated herein by reference in their entirety.

For example, the invention provides port delivery devices that include reservoirs containing any of the antibodies described herein. The port delivery device may further include a proximal region, a tubular body coupled to the proximal region in fluid communication with the reservoir, and one or more outlets in fluid communication with the reservoir and configured to release the composition into the eye. The tubular body may have an outer diameter configured to be inserted through an incision or opening in the eye of about 0.5 mm or smaller. The device may be about 1 mm to about 15 mm in length (e.g., about 1 mm, about 2 mm, about 4 mm, about 5 mm, about 6 mm, about 7 mm, about 9 mm, about 11 mm, about 13 mm, or about 15 mm in length). The reservoir may have any suitable volume. In some instances, the reservoir has a volume of about 1 µl to about 100 µl (e.g., about 1 µl, about 5 µl, about 10 µl, about 20 µl, about 50 µl, about 75 µl, or about 100 µl). The device or its constituent parts may be made of any suitable material, for example, polyimide.

In some instances, the port delivery device includes a reservoir containing any of the antibodies described herein and one or more additional compounds.

In some instances, the port delivery device includes any of the antibodies or antibody conjugates described herein and an additional VEGF antagonist.

3. Specific Embodiments of the Invention

In the following specific embodiments of the invention are listed.

1. An antibody that binds to human VEGF-A and to human ANG2, comprising a VEGF-A paratope and an ANG2 paratope within one cognate pair of a variable light chain domain (VL domain) and a variable heavy chain domain (VH domain), wherein the VEGF-A paratope comprises amino acid residues from CDR-H2, CDR-L1 and CDR-L3 of the antibody, wherein the ANG2 paratope comprises amino acid residues from the CDR-H1, CDR-H3 and CDR-L2 of the antibody.

2. An antibody that binds to human VEGF-A and to human ANG2, comprising a VEGF-A paratope and an ANG2 paratope within one cognate pair of a variable light chain domain (VL domain) and a variable heavy chain domain (VH domain), wherein the pair of the variable light chain domain and the variable heavy chain domain simultaneously binds to human VEGF-A and human ANG2.

3. An antibody that binds to human VEGF-A and to human ANG2, comprising a VEGF-A paratope and an ANG2 paratope within one cognate pair of a variable light chain domain (VL domain) and a variable heavy chain domain (VH domain), wherein the antibody binds to the same epitope on human VEGF-A and to the same epitope on human ANG2 as an antibody with a variable heavy chain domain of SEQ ID NO: 19 and a variable light chain domain of SEQ ID NO: 20.

4. An antibody that binds to human VEGF-A and to human ANG2, comprising a VEGF-A paratope and an ANG2 paratope within one cognate pair of a variable light chain domain (VL domain) and a variable heavy chain domain (VH domain), wherein the VEGF-A paratope comprises amino acid residues from CDR-H2, CDR-L1 and CDR-L3 of the antibody, wherein the ANG2 paratope comprises amino acid residues from the CDR-H1, CDR-H3 and CDR-L2 of the antibody; and/or the pair of the variable light chain domain and the variable heavy chain domain simultaneously binds to human VEGF-A and human ANG2; and/or the antibody binds to the same epitope on human VEGF-A and to the same epitope on human ANG2 as an antibody with a variable heavy chain domain of SEQ ID NO: 19 and a variable light chain domain SEQ ID NO: 20; and/or an antibody Fab fragment of the antibody binds (i) to human VEGF-A121 with a $K_D$ of less than 50 pM as measured by KinExA®, and (ii) to human ANG2 with a $K_D$ of less than 50 pM as measured by KinExA®; and/or an antibody Fab fragment of the antibody exhibits an aggregation onset temperature of 70° C. and more; and/or an antibody Fab fragment of the antibody exhibits a melting temperature of more than 80° C. as measured by dynamic light scattering; and/or a 20 mM His/HisHCl, pH 6.0 solution comprising 180 mg/ml of the antibody Fab fragment has a viscosity of less than 20 cP at 20° C. as detected by dynamic light scattering with a latex-bead DLS method as described in Example 8.

5. The antibody of one of one of the preceding embodiments, wherein the antibody comprises a VH domain comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, and a VL domain comprising (d) CDR-L1 comprising the amino acid sequence of SEQ ID NO:22, (e) CDR-L2 comprising the amino acid sequence of SEQ ID NO:23, and (f) CDR-L3 comprising the amino acid sequence of SEQ ID NO:8.

6. An antibody that binds to human VEGF-A and to human ANG2, wherein the antibody comprises a VH domain comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, and a VL domain comprising (d) CDR-L1 comprising the amino acid sequence of SEQ ID NO:22, (e) CDR-L2 comprising the amino acid sequence of SEQ ID NO:23, and (f) CDR-L3 comprising the amino acid sequence of SEQ ID NO:8.

7. The antibody of one of the preceding embodiments, wherein the antibody comprises a VH domain comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, (d) a human heavy chain framework with (i) FR1 comprising amino acid residues H3, D26, F27, E29, and Y30, (ii) FR3 comprising amino acid residues R66 and R94; and a VL domain comprising (e) CDR-L1 comprising the amino acid sequence of SEQ ID NO:22, (f) CDR-L2 comprising the amino acid sequence of SEQ ID NO:23, (g) CDR-L3 comprising the amino acid sequence of SEQ ID NO:8, and (h) a human light chain framework with (i) FR1 comprising amino acid residues I2 and Y3, (ii) FR2 comprising amino acid residues L46 and F49, (iii) FR3 comprising amino acid residue E57, wherein the numbering of the VH and VL domains is according to the Kabat numbering system.

8. An antibody that binds to human VEGF-A and to human ANG2, wherein the antibody comprises a VH domain comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, (d) a human heavy chain framework with (i) FR1 comprising amino acid residues H3, D26, F27, E29, and Y30, (ii) FR3 comprising amino acid residues R66 and R94; and a VL domain comprising (e) CDR-L1 comprising the amino acid sequence of SEQ ID NO:22, (f) CDR-L2 comprising the amino acid sequence of SEQ ID NO:23, (g) CDR-L3 comprising the amino acid sequence of SEQ ID NO:8, and (h) a human light chain framework with (i) FR1 comprising amino acid residues I2 and Y3, (ii) FR2 comprising amino acid residues L46 and F49, (iii) FR3 comprising amino acid residue E57, wherein the numbering of the VH and VL domains is according to the Kabat numbering system.

9. The antibody of one of the preceding embodiments, comprising a VH domain comprising amino acid residues H3, D26, F27, E29, Y30, D35b, D35c, D55, H56, K57, Y58, T61, K62, F63, 164, G65, R66, R94, D95, V96, F98, and F99, and a VL domain comprising amino acid residues I2, Y3, Y27, W27a, E32, L46, F49, D50, F53, K54, V55, Y56, E57, Y91, R92, Y93, H94, and P95, wherein the numbering of the VH and VL domains is according to the Kabat numbering system.

10. An antibody that binds to human VEGF-A and to human ANG2, wherein the antibody comprises the amino acid residues comprised in the VEGF-A paratope and in the ANG2 paratope of an antibody having a VH domain of SEQ ID NO:19 and a VL domain of SEQ ID NO:20.

11. The antibody of embodiment 9 or 10, comprising
a VEGF-A paratope comprising the following amino acid residues in the VH domain D35c, D55, H56, K57, Y58, T61, K62, F63, 164, G65, R66, and D95, and the following amino acid residues in the VL domain I2, Y3, Y27, W27a, E32, R92, Y93, H94, and P95; and
an ANG2 paratope comprising the following amino acid residues in the VH domain H3, D26, F27, E29, Y30, D35b, R94, V96, F98, and F99, and the following amino acid residues in the VL domain E32, L46, F49, D50, F53, K54, V55, Y56, E57, and Y91.

12. An antibody that binds to human VEGF-A and to human ANG2, comprising a VH domain comprising amino acid residues H3, D26, F27, E29, Y30, D35b, D35c, D55, H56, K57, Y58, T61, K62, F63, 164, G65, R66, R94, D95, V96, F98, and F99, and a VL domain comprising amino acid residues I2, Y3, Y27, W27a, E32, L46, F49, D50, F53, K54, V55, Y56, E57, Y91, R92, Y93, H94, and P95, wherein the numbering of the VH and VL domains is according to the Kabat numbering system.

13. The antibody of embodiment 12, comprising
a VEGF-A paratope comprising the following amino acid residues in the VH domain D35c, D55, H56, K57, Y58, T61, K62, F63, 164, G65, R66, and D95, and the following amino acid residues in the VL domain I2, Y3, Y27, W27a, E32, R92, Y93, H94, and P95; and
an ANG2 paratope comprising the following amino acid residues in the VH domain H3, D26, F27, E29, Y30, D35b, R94, V96, F98, and F99, and the following amino acid residues in the VL domain E32, L46, F49, D50, F53, K54, V55, Y56, E57, and Y91.

14. The antibody of any one of the preceding embodiments, comprising (a) a VH domain comprising an amino acid sequence having at least 90% sequence identity to the amino acid sequence of SEQ ID NO:19; and (b) a VL domain comprising an amino acid sequence having at least 90% sequence identity to the amino acid sequence of SEQ ID NO:20.

15. The antibody of any one of the preceding embodiments, comprising (a) a VH domain comprising an amino acid sequence having at least 90% sequence identity to the amino acid sequence of SEQ ID NO:19, wherein the VH domain comprises amino acid residues H3, D26, F27, E29, Y30, D35b, D35c, D55, H56, K57, Y58, T61, K62, F63, 164, G65, R66, R94, D95, V96, F98, and F99; and (b) a VL domain comprising an amino acid sequence having at least 90% sequence identity to the amino acid sequence of SEQ ID NO:20, wherein the VL domain comprises amino acid residues I2, Y3, Y27, W27a, E32, L46, F49, D50, F53, K54, V55, Y56, E57, Y91, R92, Y93, H94, and P95, wherein the numbering of the VH and VL domains is according to the Kabat numbering system.

16. An antibody that specifically binds to human VEGF-A and to human ANG2, wherein the antibody comprises a VH domain comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, and a VL domain comprising (d) CDR-L1 comprising the amino acid sequence of SEQ ID NO:22, (e) CDR-L2 comprising the amino acid sequence of SEQ ID NO:23, and (f) CDR-L3 comprising the amino acid sequence of SEQ ID NO:8, comprising (a) a VH domain comprising an amino acid sequence having at least 90% sequence identity to the amino acid sequence of SEQ ID NO:19; and (b) a VL domain comprising an amino acid sequence having at least 90% sequence identity to the amino acid sequence of SEQ ID NO:20.

17. An antibody that specifically binds to human VEGF-A and to human ANG2, wherein the antibody comprises a VH domain comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, and a VL domain comprising (d) CDR-L1 comprising the amino acid sequence of SEQ ID NO:22, (e) CDR-L2 comprising the amino acid sequence of SEQ ID NO:23, and (f) CDR-L3 comprising the amino acid sequence of SEQ ID NO:8, comprising (a) a VH domain comprising an amino acid sequence having at least 90% sequence identity to the amino acid sequence of SEQ ID NO:19, wherein the VH domain comprises amino acid residues H3, D26, F27, E29, Y30, R66 and R94; and (b) a VL domain comprising an amino acid sequence having at least 90% sequence identity to the amino acid sequence of SEQ ID NO:20, wherein the VL domain comprises amino acid residues I2, Y3, L46, F49, and E57, wherein the numbering of the VH and VL domains is according to the Kabat numbering system.

18. An antibody that specifically binds to human VEGF-A and to human ANG2, wherein the antibody comprises a VH domain comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, (d) a human heavy chain framework with (i) FR1 comprising amino acid residues H3, D26, F27, E29, and Y30, (ii) FR3 comprising amino acid residues R66 and R94; and a VL domain comprising (e) CDR-L1 comprising the amino acid sequence of SEQ ID NO:22, (f) CDR-L2 comprising the amino acid sequence of SEQ ID NO:23, (g) CDR-L3 comprising the amino acid sequence of SEQ ID NO:8, and (h) a human light chain framework with (i) FR1 comprising amino acid residues 12 and Y3, (ii) FR2 comprising amino acid residues L46 and F49, (iii) FR3 comprising amino acid residue E57, wherein the numbering of the VH and VL domains is according to the Kabat numbering system, comprising (a) a VH domain comprising an amino acid sequence having at least 90% sequence identity to the amino acid sequence of SEQ ID NO:19; and (b) a VL domain comprising an amino acid sequence having at least 90% sequence identity to the amino acid sequence of SEQ ID NO:20.

19. The antibody of any one of the preceding embodiments, comprising (a) a VH domain comprising an amino acid sequence of SEQ ID NO:19 with up to 15 amino acid substitutions; and (b) a variable light chain domain comprising an amino acid sequence of SEQ ID NO:20 with up to 15 amino acid substitutions.

20. The antibody of any one of the preceding embodiments, comprising (a) a VH domain comprising an amino acid sequence of SEQ ID NO:19 with up to 15 amino acid substitutions, wherein the amino acid substitutions are located at one or more of positions 1, 2, 4 to 25, 28, 35d to 54, 59, 60, 67 to 93, 97, 101 to 113 of SEQ ID NO:19; and (b) a variable light chain domain comprising an amino acid sequence of SEQ ID NO:20 with up to 15 amino acid substitutions, wherein the amino acid substitutions are located at positions 1, 4 to 26, 27b to 27d, 33 to 45, 47, 48, 51, 52, 58 to 90, 96 to 107 of SEQ ID NO:20, wherein the numbering of the VH and VL domains is according to the Kabat numbering system.

21. An antibody that specifically binds to human VEGF-A and to human ANG2, wherein the antibody comprises a VH domain comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, and a VL domain (d) CDR-L1 comprising the amino acid sequence of SEQ ID NO:22, (e) CDR-L2 comprising the amino acid sequence of SEQ ID NO:23, and (f) CDR-L3 comprising the amino acid sequence of SEQ ID NO:8, comprising (a) a VH domain comprising an amino acid sequence of SEQ ID NO:19 with up to 15 amino acid substitutions; and (b) a variable light chain domain comprising an amino acid sequence of SEQ ID NO:20 with up to 15 amino acid substitutions.

22. An antibody that specifically binds to human VEGF-A and to human ANG2, wherein the antibody comprises a VH domain comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, (d) a human heavy chain framework with (i) FR1 comprising amino acid residues H3, D26, F27, E29, and Y30, (ii) FR3 comprising amino acid residues R66 and R94; and a VL domain comprising (e) CDR-L1 comprising the amino acid sequence of SEQ ID NO:22, (f) CDR-L2 comprising the amino acid sequence of SEQ ID NO:23, (g) CDR-L3 comprising the amino acid sequence of SEQ ID NO:8, and (h) a human light chain framework with (i) FR1 comprising amino acid residues 12 and Y3, (ii) FR2 comprising amino acid residues L46 and F49, (iii) FR3 comprising amino acid residue E57, wherein the numbering of the VH and VL domains is according to the Kabat numbering system, and comprising (a) a VH domain comprising an amino acid sequence of SEQ ID NO:19 with up to 15 amino acid substitutions; and (b) a variable light chain domain comprising an amino acid sequence of SEQ ID NO:20 with up to 15 amino acid substitutions.

23. The antibody of any one of the preceding embodiments, comprising a VH sequence of SEQ ID NO:19 and a VL sequence of SEQ ID NO:20.

24. An antibody that binds to human VEGF-A and to human ANG2, comprising a VH sequence of SEQ ID NO:19 and a VL sequence of SEQ ID NO:20.

25. The antibody of any one of the preceding embodiments, comprising a heavy chain amino acid sequence of SEQ ID NO:24 and a light chain amino acid sequence of SEQ ID NO:25.

26. An antibody that binds to human VEGF-A and to human ANG2, comprising a heavy chain amino acid sequence of SEQ ID NO:24 and a light chain amino acid sequence of SEQ ID NO:25.

27. The antibody of any one of the preceding embodiments, comprising a heavy chain amino acid sequence of SEQ ID NO:17 and a light chain amino acid sequence of SEQ ID NO:18.

28. An antibody that specifically binds to human VEGF-A and to human ANG2, comprising a heavy chain amino acid sequence of SEQ ID NO:17 and a light chain amino acid sequence of SEQ ID NO:18.

29. The antibody of any one of the preceding embodiments, wherein an antibody Fab fragment of the antibody binds (i) to human VEGF-A121 with a $K_D$ of less than 50 pM as measured by KinExA®, and (ii) to human ANG2 with a $K_D$ of less than 50 pM as measured by KinExA®.

30. An antibody that specifically binds to human VEGF-A and to human ANG2 wherein an antibody Fab fragment of the antibody binds (i) to human VEGF-A121 with a $K_D$ of less than 50 pM as measured by KinExA®, and (ii) to human VEGF-A121 with a $K_D$ of less than 50 pM as measured by KinExA®.

31. An antibody that binds to human VEGF-A and to human ANG2, wherein the antibody comprises a VH domain comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, and a VL domain comprising (d) CDR-L1 comprising the amino acid sequence of SEQ ID NO:22, (e) CDR-L2 comprising the amino acid sequence of SEQ ID NO:23, and (f) CDR-L3 comprising the amino acid sequence of SEQ ID NO:8, wherein an antibody Fab fragment of the antibody binds (i) to human VEGF-A121 with a $K_D$ of less than 50 pM as measured by KinExA®, and (ii) to human ANG2 with a $K_D$ of less than 50 pM as measured by KinExA®.

32. An antibody that specifically binds to human VEGF-A and to human ANG2, wherein the antibody comprises a VH domain comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, (d) a human heavy chain framework with (i) FR1 comprising amino acid residues H3, D26, F27, E29, and Y30, (ii) FR3 comprising amino acid residues R66 and R94; and a VL domain comprising (e) CDR-L1 comprising the amino acid sequence of SEQ ID NO:22, (f) CDR-L2 comprising the amino acid sequence of SEQ ID NO:23, (g) CDR-L3 comprising the amino acid sequence of SEQ ID NO:8, and (h) a human light chain framework with (i) FR1 comprising amino acid residues 12 and Y3, (ii) FR2 comprising amino acid residues L46 and F49, (iii) FR3 comprising amino acid residue E57, wherein the numbering of the VH and VL domains is according to the Kabat numbering system, wherein an antibody Fab fragment of the antibody binds (i) to human VEGF-A121 with a $K_D$ of less than 50 pM as measured by KinExA®, and (ii) to human ANG2 with a $K_D$ of less than 50 pM as measured by KinExA®.

33. An antibody that specifically binds to human VEGF-A and to human ANG2, comprising within one pair of a VH and VL domain: (i) a VH domain comprising amino acid residues H3, D26, F27, E29, Y30, D35b, D35c, D55, H56, K57, Y58, T61, K62, F63, 164, G65, R66, R94, D95, V96, F98, and F99, and (ii) a VL domain comprising amino acid residues I2, Y3, Y27, W27a, E32, L46, F49, D50, F53, K54, V55, Y56, E57, Y91, R92, Y93, H94, and P95, wherein the numbering of the VH and VL domains is according to the Kabat numbering system, wherein an antibody Fab fragment of the antibody binds (i) to human VEGF-A121 with a $K_D$ of less than 50 pM as measured by KinExA®, and (ii) to human ANG2 with a $K_D$ of less than 50 pM as measured by KinExA®.

34. An antibody that specifically binds to human VEGF-A and to human ANG2, wherein the antibody comprises a VH domain comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, and a VL domain comprising (d) CDR-L1 comprising the amino acid sequence of SEQ ID NO:22, (e) CDR-L2 comprising the amino acid sequence of SEQ ID NO:23, and (f) CDR-L3 comprising the amino acid sequence of SEQ ID NO:8, comprising (a) a VH domain comprising an amino acid sequence having at least 90% sequence identity to the amino acid sequence of SEQ ID NO:19; and (b) a VL domain comprising an amino acid sequence having at least 90% sequence identity to the amino acid sequence of SEQ ID NO:20; wherein an antibody Fab fragment of the antibody binds (i) to human VEGF-A121 with a $K_D$ of less than 50 pM as measured by KinExA®, and (ii) to human ANG2 with a $K_D$ of less than 50 pM as measured by KinExA®.

35. The antibody of any one of the preceding embodiments, wherein an antibody Fab fragment of the antibody exhibits an aggregation onset temperature of 70° C. and more.

36. An antibody that specifically binds to human VEGF-A and to human ANG2, wherein an antibody Fab fragment of the antibody exhibits an aggregation onset temperature of 70° C. and more.

37. An antibody that binds to human VEGF-A and to human ANG2, wherein the antibody comprises a VH domain comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, and a VL domain comprising (d) CDR-L1 comprising the amino acid sequence of SEQ ID NO:22, (e) CDR-L2 comprising the amino acid sequence of SEQ ID NO:23, and (f) CDR-L3 comprising the amino acid sequence of SEQ ID NO:8, wherein an antibody Fab fragment of the antibody exhibits an aggregation onset temperature of 70° C. and more.

38. An antibody that specifically binds to human VEGF-A and to human ANG2, wherein the antibody comprises a VH domain comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, (d) a human heavy chain framework with (i) FR1 comprising amino acid residues H3, D26, F27, E29, and Y30, (ii) FR3 comprising amino acid residues R66 and R94; and a VL domain comprising (e) CDR-L1 comprising the amino acid sequence of SEQ ID NO:22, (f) CDR-L2 comprising the amino acid sequence of SEQ ID NO:23, (g) CDR-L3 comprising the amino acid sequence of SEQ ID NO:8, and (h) a human light chain framework with (i) FR1 comprising amino acid residues 12 and Y3, (ii) FR2 comprising amino acid residues L46 and F49, (iii) FR3 comprising amino acid residue E57, wherein the numbering of the VH and VL domains is according to the Kabat numbering system, wherein an antibody Fab fragment of the antibody exhibits an aggregation onset temperature of 70° C. and more.

39. An antibody that specifically binds to human VEGF-A and to human ANG2, comprising within one pair of a VH and VL domain: (i) a VH domain comprising amino acid residues H3, D26, F27, E29, Y30, D35b, D35c, D55, H56, K57, Y58, T61, K62, F63, 164, G65, R66, R94, D95, V96, F98, and F99, and (ii) a VL domain comprising amino acid residues I2, Y3, Y27, W27a, E32, L46, F49, D50, F53, K54, V55, Y56, E57, Y91, R92, Y93, H94, and P95, wherein the numbering of the VH and VL domains is according to the Kabat numbering system, wherein an antibody Fab fragment of the antibody exhibits an aggregation onset temperature of 70° C. and more.

40. An antibody that specifically binds to human VEGF-A and to human ANG2, wherein the antibody comprises a VH domain comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, and a VL domain comprising (d) CDR-L1 comprising the amino acid sequence of SEQ ID NO:22, (e) CDR-L2 comprising the amino acid sequence of SEQ ID NO:23, and (f) CDR-L3 comprising the amino acid sequence of SEQ ID NO:8, comprising (a) a VH domain comprising an amino acid sequence having at least 90% sequence identity to the amino acid sequence of SEQ ID NO:19; and (b) a VL domain comprising an amino acid sequence having at least 90% sequence identity to the amino acid sequence of SEQ ID NO:20; wherein an antibody Fab fragment of the antibody exhibits an aggregation onset temperature of 70° C. and more.

41. The antibody of any one of the preceding embodiments, wherein an antibody Fab fragment of the antibody exhibits a melting temperature of more than 80° C. as measured by dynamic light scattering.

42. An antibody that specifically binds to human VEGF-A and to human ANG2, wherein an antibody Fab fragment of the antibody exhibits a melting temperature of more than 80° C. as measured by dynamic light scattering.

43. An antibody that binds to human VEGF-A and to human ANG2, wherein the antibody comprises a VH domain comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, and a VL domain comprising (d) CDR-L1 comprising the amino acid sequence of SEQ ID NO:22, (e) CDR-L2 comprising the amino acid sequence of SEQ ID NO:23, and (f) CDR-L3 comprising the amino acid sequence of SEQ ID NO:8, wherein an antibody Fab fragment of the antibody exhibits a melting temperature of more than 80° C. as measured by dynamic light scattering.

44. An antibody that specifically binds to human VEGF-A and to human ANG2, wherein the antibody comprises a VH domain comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, (d) a human heavy chain framework with (i) FR1 comprising amino acid residues H3, D26, F27, E29, and Y30, (ii) FR3 comprising amino acid residues R66 and R94; and a VL domain comprising (e) CDR-L1 comprising the amino acid sequence of SEQ ID NO:22, (f) CDR-L2 comprising the amino acid sequence of SEQ ID NO:23, (g) CDR-L3 comprising the amino acid sequence of SEQ ID NO:8, and (h) a human light chain framework with (i) FR1 comprising amino acid residues I2 and Y3, (ii) FR2 comprising amino acid residues L46 and F49, (iii) FR3 comprising amino acid residue E57, wherein the numbering of the VH and VL domains is according to the Kabat numbering system, wherein an antibody Fab fragment of the antibody exhibits a melting temperature of more than 80° C. as measured by dynamic light scattering.

45. An antibody that specifically binds to human VEGF-A and to human ANG2, comprising within one pair of a VH and VL domain: (i) a VH domain comprising amino acid residues H3, D26, F27, E29, Y30, D35b, D35c, D55, H56, K57, Y58, T61, K62, F63, I64, G65, R66, R94, D95, V96, F98, and F99, and (ii) a VL domain comprising amino acid residues I2, Y3, Y27, W27a, E32, L46, F49, D50, F53, K54, V55, Y56, E57, Y91, R92, Y93, H94, and P95, wherein the numbering of the VH and VL domains is according to the Kabat numbering system, wherein an antibody Fab fragment of the antibody exhibits a melting temperature of more than 80° C. as measured by dynamic light scattering.

46. An antibody that specifically binds to human VEGF-A and to human ANG2, wherein the antibody comprises a VH domain comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, and a VL domain comprising (d) CDR-L1 comprising the amino acid sequence of SEQ ID NO:22, (e) CDR-L2 comprising the amino acid sequence of SEQ ID NO:23, and (f) CDR-L3 comprising the amino acid sequence of SEQ ID NO:8, comprising (a) a VH domain comprising an amino acid sequence having at least 90% sequence identity to the amino acid sequence of SEQ ID NO:19; and (b) a VL domain comprising an amino acid sequence having at least 90% sequence identity to the amino acid sequence of SEQ ID NO:20; wherein an antibody Fab fragment of the antibody exhibits a melting temperature of more than 80° C. as measured by dynamic light scattering.

47. The antibody of any one of the preceding embodiments, wherein a 20 mM His/HisHCl, pH 6.0 solution comprising 180 mg/ml of the antibody Fab fragment has a viscosity of less than 20 cP at 20° C. as detected by dynamic light scattering with a latex-bead DLS method as described in Example 8.

48. An antibody that specifically binds to human VEGF-A and to human ANG2, wherein a 20 mM His/HisHCl, pH 6.0 solution comprising 180 mg/ml of the antibody Fab fragment has a viscosity of less than 20 cP at 20° C. as detected by dynamic light scattering with a latex-bead DLS method as described in Example 8.

49. An antibody that binds to human VEGF-A and to human ANG2, wherein the antibody comprises a VH domain comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, and a VL domain comprising (d) CDR-L1 comprising the amino acid sequence of SEQ ID NO:22, (e) CDR-L2 comprising the amino acid sequence of SEQ ID NO:23, and (f) CDR-L3 comprising the amino acid sequence of SEQ ID NO:8, wherein a 20 mM His/HisHCl, pH 6.0 solution comprising 180 mg/ml of the antibody Fab fragment has a viscosity of less than 20 cP at 20° C. as detected by dynamic light scattering with a latex-bead DLS method as described in Example 8.

50. An antibody that specifically binds to human VEGF-A and to human ANG2, wherein the antibody comprises a VH domain comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, (d) a human heavy chain framework with (i) FR1 comprising amino acid residues H3, D26, F27, E29, and Y30, (ii) FR3 comprising amino acid residues R66 and R94; and a VL domain comprising (e)

CDR-L1 comprising the amino acid sequence of SEQ ID NO:22, (f) CDR-L2 comprising the amino acid sequence of SEQ ID NO:23, (g) CDR-L3 comprising the amino acid sequence of SEQ ID NO:8, and (h) a human light chain framework with (i) FR1 comprising amino acid residues I2 and Y3, (ii) FR2 comprising amino acid residues L46 and F49, (iii) FR3 comprising amino acid residue E57, wherein the numbering of the VH and VL domains is according to the Kabat numbering system, wherein a 20 mM His/HisHCl, pH 6.0 solution comprising 180 mg/ml of the antibody Fab fragment has a viscosity of less than 20 cP at 20° C. as detected by dynamic light scattering with a latex-bead DLS method as described in Example 8.

51. An antibody that specifically binds to human VEGF-A and to human ANG2, comprising within one pair of a VH and VL domain: (i) a VH domain comprising amino acid residues H3, D26, F27, E29, Y30, D35b, D35c, D55, H56, K57, Y58, T61, K62, F63, I64, G65, R66, R94, D95, V96, F98, and F99, and (ii) a VL domain comprising amino acid residues I2, Y3, Y27, W27a, E32, L46, F49, D50, F53, K54, V55, Y56, E57, Y91, R92, Y93, H94, and P95, wherein the numbering of the VH and VL domains is according to the Kabat numbering system, wherein a 20 mM His/HisHCl, pH 6.0 solution comprising 180 mg/ml of the antibody Fab fragment has a viscosity of less than 20 cP at 20° C. as detected by dynamic light scattering with a latex-bead DLS method as described in Example 8.

52. An antibody that specifically binds to human VEGF-A and to human ANG2, wherein the antibody comprises a VH domain comprising (a) CDR-H1 comprising the amino acid sequence of SEQ ID NO:3, (b) CDR-H2 comprising the amino acid sequence of SEQ ID NO:21, and (c) CDR-H3 comprising the amino acid sequence of SEQ ID NO:14, and a VL domain comprising (d) CDR-L1 comprising the amino acid sequence of SEQ ID NO:22, (e) CDR-L2 comprising the amino acid sequence of SEQ ID NO:23, and (f) CDR-L3 comprising the amino acid sequence of SEQ ID NO:8, comprising (a) a VH domain comprising an amino acid sequence having at least 90% sequence identity to the amino acid sequence of SEQ ID NO:19; and (b) a VL domain comprising an amino acid sequence having at least 90% sequence identity to the amino acid sequence of SEQ ID NO:20; wherein a 20 mM His/HisHCl, pH 6.0 solution comprising 180 mg/ml of the antibody Fab fragment has a viscosity of less than 20 cP at 20° C. as detected by dynamic light scattering with a latex-bead DLS method as described in Example 8.

53. The antibody of any one of the preceding embodiments, which is a monoclonal antibody.
54. The antibody of any one of the preceding embodiments, which is an antibody fragment that binds to human VEGF-A and to human ANG2.
55. The antibody of any one of the preceding embodiments, wherein the antibody is bispecific.
56. The antibody of any one of the preceding embodiments, wherein the antibody is a Fab fragment.
57. The antibody of any one of the preceding embodiments, wherein the antibody is a bispecific antibody fragment.
58. The antibody of any one of the preceding embodiments, wherein the antibody is a multispecific antibody.
59. The antibody of any one of the preceding embodiments, wherein the antibody specifically binds to human VEGF-A.

60. The antibody of any one of the preceding embodiments, wherein the antibody specifically binds to human ANG2.
61. An isolated nucleic acid encoding the antibody of any of embodiments 1 to 58.
62. A host cell comprising the nucleic acid of embodiment 59.
63. An expression vector comprising the nucleic acid of embodiment 61.
64. A method of producing an antibody that binds to human VEGF-A and to human ANG2 comprising culturing the host cell of embodiment 60 so that the antibody is produced.
65. The method of embodiment 64, further comprising recovering the antibody from the host cell.
66. The method of embodiment 64 or 65, wherein the host cell is an *E. coli* cell.
67. The method of embodiment 64 or 65, wherein the host cell is a CHO cell.
68. An antibody produced by the method of embodiment 64 or 65.
69. A pharmaceutical formulation comprising the antibody of any one of embodiments 1 to 60 and a pharmaceutically acceptable carrier.
70. The antibody of any one of embodiments 1 to 60 for use as a medicament.
71. The antibody of any one of embodiments 1 to 60 for use in the treatment of a vascular disease.
72. The antibody of any one of embodiments 1 to 60 for use in the treatment of an ocular vascular disease.
73. Use of the antibody of any one of embodiments 1 to 60 or the pharmaceutical composition of embodiment 65 in the manufacture of a medicament.
74. Use of the antibody of any one of embodiments 1 to 60 or the pharmaceutical composition of embodiment 65 in the manufacture of a medicament for inhibiting angiogenesis.
75. A method of treating an individual having a vascular disease comprising administering to the individual an effective amount of the antibody of one of embodiments 1 to 60 or the pharmaceutical formulation of embodiment 69.
76. A method of treating an individual having an ocular vascular disease comprising administering to the individual an effective amount of the antibody of one of embodiments 1 to 60 or the pharmaceutical formulation of embodiment 69.
77. A method of inhibiting angiogenesis in an individual comprising administering to the individual an effective amount of the antibody of any of embodiments 1 to 60 or the pharmaceutical formulation of embodiment 69 to inhibit angiogenesis.
78. A port delivery device comprising the antibody of any of embodiments 1 to 60 or the pharmaceutical formulation of embodiment 69.
79. The antibody of any of embodiments 1 to 60 or the pharmaceutical formulation of embodiment 69 for ocular administration by a port delivery device.
80. The antibody of any of embodiments 1 to 60 or the pharmaceutical formulation of embodiment 69 for ocular administration by a port delivery device according to embodiment 79, wherein the administration is over a period of six months or more, in one embodiment 8 months or more, in one embodiment 9 months or more, before the port delivery device is refilled.
81. The of any of embodiments 1 to 60 or the pharmaceutical formulation of embodiment 69 for use as a medicament by administrating the antibody or the pharmaceutical formulation using a port delivery device, wherein the antibody is applied into the port delivery device at a concentration of 150 mg/ml or more, in one embodiment at a concentration of 200 mg/ml or more.

| DESCRIPTION OF THE AMINO ACID SEQUENCES | |
|---|---|
| SEQ ID NO: 1 | VH domain of P1AA8906<br>DFQLVESGGGLVKPGGSLRLSCAASYEFEYDDMSWVRQAPGKGL<br>EWVGSISPKGGSTYYNTKFIGRFTISRDNSKNTLYLQMNSLRAE<br>DTAVYYCARDVGFFDMWGQGTLVTVSS |
| SEQ ID NO: 2 | VL domain of P1AA8906<br>AIYMHQEPSSLSASVGDRVTITCHGSYWLSNYLAWYQQKPGKAP<br>KLLIFDARWLVHGVPSRFSGSGSHEDYTLTISSLQPEDFATYYC<br>QQYRYHPYTFGHGTKVEIK |
| SEQ ID NO: 3 | H-CDR1 of P1AA8906, P1AA0902 and P1AD9820<br>DDMS |
| SEQ ID NO: 4 | H-CDR2 of P1AA8906<br>SISPKGGSTYYNTKFIG |
| SEQ ID NO: 5 | H-CDR3 of P1AA8906<br>DVGFFDM |
| SEQ ID NO: 6 | L-CDR1 of P1AA8906<br>HGSYWLSNYLA |
| SEQ ID NO: 7 | L-CDR2 of P1AA8906<br>DARWLVH |
| SEQ ID NO: 8 | L-CDR3 of P1AA8906, P1AA0902 and P1AD9820<br>QQYRYHPYT |
| SEQ ID NO: 9 | heavy chain of P1AA8906 Fab fragment<br>DFQLVESGGGLVKPGGSLRLSCAASYEFEYDDMSWVRQAPGKGL<br>EWVGSISPKGGSTYYNTKFIGRFTISRDNSKNTLYLQMNSLRAE<br>DTAVYYCARDVGFFDMWGQGTLVTVSSASTKGPSVFPLAPSSKS<br>TSGGTAALGCLVKDYFPEPVTVSWNSGALTSGVHTFPAVLQSSG<br>LYSLSSVVTVPSSSLGTKTYICNVNHKPSNTKVDKKVEPKSCDK<br>THT |
| SEQ ID NO: 10 | light chain of P1AA8906 Fab fragment<br>AIYMHQEPSSLSASVGDRVTITCHGSYWLSNYLAWYQQKPGKAP<br>KLLIFDARWLVHGVPSRFSGSGSHEDYTLTISSLQPEDFATYYC<br>QQYRYHPYTFGHGTKVEIKRTVAAPSVFIFPPSDEQLKSGTASV<br>VCLLNNFYPREAKVQWKVDNALQSGNSQESVTEQDSKDSTYSLS<br>STLTLSKADYEKHKVYACEVTHQGLSSPVTKSFNRGEC |
| SEQ ID NO: 11 | VH domain of P1AA0902<br>DDHLVESGGGLVKPGGSLRLSCATADFFEYDDMSWVRQAPGKGL<br>EWVGSISGRGDHKYLNTKFIGRFTISRDDSKNTLYLQMNSLRAE<br>DTAVYYCARDVGFFDWWGQGTLVTVSS |
| SEQ ID NO: 12 | VL domain of P1AA0902<br>AIYMHQEPSSLSASVGDRVTITCHGSYWLNSELAWYQQKPGKAP<br>KLLIFDGDFKVFDVPSRFSGSGSHEDYTLTISSLQPEDFATYYC<br>QQYRYHPYTFGHGTKVEIK |
| SEQ ID NO: 13 | H-CDR2 of P1AA0902<br>SISGRGDHKYLNTKFIG |
| SEQ ID NO: 14 | H-CDR3 of P1AA0902 and P1AD9820<br>DVGFFDW |
| SEQ ID NO: 15 | L-CDR1 of P1AA0902<br>HGSYWLNSELA |
| SEQ ID NO: 16 | L-CDR2 of P1AA0902<br>DGDFKVF |
| SEQ ID NO: 17 | heavy chain of P1AA0902 Fab fragment<br>DDHLVESGGGLVKPGGSLRLSCATADFFEYDDMSWVRQAPGKGL<br>EWVGSISGRGDHKYLNTKFIGRFTISRDDSKNTLYLQMNSLRAE<br>DTAVYYCARDVGFFDWWGQGTLVTVSSASTKGPSVFPLAPSSKS<br>TSGGTAALGCLVKDYFPEPVTVSWNSGALTSGVHTFPAVLQSSG<br>LYSLSSVVTVPSSSLGTKTYICNVNHKPSNTKVDKKVEPKSCDK<br>THT |
| SEQ ID NO: 18 | light chain of P1AA0902 Fab fragment<br>AIYMHQEPSSLSASVGDRVTITCHGSYWLNSELAWYQQKPGKAP<br>KLLIFDGDFKVFDVPSRFSGSGSHEDYTLTISSLQPEDFATYYC<br>QQYRYHPYTFGHGTKVEIKRTVAAPSVFIFPPSDEQLKSGTASV<br>VCLLNNFYPREAKVQWKVDNALQSGNSQESVTEQDSKDSTYSLS<br>STLTLSKADYEKHKVYACEVTHQGLSSPVTKSFNRGEC |
| SEQ ID NO: 19 | VH domain of P1AD9820<br>SEHLVESGGGLVKPGGSLRLSCATADFFEYDDMSWVRQAPGKGL<br>EWVGSISPKGDHKYLNTKFIGRFTISRDDSKNTLYLQMNSLRAE<br>DTAVYYCARDVGFFDWWGQGTLVTVSS |
| SEQ ID NO: 20 | VL domain of P1AD9820<br>AIYMHQEPSSLSASVGDRVTITCHGSYWLNSEVAWYQQKPGKAP<br>KLLIFDGDFKVYEVPSRFSGSGSHEDYTLTISSLQPEDFATYYC<br>QQYRYHPYTFGHGTKVEIK |
| SEQ ID NO: 21 | H-CDR2 of P1AD9820<br>SISPKGDHKYLNTKFIG |
| SEQ ID NO: 22 | L-CDR1 of P1AD9820<br>HGSYWLNSEVA |

-continued

| DESCRIPTION OF THE AMINO ACID SEQUENCES |
| --- |

SEQ ID NO: 23  L-CDR2 of P1AD9820
DGDFKVY

SEQ ID NO: 24  heavy chain of P1AD9820 Fab fragment
SEHLVESGGGLVKPGGSLRLSCATADFFEYDDMSWVRQAPGKGL
EWVGSISPKGDHKYLNTKFIGRFTISRDDSKNTLYLQMNSLRAE
DTAVYYCARDVGFFDWWGQGTLVTVSSASTKGPSVFPLAPSSKS
TSGGTAALGCLVKDYFPEPVTVSWNSGALTSGVHTFPAVLQSSG
LYSLSSVVTVPSSSLGTQTYICNVNHKPSNTKVDKKVEPKSCDK
THT SEQ ID NO: 25  light chain of P1AD9820 Fab fragment
AIYMHQEPSSLSASVGDRVTITCHGSYWLNSEVAWYQQKPGKAP
KLLIFDGDFKVYEVPSRFSGSGSHEDYTLTISSLQPEDFATYYC
QQYRYHPYTFGHGTKVEIKRTVAAPSVFIFPPSDEQLKSGTASV
VCLLNNFYPREAKVQWKVDNALQSGNSQESVTEQDSKDSTYSLS
STLTLSKADYEKHKVYACEVTHQGLSSPVTKSFNRGEC SEQ ID NO: 26  human VEGF
MNFLLSWVHWSLALLLYLHHAKWSQAAPMAEGGGQNHHEVVKFM
DVYQRSYCHPIETLVDIFQEYPDEIEYIFKPSCVPLMRCGGCCN
DEGLECVPTEESNITMQIMRIKPHQGQHIGEMSFLQHNKCECRP
KKDRARQEKKSVRGKGKGQKRKRKKSRYKSWSVYVGARCCLMPW
SLPGPHPCGPCSERRKHLFVQDPQTCKCSCKNTDSRCKARQLEL
NERTCRCDKPRR SEQ ID NO: 27  human ANG2
MWQIVFFTLSCDLVLAAAYNNFRKSMDSIGKKQYQVQHGSCSYT
FLLPEMDNCRSSSSPYVSNAVQRDAPLEYDDSVQRLQVLENIME
NNTQWLMKLENYIQDNMKKEMVEIQQNAVQNQTAVMIEIGTNLL
NQTAEQTRKLTDVEAQVLNQTTRLELQLLEHSLSTNKLEKQILD
QTSEINKLQDKNSFLEKKVLAMEDKHIIQLQSIKEEKDQLQVLV
SKQNSIIEELEKKIVTATVNNSVLQKQQHDLMETVNNLLTMMST
SNSAKDPTVAKEEQISFRDCAEVFKSGHTTNGIYTLTFPNSTEE
IKAYCDMEAGGGGWTIIQRREDGSVDFQRTWKEYKVGFGNPSGE
YWLGNEFVSQLTNQQRYVLKIHLKDWEGNEAYSLYEHFYLSSEE
LNYRIHLKGLTGTAGKISSISQPGNDFSTKDGDNDKCICKCSQM
LTGGWWFDACGPSNLNGMYYPQRQNTNKFNGIKWYYWKGSGYSL
KATTMMIRPADF SEQ ID NO: 28  human VEGFA-121
MNFLLSWVHWSLALLLYLHHAKWSQAAPMAEGGGQNHHEVVKFM
DVYQRSYCHPIETLVDIFQEYPDEIEYIFKPSCVPLMRCGGCCN
DEGLECVPTEESNITMQIMRIKPHQGQHIGEMSFLQHNKCECRP
KKDRARQEKCDKPRR SEQ ID NO: 29  Nesvacumab LC
IVLTQSPGTLSLSPGERATLSCRASQSVSSTYLAWYQQKPGQAP
RLLIYGASSRATGIPDRFSGSGSGTDFTLTISRLEPEDFAVYYC
QHYDNSQTFGQGTKVEIKRTVAAPSVFIFPPSDEQLKSGTASVV
CLLNNFYPREAKVQWKVDNALQSGNSQESVTEQDSKDSTYSLSS
TLTLSKADYEKHKVYACEVTHQGLSSPVTKSFNRGEC SEQ ID NO: 30  Nesvacumab HC
AVQLVASGGGLVQPGGSLRLSCAASGFTFSSYDIHWVRQATGKG
LEWVSAIGPAGDTYYPGSVKGRFTISRENAKNSLYLQMNSLRAG
DTAVYYCARGLITFGGLIAPFDYWGQGTLVTVSSASTKGPSVFP
LAPSSKSTSGGTAALGCLVKDYFPEPVTVSWNSGALTSGVHTFP
AVLQSSGLYSLSSVVTVPSSSLGTQTYICNVNHKPSNTKVDKKV
EPKSCDKTHTCPPCPAPEAAGGPSVFLFPPKPKDTLMISRTPEV
TCVVVDVSHEDPEVKFNWYVDGVEVHNAKTKPREEQYNSTYRVV
SVLTVLHQDWLNGKEYKCKVSNKALGAPIEKTISKAKGQPREPQ
VYTLPPSRDELTKNQVSLTCLVKGFYPSDIAVEWESNGQPENNY
KTTPPVLDSDGSFFLYSKLTVDKSRWQQGNVFSCSVMHEALHNH
YTQKSLSLSPGK

EXAMPLES

The following examples are provided to aid the understanding of the present invention, the true scope of which is set forth in the appended claims. It is understood that modifications can be made in the procedures set forth without departing from the spirit of the invention.

Materials & General Methods

Human VEGF-A121 Affinity KinExA®:

Instrumentation and Materials:

A KinExA® 3200 instrument from Sapidyne Instruments (Boise, Id.) with autosampler was used. Polymethylmethacrylate (PMMA) beads were purchased from Sapidyne, the anti-VEGF antibodies were purchased from R&D Systems (Mab293, BAF293). Streptavidin Alexa Fluor™ 647 conjugate was purchased from Thermo Fisher scientific (S21374). PBS (phosphate buffered saline), BSA (bovine serum albumin fraction V), VEGFA-121 (SEQ ID NO:28) was prepared in-house (Roche).

Preparation of Antigen Coated Beads

PMMA beads were coated according to the KinExA® Handbook protocol (Adsorption coating, Sapidyne). First, 30 µg of Anti-VEGF-Antibody MAB293 (R&D) in 1 ml PBS (pH7.4) was added per vial (200 mg) of beads for adsorption coating. After rotating for 2 h at room temperature, the supernatant was removed and filled up with 1 ml of blocking solution (10 mg/ml BSA in buffer) and rock for 1 h.

KinExA® equilibrium assay

All KinExA® experiments were performed at room temperature (RT) using PBS pH 7.4 with 0.01% BSA and 0.01% Tween® 20 (BioRad, #161-0781) as running buffer. Samples and beads were prepared in LowCross-Buffer® (Candor Bioscience) to reduce the unspecific binding observed in previous measurements. A flow rate of 0.25 ml/min was used. A constant amount of VEGFA-121-His (50 pM and in a second experiment 500 pM) was titrated with the tested antibody by twofold serial dilution starting at 4 nM (concentration range 1.95 pM-4000 pM). Antigen-antibody complexes were incubated at RT for at least 8 h to allow equilibrium to be reached. Equilibrated mixtures were then drawn through a column of anti-VEGF antibody (Mab293) coupled beads in the KinExA® system at a volume of 750 µl for 50 pM constant VEGF and at a volume of 125 µl for 500 pM constant VEGF permitting unbound VEGFA-121 to be captured by the beads without perturbing the equilibrium state of the solution. Bound VEGFA-121 was detected using a second biotinylated anti-VEGF antibody (BAF293) with a concentration of 250 ng/ml and following by an injection of 250 ng/ml Streptavidin Alexa Fluor™ 647 conjugate in sample buffer. Each sample was measured in duplicates for all equilibrium experiments. The $K_D$ was obtained from non-linear regression analysis of the data using a one-site homogeneous binding model contained within the KinExA® software (Version 4.0.11) using the "standard analysis" method. The software calculates the $K_D$ and determines the 95% confidence interval by fitting the data points to a theoretical $K_D$ curve. The 95% confidence interval is given as $K_D$ low and $K_D$ high.

For the final $K_D$ determination a n-curve determination of the two measurements with different constant VEGFA-121 concentrations was done. The n-curve analysis may be used to analyze multiple standard $K_D$ experiments on the same axis to obtain a more accurate determination of the $K_D$.

Human ANG2 Affinity KinExA®:

Instrumentation and Materials

A KinExA® 3200 instrument from Sapidyne Instruments (Boise, Id.) with autosampler was used. Polymethylmethacrylate (PMMA) beads were purchased from Sapidyne, the anti-Ang2 antibodies were purchased from R&D Systems (MAB098, BAM0981). Streptavidin Alexa Fluor™ 647 conjugate was purchased from Thermo Fisher scientific (S21374). PBS (phosphate buffered saline), BSA (bovine serum albumin fraction V), Ang2 (SEQ ID NO: 27) was prepared in-house (Roche).

Preparation of Antigen Coated Beads

PMMA beads were coated according to the KinExA® Handbook protocol (Adsorption coating, Sapidyne). First, 20 µg of anti-Ang2-Antibody MAB098 (R&D) in 1 ml PBS (pH7.4) was added per vial (200 mg) of beads for adsorption coating. After rotating for 2 h at room temperature, the supernatant was removed and filled up with 1 ml of blocking solution (10 mg/ml BSA in buffer) and rock for 1 h.

KinExA® Equilibrium Assay

All KinExA® experiments were performed at room temperature (RT) using PBS pH 7.4 with 0.01% BSA and 0.01% Tween® 20 (BioRad, #161-0781) as running buffer. Samples and beads were prepared in LowCross-Buffer® (Candor Bioscience) to reduce the unspecific binding observed in previous measurements. A flow rate of 0.25 ml/min was used. A constant amount of Ang2-RBD-muFc (50 pM and in a second experiment 500 pM) was titrated with tested antibody by twofold serial dilution starting at 4 nM (concentration range 1.95 pM-4000 pM). Antigen-antibody complexes were incubated at RT for at least 8 h to allow equilibrium to be reached. Equilibrated mixtures were then drawn through a column of Anti-Ang2 antibody (MAB098) coupled beads in the KinExA® system at a volume of 750 µl for 50 pM constant Ang2 and at a volume of 188 µl for 500 pM constant Ang2 permitting unbound Ang2 to be captured by the beads without perturbing the equilibrium state of the solution. Bound Ang2 was detected using a second biotinylated anti-Ang2 antibody (BAM0981) with a concentration of 250 ng/ml and following by an injection of 250 ng/ml Streptavidin Alexa Fluor™ 647 conjugate in sample buffer. Each sample was measured in duplicates for all equilibrium experiments. The $K_D$ was obtained from non-linear regression analysis of the data using a one-site homogeneous binding model contained within the KinExA® software (Version 4.0.11) using the "standard analysis" method. The software calculates the $K_D$ and determines the 95% confidence interval by fitting the data points to a theoretical $K_D$ curve. The 95% confidence interval is given as $K_D$ low and $K_D$ high.

For the final $K_D$ determination a n-curve determination of the two measurements with different constant Ang2 concentrations was done. The n-curve analysis may be used to analyze multiple standard $K_D$ experiments on the same axis to obtain a more accurate determination of the $K_D$.

Human VEGF-A Binding Kinetics as Assessed by Surface Plasmon Resonance (SPR):

An anti-His capturing antibody (GE Healthcare 28995056) was immobilized to a Series S Sensor Chip C1 (GE Healthcare BR100535) using standard amine coupling chemistry resulting in a surface density of approximately 600 resonance units (RU). As running and dilution buffer, HBS-P+ (10 mM HEPES, 150 mM NaCl pH 7.4, 0.05% Surfactant P20) was used. Human VEGF-A121-His was captured to the surface with resulting ligand densities of approximately 10 and 20 RU, respectively. A dilution series of the tested antibody (3.7-300 nM, 1:3 dilution) was successively injected for 60 s each, dissociation was monitored for 3600 s at a flow rate of 30 µl/min (single cycle kinetics). The surface was regenerated by injecting 10 mM Glycine pH 1.5 for 60 s at a flow of 5 µl/min. Bulk refractive index differences were corrected by subtracting blank injections and by subtracting the response obtained from the control flow cell without captured human VEGF-A121. Curve fitting was performed using the 1:1 Langmuir binding model within the Biacore® evaluation software.

VEGF-A Binding Kinetics as Assessed by Surface Plasmon Resonance (SPR) for Crossreactivity Testing:

An anti-His capturing antibody (GE Healthcare 28995056) was immobilized to a Series S Sensor Chip C1 (GE Healthcare BR100535) using standard amine coupling chemistry resulting in a surface density of approximately 600 resonance units (RU). As running and dilution buffer, HBS-P+ (10 mM HEPES, 150 mM NaCl pH 7.4, 0.05% Surfactant P20) was used. VEGF-A121-His from the indicated specied was captured to the surface with resulting ligand densities of approximately 10 and 20 RU, respectively. A dilution series of the tested antibody (3.7-300 nM, 1:3 dilution) was successively injected for 60 s each, dissociation was monitored for 3600 s at a flow rate of 30 µl/min (single cycle kinetics). The surface was regenerated by injecting 10 mM Glycine pH 1.5 for 60 s at a flow of 5 µl/min. Bulk refractive index differences were corrected by subtracting blank injections and by subtracting the response obtained from the control flow cell without captured VEGF-A121. Curve fitting was performed using the 1:1 Langmuir binding model within the Biacore® evaluation software.

Human ANG2 Binding Kinetics as Assessed by Surface Plasmon Resonance (SPR):

An anti-Fab capturing antibody (GE Healthcare 28958325) was immobilized to a Series S Sensor Chip C1 (GE Healthcare BR100535) using standard amine coupling chemistry resulting in a surface density of approximately 800 resonance units (RU). As running and dilution buffer, HBS-P+ (10 mM HEPES, 150 mM NaCl pH 7.4, 0.05% Surfactant P20) was used, the temperature of measurement was 25° C. The tested antibody was captured by injecting a 50 nM solution for 60 sec at a flow of 5 µl/min. Association was measured by injection of human Ang2-RBD in various concentrations in solution for 180 sec at a flow of 30 µl/min (0.07 nM-50 nM, 1:3 dilution). The dissociation phase was monitored for up to 900 sec and triggered by switching from the sample solution to running buffer at a flow rate of 30 µl/min. The surface was regenerated by injection of 10 mM Glycine pH 2.1 for 60 s at a flow rate of 30 µl/min. Bulk refractive index differences were corrected by subtracting blank injections and by subtracting the response obtained from the reference flow cell without captured tested antibody. Curve fitting was performed using the 1:1 Langmuir binding model within the Biacore® evaluation software.

ANG2 Binding Kinetics as Assessed by Surface Plasmon Resonance (SPR) for Crossreactivity Testing:

An anti-Fab capturing antibody (GE Healthcare 28958325) was immobilized to a Series S Sensor Chip C1 (GE Healthcare BR100535) using standard amine coupling chemistry resulting in a surface density of approximately 800 resonance units (RU). As running and dilution buffer, HBS-P+ (10 mM HEPES, 150 mM NaCl pH 7.4, 0.05% Surfactant P20) was used, the temperature of measurement was 25° C. The tested antibody was captured by injecting a 50 nM solution for 60 sec at a flow of 5 µl/min. Association was measured by injection of Ang2-RBD from the indicated species in various concentrations in solution for 180 sec at a flow of 30 µl/min (0.07 nM-50 nM, 1:3 dilution). The dissociation phase was monitored for up to 600 sec and triggered by switching from the sample solution to running buffer at a flow rate of 30 µl/min. The surface was regenerated by injection of 10 mM Glycine pH 2.1 for 60 s at a flow rate of 30 µl/min. Bulk refractive index differences were corrected by subtracting blank injections and by subtracting the response obtained from the reference flow cell without captured antibody. Curve fitting was performed using the 1:1 Langmuir binding model within the Biacore® evaluation software.

Assessment of Independent Binding to Target Antigens with Surface Plasmon Resonance (SPR)

Around 5000 resonance units (RU) of the capturing system (anti-Fab capturing antibody (GE Healthcare 28958325)) were coupled on a CM5 chip (GE Healthcare BR100530) at pH 5.0 by using an amine coupling kit supplied by the GE Healthcare. The sample and system buffer was HBS-P+ (10 mM HEPES, 150 mM NaCl pH 7.4, 0.05% Surfactant P20). The temperature of the flow cell was set to 25° C. and of the sample block to 12° C. Before capturing, the flow cell was primed with running buffer three times.

The bispecific Fab was captured by injecting a 6.5 µg/ml solution for 60 sec at a flow of 5 µl/min. Independent binding of each ligand to the bispecific Fab was analysed by determining the active binding capacity for each ligand, either added sequentially or simultaneously (flow of 10 µl/min):

1) Injection of human VEGFA-121 with a concentration of 1 µg/ml for 60 sec (identifies the single binding of the antigen).
2) Injection of human Ang2 with a concentration of 5 µg/ml for 60 sec (identifies single binding of the antigen)
3) Injection of human VEGFA-121 with a concentration of 1 µg/ml for 60 sec followed by an additional injection of human Ang2 with a concentration of 5 µg/ml for 60 sec (identifies binding of Ang2 in the presence of VEGFA-121).
4) Injection of human Ang2 with a concentration of 5 µg/ml for 60 sec followed by an additional injection of human VEGFA-121 with a concentration of 1 µg/ml for 60 sec (identifies binding of VAGFA-121 in the presence of Ang2).
5) Co-Injection of human VEGFA-121 with a concentration of 1 µg/ml and of human Ang2 with a concentration of 5 µg/ml for 60 sec (identifies the binding of VEGFA-121 and of Ang2 at the same time).

The surface was regenerated by injection of 10 mM Glycine pH 2.1 for 60 s at a flow rate of 30 µl/min. Bulk refractive index differences were corrected by subtracting blank injections and by subtracting the response obtained from the reference flow cell without captured bispecific Fab. The bispecific antibody is able to bind both antigens mutual independently if the resulting final signal of the approaches 3, 4 & 5 equals the sum of the individual final signals of the approaches 1 and 2.

Thermal Stability:

Samples of the bispecific antibody Fab fragment were prepared at a concentration of 1 mg/mL in 20 mM Histidine/Histidine chloride, 140 mM NaCl, pH 6.0, and transferred to a 10 µL micro-cuvette array. Static light scattering data as well as fluorescence data upon excitation with a 266 nm laser are recorded using an UNcle instrument (Unchained Labs), while samples are heated at a rate of 0.1° C./min from 30° C. to 90° C. Samples were measured in triplicates.

The evaluation of the onset temperatures was done by the UNcle analysis software. The aggregation onset temperature is defined as the temperature at which the scattered light intensity starts to increase. The denaturation of the protein was monitored by the shift in the barycentric mean (BCM) of the fluorescence signal over the thermal. The melting temperature is defined as the inflection point of the BCM (nm) vs. temperature curve.

Physicochemical Stability:

Antibody samples were formulated in 20 mM His/HisCl, 140 mM NaCl, pH 6.0, and were split into three aliquots: one aliquot was re-buffered into PBS, respectively, and two aliquots were kept in the original formulation. The PBS aliquot and one His/HisCl aliquot were incubated for 2 weeks (2 w) at 40° C. (His/NaCl) or 37° C. (PBS) in 1 mg/ml, the PBS sample was incubated further for total 4 weeks (4 w). The third control aliquot sample was stored at −80° C. After incubation ended, samples were analyzed for relative active concentration (Biacore®; active concentration of both stressed aliquots of each binder is normalized to unstressed 4° C. aliquot), aggregation (SEC) and fragmentation (capillary electrophoresis or SDS-PAGE, CE-SDS) and compared with the untreated control.

Human VEGF-A and Human ANG2 Binding Kinetics Assessed by SPR for Functional Stability Testing VEGFA-121 (inhouse), Protein A (Pierce/Thermo Scientific 21181) and anti-human Fab capturing antibody (GE Healthcare 28958325) were immobilized on different flow cells to a Series S Sensor Chip CMS (GE Healthcare 29104988) using standard amine coupling chemistry resulting in surface densities of 3000 for hVEGFA-121 and Protein A and 12000 resonance units (RU) for anti-human Fab capturing antibody. As running and dilution buffer, HBS-N (10 mM HEPES, 150 mM NaCl pH 7.4, GE Healthcare) was used. Sample and Running buffer for the following concentration measurements were HBS-P (10 mM HEPES, 150 mM NaCl pH 7.4, 0.05% Surfactant P20; GE Healthcare). The temperature of the flow cells was set to 25° C. and of the sample block to 12° C. The flow cell was primed twice with running buffer prior to concentration measurement. First, human Ang2-RBD-hFc Dimer was captured by injecting a 10 µg/ml solution for 120 sec at a flow of 10 µl/min. The tested antibodies were injected in solution for 60 sec at a flow rate of 5 µl/min at a concentration of 1 µg/ml. The dissociation phase was monitored for up to 30 sec and triggered by switching from sample solution to running buffer.

The hVEGFA-121 surfaces were regenerated by 30 sec washing with a 10 mM Glycine pH2.0 solution at a flow rate of 30 µl/min. The Protein A surfaces were regenerated by 30 sec washing with a 10 mM Glycine pH1.5 solution at a flow rate of 30 µl/min. Finally, the anti-human Fab antibody surfaces were regenerated by 60 sec washing with a 10 mM Glycine pH2.1 solution at a flow rate of 30 µl/min.

Bulk refractive index differences were corrected by subtracting the response obtained from a blank surface. For evaluation, the binding response was taken.

The relative active concentration was calculated by referencing each temperature stressed sample to the corresponding, non-stressed sample.

$$rel\_active\_conc = \frac{rel\_binding_{sample}}{rel\_binding_{reference}}$$

To normalize the binding signal of the antigens, the hVEGF-A121 binding and the Ang2 binding was normalized to its anti-Fab binding of the antibody sample:

$$rel\_active\_conc_{norm} = \frac{rel\_active\_conc_{sample} * 100}{(rel\_active\_conc_{fab\_capture\_level})}$$

Example 1

Generation of Bispecific Anti-VEGF-A/Anti-ANG2 Fab Fragment

A bispecific anti-VEGF-A/anti-ANG2 Fab fragment was generated by independent screening of monospecific antibodies that bind to VEGF-A and ANG2 and subsequent merging of the amino acid sequence into a biparatopic HC/LC pair forming a Fab fragment that binds to VEGF-A and ANG2, by a method as described before, e.g. in WO2012/163520.

Two distinct phage display libraries of synthetic Fab fragments were utilized, wherein in the first phage display library residues within the CDR-H1, CDR-H3 and CDR-L2 regions of the Fab fragments were diversified, and wherein in the second phage display library residues within the CDR-L1, CDR-L3 and CDR-H2 regions of the Fab fragments were diversified. In each library the other three CDR regions were kept non-diversified as invariant dummy sequence. In both libraries the CH1 domain of the Fab fragments was fused via a linker to a truncated gene-III protein to facilitate phage display.

The first library was enriched for binders against human ANG2, and the second library was enriched for binders against human VEGF-A, by phage library panning. Following panning, plasmid minipreps were generated for both enriched pools of phagemid vectors. The minipreps were digested with a restriction enzyme to excise the region encoding the truncated gene-III protein and re-circularized by ligation to obtain pools of expression vectors encoding soluble Fab fragments that were enriched for ANG2 binders or for VEGF-A binders, respectively. These vector pools were transformed into TG1 E. coli cells and individual colonies were picked and cultured for soluble expression of individual Fab clones in microtiter plates. The supernatants comprising soluble Fab fragments were screened for binding to ANG2 or VEGF-A using standard ELISA methods, and TG1 clones producing specific binders were subjected to DNA plasmid preparation and sequencing, to obtain pairs of VH and VL sequences specifically binding either to ANG2 or to VEGF-A, respectively.

A pair of bispecific anti-VEGF-A/anti-ANG2 VH and VL sequences was designed in silico by (1) replacing the irrelevant VH residues 52b to 65 in the VH sequence of an ANG2-specific Fab with selected VH residues 52b to 65 of a VEGF-A-specific Fab, thus substituting CDR-H2 residues potentially being part of the VEGF-A-specific paratope into the ANG2 binder heavy chain, and (2) replacing the irrelevant VL residues 49 to 57 in the VL sequence of a VEGF-A-specific Fab with selected VL residues 49 to 57 of an ANG2-specific Fab, thus substituting CDR-L2 residues potentially being part of the ANG2-specific paratope into the VEGF-A binder light chain.

Example 2

Expression of Bispecific Anti-VEGF-A/Anti-ANG2 Fab Fragment P1AA8906

The resulting designed pair of bispecific anti-VEGF-A/anti-ANG2 VH and VL sequences was synthesized and cloned into an E. coli expression vector in frame with gene sequences encoding CH1 and Ckappa domains. The vector was transformed into TG1 E. coli cells, and an individual colony was cultured for soluble expression of the bispecific antibody Fab fragment. The bispecific antibody was purified from the TG1 culture supernatant by affinity chromatography, and specific binding to both ANG2 and VEGF-A was verified.

Bispecific anti-VEGF-A/anti-ANG2 antibody "P1AA8906" was selected, and is characterized by a heavy chain of SEQ ID NO:9 and a light chain of SEQ ID NO:10.

For further analyses anti-VEGF-A/anti-ANG2 antibodies of the invention were transformed into and expressed from CHO cells by standard recombinant methods.

Example 3

Characterization of Bispecific Anti-VEGF-A/Anti-ANG2 Fab Fragment P1AA8906

Binding affinity of bispecific antibody P1AA8906 was assessed by SPR and KinExA® as described above in the "Materials & general methods" section.

TABLE 1

Human VEGFA-121 binding:

| KinExA® | | | | SPR | | | |
|---|---|---|---|---|---|---|---|
| $K_D$ | $K_D$ high | $K_D$ low | Conf. interval | ka [1/Ms] | kd [1/s] | t1/2 [min] | $K_D$ [pM] |
| 10.86 pM | 47.94 pM | <39.23 fM | 95% | 1.66E+06 | (4.53E−06)* | 2551 | (3)* |

*outside of Biacore® specification

The KinExA® analysis was done under following conditions: VEGF-A-121 concentration: 100 pM/1000 pM (CBP), P1AA8906 4 nm-0 pM (1:2 dilution, 12×), Preincubation time ~8 h at RT.

TABLE 2

Human ANG2 binding:

| KinExA® | | | | SPR | | | |
|---|---|---|---|---|---|---|---|
| $K_D$ | $K_D$ high | $K_D$ low | Conf. interval | ka [1/Ms] | kd [1/s] | t1/2 [min] | $K_D$ [pM] |
| 7.18 nM | 12.67 nM | <3.45 nM | 95% | 7.03E+06 | 3.20E−02 | 0.4 | 4554 |

The KinExA® analysis was done under following conditions: VEGF-A-121 concentration: 100 pM/1000 pM (CBP), P1AA8906 4 nm-0 pM (1:2 dilution, 12×), Preincubation time ~8 h at RT.

Thermal stability of bispecific antibody P1AA8906 was assessed as described above in the "Materials & general methods" section.

TABLE 3

Thermal stability

| Tagg (° C.) | Tm (° C.) DLS |
|---|---|
| 73.7 | 85.7 |

Physicochemical stability of bispecific antibody P1AA8906 was assessed as described above in the "Materials & general methods" section.

TABLE 4

Physicochemical stability (SEC)

| | T0 (His/NaCl) | 2 w 40° C. (His/NaCl) | T0 (PBS) | 2 w 37° C. (PBS) | 4 w 37° C. (PBS) |
|---|---|---|---|---|---|
| Monomer [%] | 97.2 | 96.9 | 97.5 | 95.3 | 92.6 |
| HMW [%] | 2.8 | 3.1 | 2.5 | 4.7 | 7.4 |

TABLE 5

Physicochemical stability (CE-SDS)

| | T0 (His/NaCl) | 2 w 40° C. (His/NaCl) | T0 (PBS) | 2 w 37° C. (PBS) | 4 w 37° C. (PBS) |
|---|---|---|---|---|---|
| Monomer [%] | 98.5 | 97.9 | 95.6 | 94.8 | 93.0 |
| HMW [%] | 1.5 | 2.1 | 4.4 | 5.2 | 7.0 |

Example 4

Improvement of Bispecific Anti-VEGF-A/Anti-ANG2 Fab Fragment P1AA8906

As illustrated above, P1AA8906, while exhibiting a high thermal stability and advantageous affinity towards VEGF-A, exhibits an affinity to ANG2 in the nanomolar range as well as a tendency to form high molecular weight impurities which increases under stress. For treatment of ocular vascular diseases, which requires injection of the therapeutic into the eye, it is desirable to provide the therapeutic with a high affinity for the target antigen and in very high concentrations to increase durability of the therapeutic effect and to minimize inconveniences for the patient. For the intended purpose it is therefore desired to increase affinity and to improve the physicochemical stability.

Consequently, for clinical application the antibody required further improvement, e.g. with respect to ANG2 binding (particularly by improving the off-rate) and reducing susceptibility to stress. Several rounds of maturations were performed by introducing distinct amino acid substitutions in the VH and VL domain. During the maturations candidate antibodies derived from antibody P1AA8906 were screened and selected based on their desired properties with respect to yield, affinity, simultaneous antigen binding, hydrophilicity, stability, viscosity and other parameters.

Improved candidate antibody P1AA0902 was selected from a plurality of tested candidate antibody molecules. Starting from this molecule further rounds of optimizations were performed, again by introducing distinct amino acid substitutions in the VH and VL domain. Candidate selection was based its desired properties, particularly improving ANG2 binding and assuring syringeability at high concentrations while maintaining other advantageous characteristics, e.g. VEGF-A affinity, simultaneous antigen binding and thermal stability.

Further improved candidate antibody P1AD9820 was selected from a plurality of tested candidate antibody molecules.

TABLE 6

Amino acid sequences of bispecific Fab fragments P1AA8906, P1AA0902, P1AD9820 (the numbers refer to the SEQ ID NOs as used herein)

| | VH | VL | heavy chain | light chain |
|---|---|---|---|---|
| P1AA8906 | 1 | 2 | 9 | 10 |
| P1AA0902 | 11 | 12 | 17 | 18 |
| P1AD9820 | 19 | 20 | 24 | 25 |

FIGS. 2 and 3 illustrate an alignment of the variable heavy chain domains and the variable light chain domains of the generated bispecific fragments. Numbering of the amino acid positions within the VH and VL domains is according to the Kabat numbering system. For simplicity, the numbering is included in the Figure, further illustrating framework and CDR amino acid positions.

The candidate antibodies were expressed as described in Example 2.

Example 5

Antigen Binding Kinetics of Improved Anti-VEGF-A/Anti-ANG2 Fab Fragments

Binding kinetics to human VEGF-A and human ANG2 for the candidate antibodies were assessed as described above using the indicated Fab fragments (amino acid sequence as illustrated in Table 4). In order to compare the antigen binding kinetics of the antibodies of the invention to prior art molecules Faricimab (INN, previously also referred to as RG7716), anti-VEGF binders Aflibercept (INN), and Brolucizumab (INN), and anti-ANG2 binder Nesvacumab (INN) the aforementioned prior art antibodies were prepared by recombinant expression of the identical amino acid sequences disclosed in their respective INN. The reference molecules are herein also termed "analogues" to emphasize that they were in house preparations.

TABLE 7

Human VEGFA-121 binding (KinExA ®)

| | $K_D$ | $K_D$ high | $K_D$ low | Conf. interval |
|---|---|---|---|---|
| P1AA8906 | 10.86 pM | 47.94 pM | <39.23 fM | 95% |
| P1AA0902 | 11.41 pM | 32.81 pM | <295.81 fM | 95% |
| P1AD9820 | 3.85 pM | 11.22 pM | <175.67 fM | 95% |

TABLE 8

Human VEGFA-121 binding (SPR)

| | ka [1/Ms] | kd [1/s] | t1/2 [min] | $K_D$ [pM] |
|---|---|---|---|---|
| P1AA8906 | 1.66E+06 | (4.53E−06)* | 2551 | (3)* |
| P1AA0902 | 7.37E+05 | (8.27E−06)* | 1396 | (11)* |
| P1AD9820 | 7.27E+05 | (5.82E+06)* | 1986 | (8)* |

*outside of Biacore ® specification

TABLE 9

Human VEGF-A binding ($K_D$ as measured by KinExA ®)

| Molecule | VEGFA-121 | VEGFA-165 |
|---|---|---|
| P1AD9820 | ~4 pM | ~2 pM |
| Faricimab (RG7716) | 169 pM | 224 pM |
| Aflibercept-analogue | 0.2 pM | 0.1 pM |
| Brolucizumab-analogue | 2 pM | 1 pM |

TABLE 10

Human ANG2 binding (KinExA ®)

| | $K_D$ | $K_D$ high | $K_D$ low | Conf. interval |
|---|---|---|---|---|
| P1AA8906 | 7.18 nM | 12.67 nM | <3.45 nM | 95% |
| P1AA0902 | 2.75 pM | 14.23 pM | <9.92 fM | 95% |
| P1AD9820 | 1.72 pM | 6.55 pM | <6.22 fM | 95% |

TABLE 11

Human ANG2 binding (SPR)

| | ka [1/Ms] | kd [1/s] | t1/2 [min] | $K_D$ [pM] |
|---|---|---|---|---|
| P1AA8906 | 7.03E+06 | 3.20E−02 | 0.4 | 4554 |
| P1AA0902 | 5.51E+06 | 1.06E−04 | 109 | 19 |
| P1AD9820 | 7.43E+06 | 5.78E−05 | 200 | 8 |

TABLE 12

Human ANG2 binding ($K_D$ as measured by KinExA ®)

| Molecule | VEGFA-121 |
|---|---|
| P1AD9820 | ~2 pM |
| Faricimab (RG7716) | 7 nM |
| Nesvacumab-analogue | 10 pM |

Independent binding of candidate antibodies to human VEGF-A and human ANG2 was analysed by SPR as described above in the "Materials & general methods" section.

TABLE 13

Independent binding to human VEGFA-121 and human ANG2

| molecule | | Inject 1 | Inject 2 | Signal [%] |
|---|---|---|---|---|
| P1AA8906 | 1) | VEGFA-121 | HBS-P | 50 |
| | 2) | Ang2-RBD | HBS-P | 50 |
| | 3) | VEGFA-121 | Ang2-RBD | 82 |
| | 4) | Ang2-RBD | VEGFA-121 | 91 |
| | 5) | Mix (VEGF + Ang2) | HBS-P | 100 |
| P1AA0902 | 1) | VEGFA-121 | HBS-P | 50 |
| | 2) | Ang2-RBD | HBS-P | 50 |
| | 3) | VEGFA-121 | Ang2-RBD | 85 |
| | 4) | Ang2-RBD | VEGFA-121 | 90 |
| | 5) | Mix (VEGF + Ang2) | HBS-P | 102 |
| P1AD9820 | 1) | VEGFA-121 | HBS-P | 50 |
| | 2) | Ang2-RBD | HBS-P | 50 |
| | 3) | VEGFA-121 | Ang2-RBD | 85 |
| | 4) | Ang2-RBD | VEGFA-121 | 92 |
| | 5) | Mix (VEGF + Ang2) | HBS-P | 104 |

Crossreactivity to VEGF-A and ANG2 from other species was assessed as described above in "Materials & general methods" section.

TABLE 14

Assessment of crossreactivity of P1AD9820 Fab fragment to VEGF-A from other species

| | ka [1/Ms] | kd [1/s] | t1/2 [min] | $K_D$* [pM] |
|---|---|---|---|---|
| Human VEGF-A-121 | 4.86E+05 | 2.21E−05 | 523 | 45.5 |

TABLE 14-continued

Assessment of crossreactivity of P1AD9820 Fab fragment to VEGF-A from other species

|  | ka [1/Ms] | kd [1/s] | t1/2 [min] | $K_D$* [pM] |
|---|---|---|---|---|
| Mouse VEGF-A-121 | 4.97E+05 | 1.83E−04 | 63 | 368.1 |
| Rabbit VEGF-A-121 |  | very low binding |  |  |
| Pig VEGF-A-121 | 1.79E+05 | 4.99E−04 | 23 | 2790 |

*$K_D$ depends on assay setup. The indicated $K_D$ is valid for the setup of the crossreactivity testing described above.

TABLE 15

Assessment of crossreactivity of P1AD9820 Fab fragment to ANG2 from other species

|  | ka [1/Ms] | kd [1/s] | t1/2 [min] | $K_D$* [pM] |
|---|---|---|---|---|
| Human ANG2 | 1.02E+07 | 2.64E−05 | 437 | 3 |
| Mouse ANG2 | 8.11E+06 | 7.43E−04 | 16 | 92 |
| Rabbit ANG2 | 9.91E+06 | 5.33E−05 | 217 | 5 |
| Pig ANG2 | 7.82E+06 | 1.05E−04 | 110 | 13 |
| Cyno ANG2 | 9.98E+06 | 1.56E−05 | 741 | 2 |

*$K_D$ depends on assay setup. The indicated $K_D$ is valid for the setup of the crossreactivity testing described above.

Example 6

Thermal Stability of Improved Anti-VEGF-A/Anti-ANG2 Fab Fragments

Thermal stability of the indicated bispecific antibodies was assessed as described above in the "Materials & general methods" section and under the same conditions as for Example 3.

TABLE 16

Thermal stability

|  | Tagg (° C.) | Tm (° C.) |
|---|---|---|
| P1AA8906 | 73.7 | 85.7 |
| P1AA0902 | 70.2 | 83.5 |
| P1AD9820 | 71.6 | 81.3 |
| Faricimab (RG7716) | 64.7 | 63.6 |

Example 7

Biophysical Properties of Improved Bispecific Anti-VEGF-A/Anti-ANG2 Fab Fragments (Stability)

Physicochemical stability of the indicated bispecific antibodies was assessed as described above in the "Materials & general methods" section and under the same conditions as for Example 3.

TABLE 17

Physicochemical stability (SEC)

|  | T0 (His/NaCl) | 2w 40° C. (His/NaCl) | 4w 40° C. (His/NaCl) | T0 (PBS) | 2w 37° C. (PBS) | 4w 37° C. (PBS) |
|---|---|---|---|---|---|---|
| P1AA8906 |  |  |  |  |  |  |
| Monomer [%] | 97.2 | 96.9 |  | 97.5 | 95.3 | 92.6 |
| HMW [%] | 2.8 | 3.1 |  | 2.5 | 4.7 | 7.4 |
| P1AA0902 |  |  |  |  |  |  |
| Monomer [%] | 98.80 | 99.64 | 99.44 | 98.80 | 99.02 | 98.35 |
| HMW [%] | 0.20 | 0.36 | 0.56 | 0.20 | 0.98 | 1.65 |
| P1AD9820 |  |  |  |  |  |  |
| Monomer [%] | 99.00 | 98.17 |  | 99.00 | 97.43 | 96.90 |
| HMW [%] | 1.00 | 1.83 |  | 1.00 | 2.57 | 3.10 |

Example 8

Biophysical Properties of Improved Bispecific Anti-VEGF-A/Anti-ANG2 Fab Fragments (Viscosity Assessment by Dynamic Light Scattering (DLS))

P1AA0902 and P1AD9820 Fab fragments as described before were expressed in *E. coli* cells by standard methods.

Viscosity was measured with the latex-bead DLS method as described before (He F et al.; Anal Biochem. 2010 Apr. 1; 399(1):141-3). Specifically, the following protocol was followed using the indicated materials.

Viscosity Assessment:
Instrumentation and Materials
Wyatt DLS plate reader with a Greiner Bio-One microplate
3000 Series Nanosphere™ Size Standards (Thermofisher Cat.-No. 3300A)
Tween® 20 (Roche, cat. no. 11332465001) and silicone oil e.g. (Alfa Aesar cat. no. A12728)
UV photometer for concentration determination (e.g. Nanodrop 8000).

Sample Preparation

Antibody samples were re-buffered and diluted in 20 mM His/HCl, pH 6.0 (buffer) and 0.02% Tween® 20 (final concentration). A bead concentration of 0.03% solids was added. At least four different concentrations were prepared, where possible the highest concentration was about 200 mg/mL. Two blank samples were required as antibody-free controls: one comprising the Nanosphere beads resuspended in water, and another one comprising the Nanosphere beads resuspended in buffer. Samples were transferred into the micro plate and each well was covered with silicone oil.

Measurements with Wyatt DLS Plate Reader

All samples and the blanks were analyzed at different temperatures, from 15 to 35° C. in 5° C. steps. The acquisition time was 30 s and the number of acquisitions is 40 per sample and temperature.

Data Analysis

The raw data Dapp (apparent radii) in nm was shown in an overview of the software template (Microsoft Dynamics 7.0 or higher). The viscosity was calculated with a formula (ηreal=Dapp*ηH2O/Dreal). Dreal is the measured bead size in the blank sample, which is equal to the bead size (300 nm). The calculated viscosity was shown in Excel curves. With a Mooney curve Fit (in Excel), it is possible to extrapolate the viscosity at a given concentration. Here, the maximum protein concentration where the viscosity exceeds 20 cP was calculated.

Figure 10:
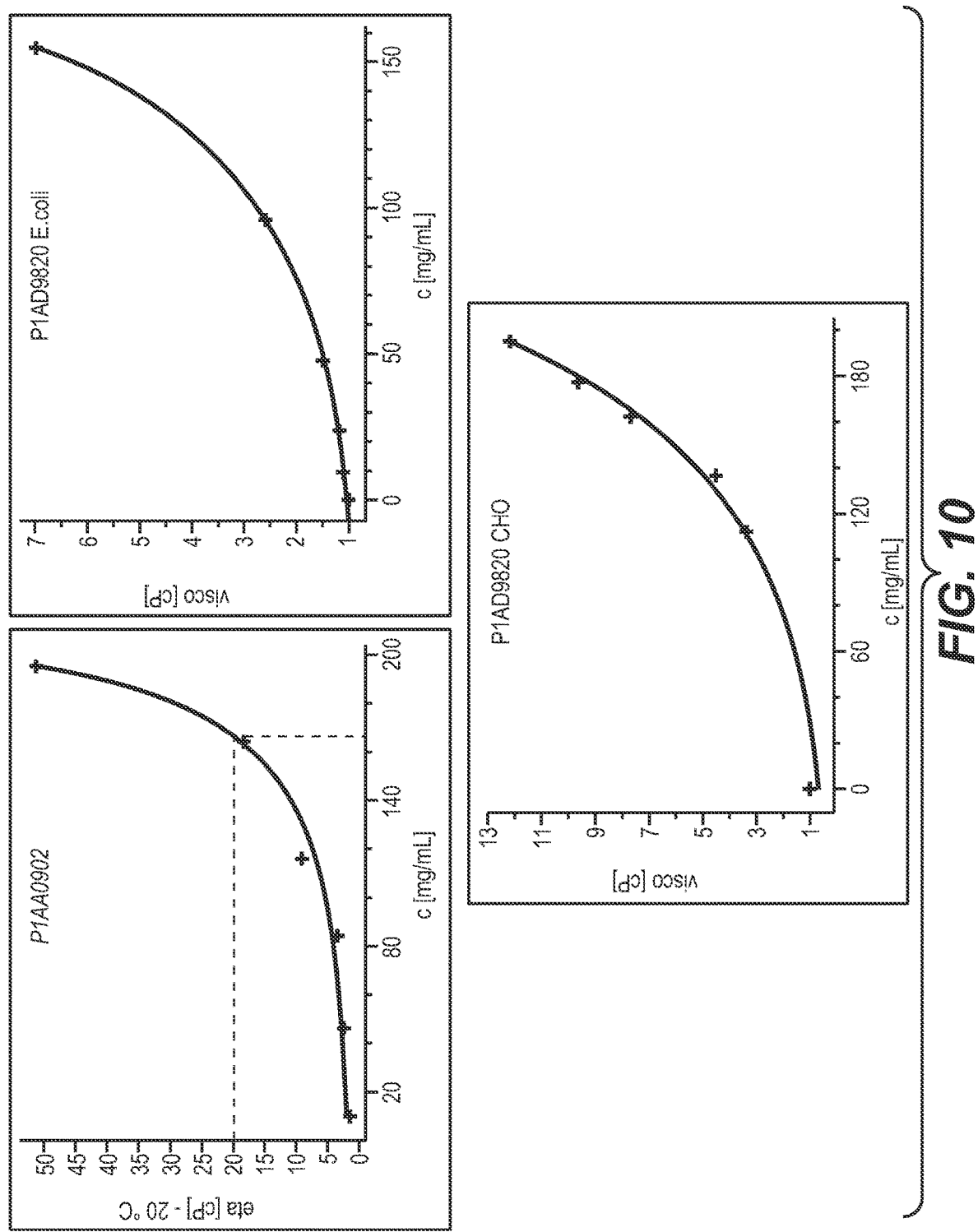
FIG. 10: Viscosity as measured with latex-bead DLS method of P1AA0902 (upper left) and P1AD9820 (upper right) Fab fragments produced in *E. coli* and P1AD9820 produced in CHO (middle) as tested in Example 8.

The maximal concentration of the indicated antibodies to achieve a viscosity of 20 cP at 20° C. is indicated below. Results are also shown in FIG. 10.

TABLE 18

Viscosity by DLS bead method. Shown is the max. feasible concentration of the indicated antibody to reach 20 cP at 20° C. Antibody Fab fragments were expressed in *E. coli*

| antibody | | Concentration [mg/ml] |
| --- | --- | --- |
| P1AA0902 | Fab | 166.3 |
| P1AD9820 | Fab | 195 |

Results indicate that antibodies of the invention may be formulated in high concentrations comprising a viscosity below the acceptable viscosity limit for syringeabilty. While both tested antibodies are shown to be highly concentratable, the effect is more prominent in the P1AD9820 antibody.

In consequence, the antibodies of the invention are highly suitable for ocular application as they allow for provision of a high molar dose in a limited injection volume, which when combined with high potency results in a high durability and consequently, a reduced dosing frequency, which is desirable to reduce difficulties on the patient's side.

In another set of experiments, viscosity of P1AD9820 generated in CHO cells according to standard recombinant methods was analyzed as described above.

The maximal concentration of the indicated antibodies to achieve a viscosity of 20 cP at 20° C. is indicated below. Results are also shown in FIG. 10.

TABLE 19

Viscosity by DLS bead method. Shown is the max. feasible concentration of the indicated antibody to reach 20 cP at 20° C. Antibody Fab fragments were expressed in *E. coli*

| antibody | | Concentration [mg/ml] |
| --- | --- | --- |
| P1AD9820 | E. coli | 195 |
| P1AD9820 | CHO | 223 |

Example 9

Functional Stability of Improved Anti-VEGF-A/Anti-ANG2 Fab Fragments

P1AD9820 Fab fragment was treated under different stress conditions as described above in the "Materials & general methods" section (Physicochemical stability). Antigen binding of the resulting stressed antibody samples was analysed as described above ("Materials & general methods" section: Human VEGF-A and human ANG2 binding kinetics assessed by SPR for functional stability testing).

TABLE 20

Antigen binding (SPR) for stressed samples of P1AD9820

| stress conditions | Relative active concentration [%] VEGFA-121 | Relative active concentration [%] Ang2 |
| --- | --- | --- |
| Initial | 100 | 100 |
| 2 w@40° pH 6,0 | 99 | 100 |
| 2 w@37° PBS | 100 | 101 |
| 4 w@37° PBS | 100 | 102 |

Example 10

Functional Characterization of Improved Anti-VEGF-A/Anti-ANG2 Fab Fragments

ANG2 and VEGF-A inhibition of candidate antibodies was assessed in cell based assays:

ANG2 inhibition: pTie2-Assay

Figure 8:
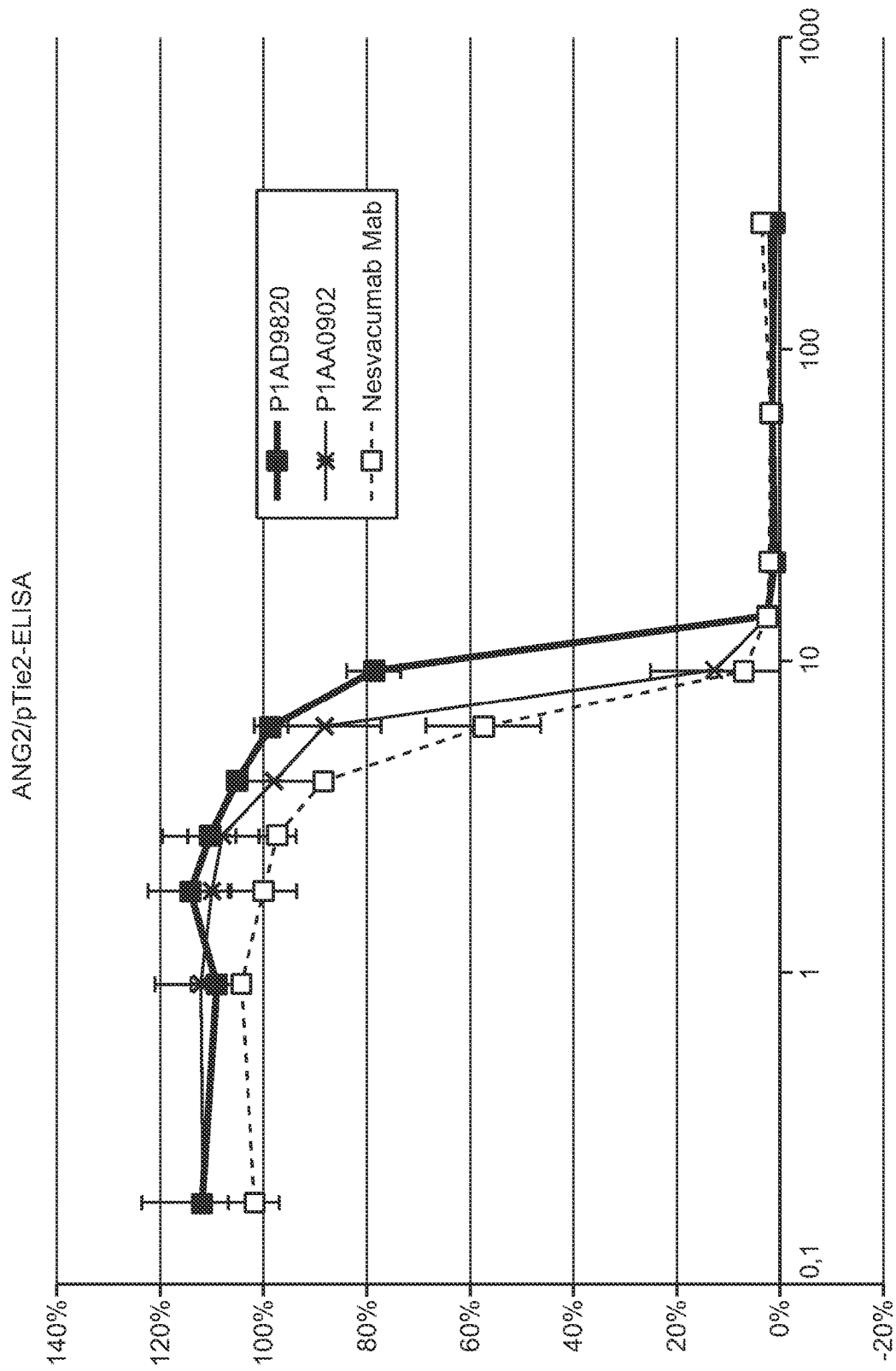
FIG. 8: pTie2-Assay for analysis of ANG2 inhibition of indicated antibodies of the invention and prior art antibody analogue as tested in Example 10.
Figure 9:
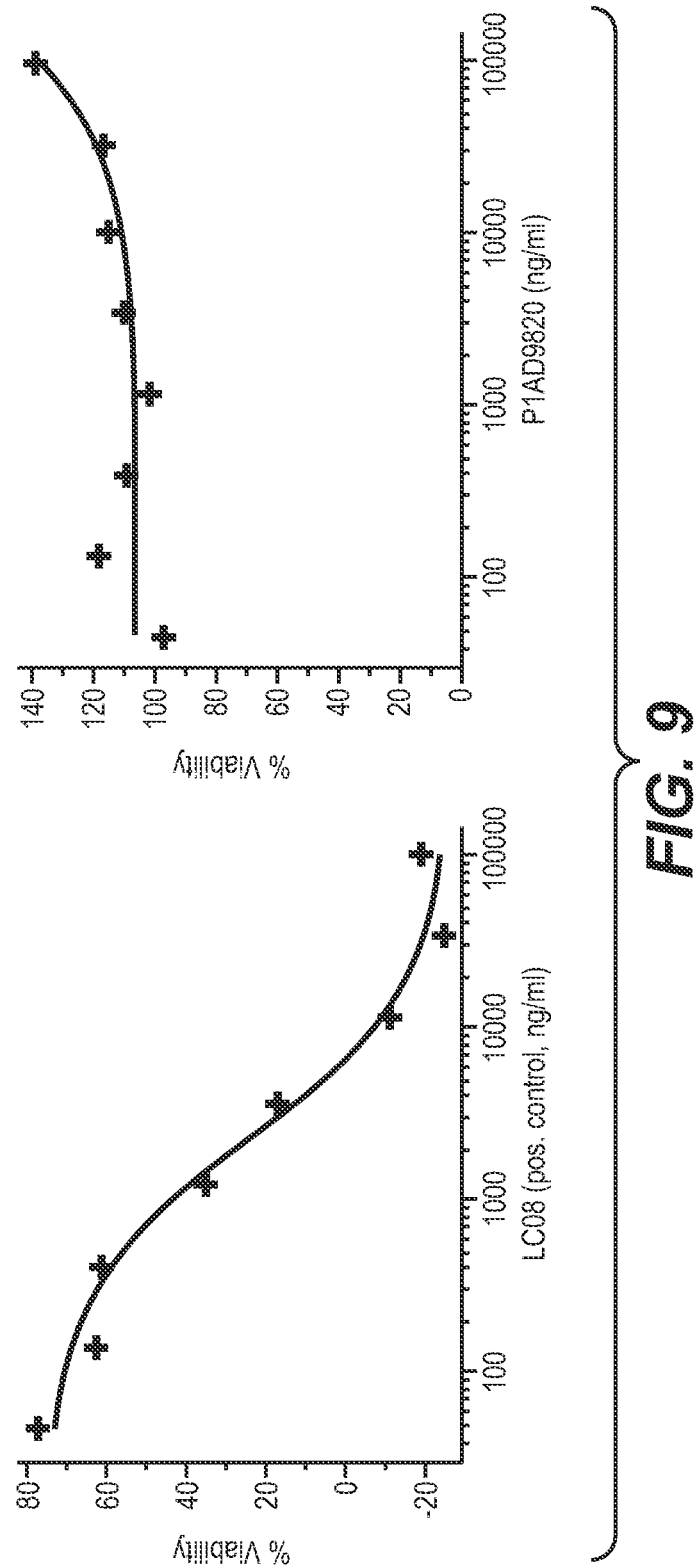
FIG. 9: ANG1 inhibition mediated by P1AD9820 as tested in Example 12.

Candidate antibodies and selected reference molecules (Nesvacumab analogue, in house preparation by recombinant expression according to SEQ ID NOs 29 and 30) were pre-incubated in 11 concentrations ranging from 250 nM to 0.14 nM in MEM Alpha-Medium. Threefold concentrated anti Ang2 antibody in 40 µl was mixed with 40 µl Ang-2 at a threefold concentrated c=3.9 µg/ml and incubated for 30 min in the cell incubator. Then, 40 µl/well Hek293_HOMSA-Tie2-Clone22_B11 cells suspended in FreeStyle medium without selection at a density of 40000 cells per well were added for 10 minutes at RT. The Ang2 phosphorylation was then stopped by addition of cold lysis buffer with protease inhibitors. A MaxiSorp™-plate-bound anti Tie2 antibody then immobilized the Tie2 from the cell lysate for 90 minutes at RT while shaking. After a wash step in PBS, 0.05% Tween® 20, a biotinylated antibody specific for phosphorylated Tie2 was added for 1 hour at RT to a final concentration of 3 µg/ml. Following a three wash steps, HRP coupled strepavidine was added to a final concentration of 100 mU/ml which converted POD for 30 minutes at RT for a final colorimetric end point assessment after stopping with 1M H2SO2 at 405/690 nm using a Tecan Sunrise plate reader. Results are shown below and in FIG. 8.

TABLE 21

ANG2 inhibition (IC50, cell based assay)

| | IC50 [nM] n = 3 |
| --- | --- |
| P1AA0902 | 7 |
| P1AD9820 | 10 |
| Nesvacumab Mab | 6 |

VEGF-A Inhibition: Reporter Gene Assay (RGA)

Figure 7:
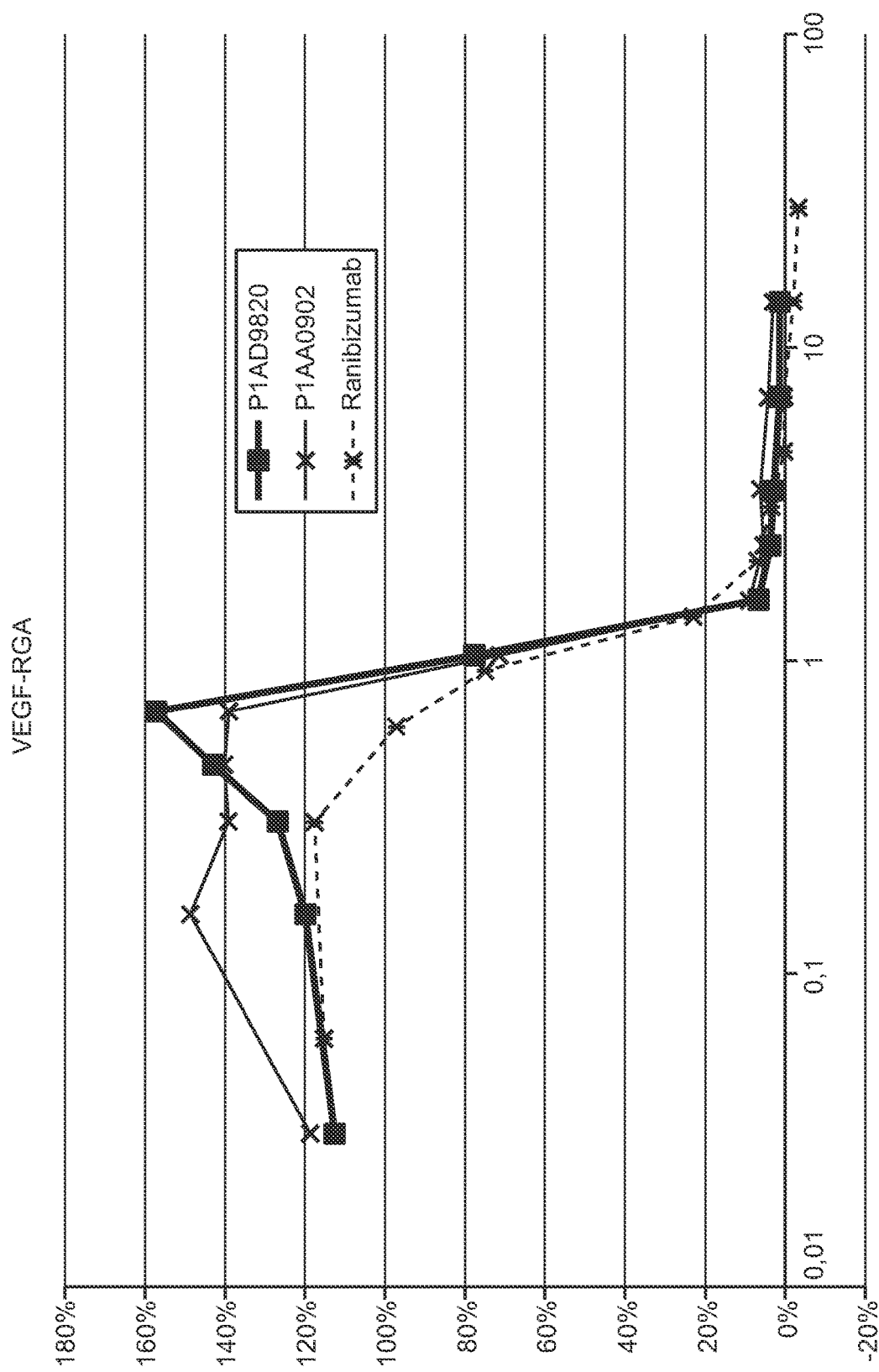
FIG. 7: Reporter Gene Assay (RGA) for analysis of VEGF-A inhibition of indicated antibodies of the invention and prior art antibody analogue as tested in Example 10.

For the assay 37.5 µl of four fold concentrated tested antibody or reference molecule was pre-incubated with four fold concentrated 37.5 µl of VEGF-A121 (R&D, c=100 µg/ml) for 15 min at RT. The mixture was then added to 75 µl/well Hek_NFAT_KDR_Luc cells at a density of 40000 cells/well and incubated for 5 hours in the cell incubator. Finally, after addition of 100 µl BioGlo™ reagent per well, luminescence was assessed using a Infinite Pro Platereader (Tecan). Results are shown below and in FIG. 7.

TABLE 22

VEGF-A inhibition (IC50, cell based assay)

| | IC50 [nM] n = 4 |
|---|---|
| P1AA0902 | 1.09 |
| P1AD9820 | 1.07 |
| Ranibizumab (INN) | 1.10 |

Example 11 hVEGF-A121 and hVEGF-A165 Blocking Activity (VEGF Baseline Assay)

Figure 5:
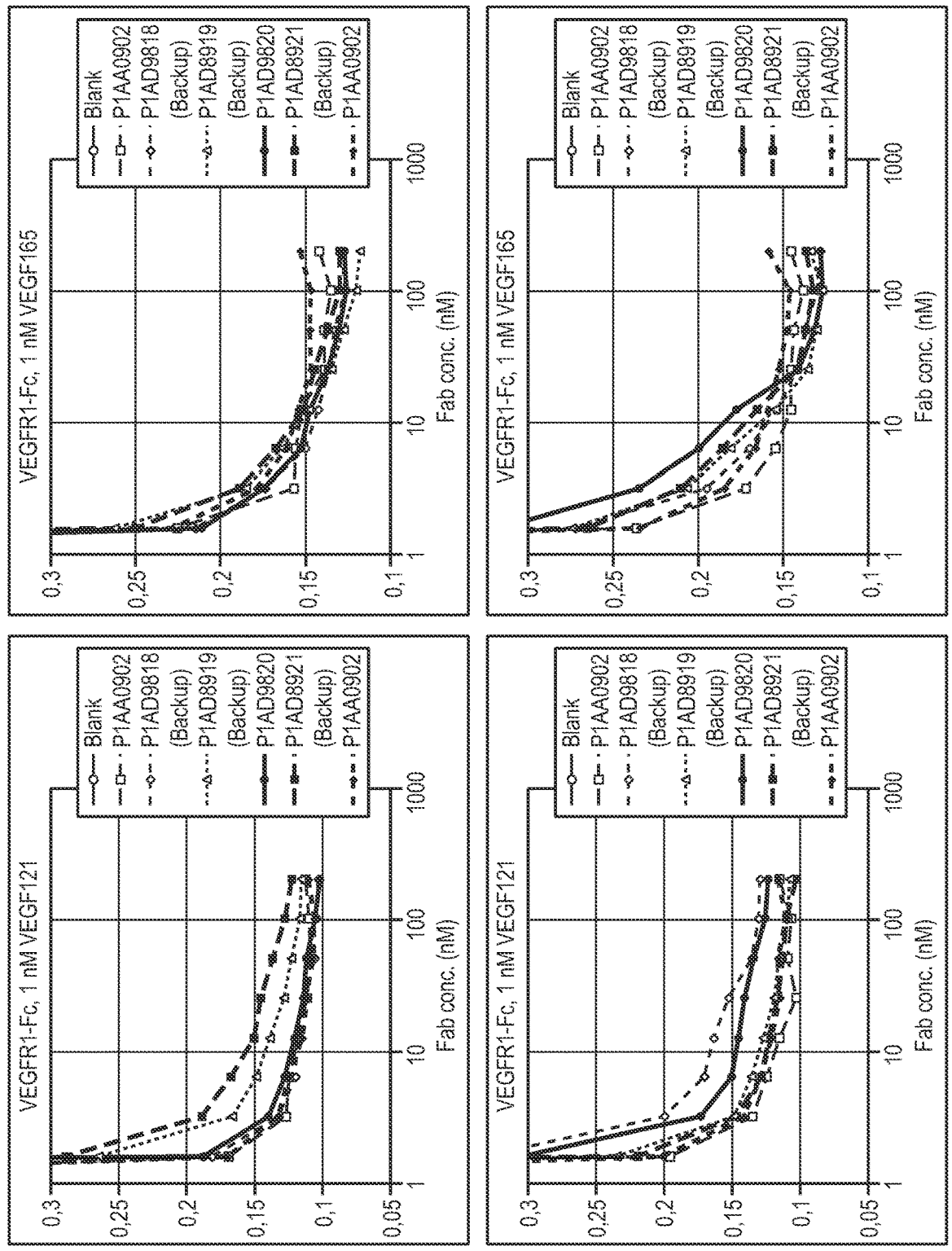
FIG. 5: VEGF-A121 and VEGF-A165 blocking activity of indicated antibodies as tested in Example 11.
Figure 6:
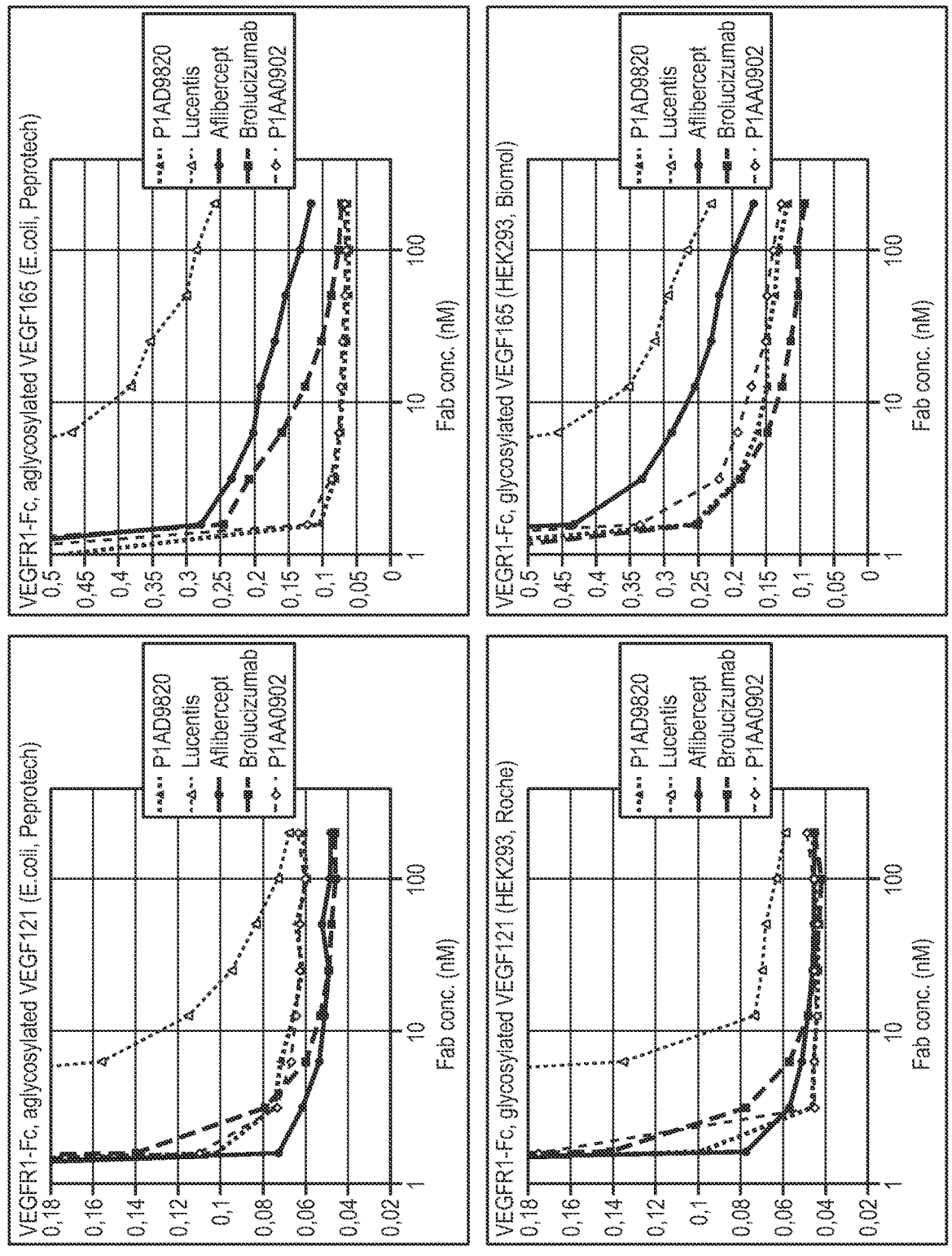
FIG. 6: VEGF-A121 and VEGF-A165 blocking activity of indicated antibodies of the invention and prior art antibody analogues as tested in Example 11.

Maxisorp 96-well plates (ThermoScientific #442404) were coated with 50 μL/well of hVEGFR-1-Fc in 200 mM NaHCO$_3$, pH 9.4, at a final concentration of 1 μg/mL for 1 hour at room temperature. Indicated candidate Fab fragments were diluted to a concentration of 409.6 nM in 280 μL PBST-1% BSA. For a 2 fold serial dilution, 140 μL of this diluted Fab sample was mixed with 140 μL PBST-1% BSA and mixed 7 times by gentle pipetting. This 2 fold dilution step was repeated 9 more times. Round-bottom 96-well plates were pre-filled with 50 μL/well of 2 nM VEGF-A121 or 2 nM VEGF-A165 in PBST-1% BSA. 50 μL of the Fab dilutions were added to the VEGF plates, mixed 6 times and incubated for 1.5 hours. Subsequently, the maxisorp plates were washed 2 times with PBST before adding 200 μL of 2% MPBST followed by incubation for 45 min at room temperature. Afterwards, the plate was washed twice with PBST. 50 μl of the Fab-VEGF premix was transferred to the MaxiSorp™ plate and incubated 1.5 h at room temperature. Afterwards, the plates were washed twice with PBST and 50 μL of anti-VEGF-bio antibody (1:2000 dilution in PBST) and SA-HRP (1:2000 dilution in PBST) were added and incubated for 30 minutes at room temperature. Plates were washed 6× with PBST and 50 μL of TMB substrate solution was added and incubated for 30 min. at room temperature. Finally, add 50 μL 1N sulfuric acid to stop the reaction and read absorbance at 450 nm. Results are shown in FIGS. 5 and 6.

Example 12

Selective Binding of ANG2 Over ANG1

Ang-2 selectivity over Ang-1 may be a critical attribute for ocular safety: ANG1 inhibition of P1AD9820 Fab was assessed in a cell based assay.

ANG-1 is a slight inducer of viability for HUVECs grown under starvation conditions. Therefore viability can be inhibited with an ANG-1 neutralizing antibody. The antibody RO5314196 (formerly LC-08—Thomas M, Kienast Y, Scheuer W, et al. A novel angiopoietin-2 selective fully human antibody with potent anti-tumoral and anti-angiogenic efficacy and superior side effect profile compared to Pan-Angiopoietin-1/-2 inhibitors. PLoS One. 2013; 8(2): e54923. doi:10.1371/journal.pone.0054923) inhibits HUVEC viability by neutralizing ANG-1 and was used as positive control for the assay. Cell culture flasks T162 from Corning (Cat #3151) coated with AF (Attachment Factor) from Gibco (Cat #S-006-100) were used for maintaining HUVECs until passage 5. For the viability assay HUVECs were detached with Accutase® followed by a wash step with PBS-/-. Thereafter, cells were seeded in EBM-2 with 0.5% FBS on fibronectin-coated 96 well plates at a cell density of 10.000 cells/well in 100 μl. Cells were incubated overnight at 37° C. with 5% CO2. The following day, P1AD9820 or the Ang-1 binding positive control RO5314196 were diluted in EBM/0.5% FBS to a 10× working concentration. The starting concentration was 1000 μg/ml followed by a 3-fold 8-point dilution series ending at 457.2 μg/ml. ANG-1 was set up at a 20× working concentration, corresponding to 2400 ng/ml.

Next, 10 μl of the 10× pre-diluted P1AD9820 and subsequently 5 μl of the 20× ANG-1 solution were added to the cells in quadruplicate wells per plate. On each experimental day, each condition was performed in duplicate plates. Cells were incubated at 37° C. with 5% CO2 for 72 hours. For analysis, 11 μl of AlamarBlue® was added to each well and subsequently incubated for 4 h in the cell culture incubator. Absorbance was detected at 570 nm with a reference wavelength of 600 nm.

For each experiment, conditions were duplicated using two assay plates on which each condition was performed in quadruplicates. Background signal of unstimulated cells was subtracted from the experimental wells and the mean signal per condition calculated. The 100% response level was calculated from cells stimulated with ANG-1 (120 ng/ml) without additional treatment and the signal from antibody-treated wells expressed as percentage inhibition of the 100% response. For P1AD9820 and RO5314196 percentage inhibition for each antibody treatment was measured in n=4 independent experiments and the mean and standard error of the mean calculated. IC$_{50}$ values were calculated from the mean data for each antibody concentration using ExcelXLfit software (IDBS). Concentration-response curves were fitted by nonlinear regression analysis using a 5 parameter logistic model $(A+((B-A)/(1+((C/x)^D))))$ calculated relative to basal and maximal inhibitory activity.

The cell based assay did not detect ANG1 inhibition mediated by P1AD9820.

Example 13

Structural Analysis of P1AD9820 Fab Fragment

Structural analysis of P1AD9820 Fab was performed by x-ray crystallography as follows:

Complex formation and purification of the ternary complex Angiopoietin 2-RBD-VEGF-A121-P1AD9820. For complex formation P1AD9820 Fab and human VEGF-A121 (Peprotech) were mixed in a 1.1:1 molar ratio. After incubation for 45 minutes at 4° C. the Angiopoietin 2-RBD was added in a molar ratio to P1AD9820 of 1.25:1 followed by additional 60 minutes at 4° C. The resulting ternary complex was further deglycosylated with PNGaseF (NEB) for 13 hours at 37° C. and in a final step purified by gel filtration chromatography on a Superdex® 200 (16/600) column. Fractions containing the ternary complex were pooled and concentrated to 3.55 mg/ml.

Crystallization of ternary Angiopoietin 2-RBD-VEGF-A121-P1AD9820. Initial crystallization trials were performed in sitting drop vapor diffusion setups at 21° C. at a protein concentration of 14.5 mg/ml. Crystals appeared within 1 day out of 35% MPD, 0.1M Na/K phosphate pH 6.2. Plate shaped crystals grew in a week to a final size of 100×80×30 μm. The crystals were directly harvested from the screening plate without any further optimization steps.

Data collection and structure determination. For data collection crystals were flash cooled at 100K in precipitant solution without any additional cryoprotectant. Diffraction data were collected at a wavelength of 1.0000 Å using a PILATUS 6M detector at the beamline X10SA of the Swiss Light Source (Villigen, Switzerland). Data have been processed with XDS (Kabsch, W. Acta Cryst. D66, 133-144 (2010)) and scaled with SADABS (BRUKER). The crystals belong to the space group C2 with cell axes of a=165.74 Å, b=90.27 Å, c=127.89 Å, β=112.05° and diffract to a resolution of 2.08 Å. The structure was determined by molecular replacement with PHASER (McCoy, A. J, Grosse-Kunstleve, R. W., Adams, P. D., Storoni, L. C., and Read, R. J. *J. Appl. Cryst.* 40, 658-674 (2007)) using the coordinates of a related in house structure of an Ang2-VEGF-Fab ternary complex as search model. Programs from the CCP4 suite (Collaborative Computational Project, Number 4 *Acta Cryst.* D50, 760-763 (1994)) and Buster (Bricogne, G., Blanc, E., Brandi, M., Flensburg, C., Keller, P., Paciorek, W., Roversi, P., Sharff, A., Smart, O. S., Vonrhein, C., Womack, T. O. (2011). Buster version 2.9.5 Cambridge, United Kingdom: Global Phasing Ltd) have been used to subsequently refine the data. Manual rebuilding of protein using difference electron density was done with COOT (Emsley, P., Lohkamp, B., Scott, W. G. and Cowtan, K. *Acta Cryst* D66, 486-501 (2010)). Data collection and refinement statistics for both structures are summarized in Table 23. All graphical presentations were prepared with PYMOL (DeLano Scientific, Palo Alto, Calif., 2002).

TABLE 23

Data collection and structure refinement statistics

| Data Collection | |
|---|---|
| Wavelength (Å) | 1.0 |
| Resolution[1] (Å) | 77.83-2.08 (2.18-2.08) |
| Space group | C2 |
| Unit cell (Å, °) | 165.74 90.27 127.89, 90.00 112.05 90.00 |
| Unique reflections | 104942 (13712) |
| Multiplicity | 3.83 (3.68) |
| Completeness (%) | 0.99 (0.99) |
| Mean I/σ(I) | 7.22 (0.78) |
| Wilson B-factor | 44.64 |
| R-meas | 0.069 (0.780) |
| CC1/2 | 0.999 (0.768) |
| Refinement | |
| Resolution[1] (Å) | 77.83-2.08 (2.13-2.08) |
| Reflections used in refinement | 104910 (7712) |
| Reflections used for R-free | 5243 (357) |
| R-work[3] | 0.218 (0.272) |
| R-free[4] | 0.265 (0.303) |
| Number of atoms | 12200 |
| Protein residues | 1466 |
| RMS bonds (Å) | 0.010 |
| RMS angles (°) | 1.13 |
| Ramachandran favored (%) | 95.8 |
| Ramachandran outliers (%) | 0.35 |
| Rotamer outliers (%) | 4.07 |
| Clashscore | 3.53 |
| Average B-factor (Å$^2$) | 68.29 |
| protein | 66.34 |
| solvent | 59.07 |

[1]Values in parentheses refer to the highest resolution bins.
[2]$R_{merge} = \Sigma|I - <I>|/\Sigma I$ where I is intensity.
[3]$R_{work} = \Sigma|F_o - <F_c>|/\Sigma F_o$, where $F_o$ is the observed and $F_c$ is the calculated structure factor amplitude.
[4]$R_{free}$ was calculated based on 5% of the total data omitted during refinement.

Amino acid residues in contact with the respective antigens, VEGF-A and ANG2, were identified from the crystal structure of the ternary complex Angiopoietin 2-RBD-VEGF-A121-P1AD9820. An illustration of the position of paratope amino acid residues within the VH and VL domains is depicted in FIG. 2 and FIG. 3.

The amino acid residues identified to contribute to antigen binding are identified in Table 24 (for the variable heavy chain domain amino acid residues) and Table 25 (for the variable light chain domain amino acid residues). Amino acid positions are numbered according to the Kabat numbering system (the same numbering is used in FIGS. 2 and 3). Amino acids positions involved in antigen binding are identified by their Kabat position in the VH or VL domain (see also the numbering in FIGS. 2 and 3).

TABLE 24

Variable heavy chain amino acid residues involved in antigen binding as identified by crystal structure analysis of P1AD9820

| VH | VEGF-A | ANG2 |
|---|---|---|
| FR1 | — | H3, D26, F27, E29, Y30 |
| H-CDR1 | D35c | D35b |
| FR2 | — | — |
| H-CDR2 | D55, H56, K57, Y58, T61, K62, F63, I64, G65 | — |
| FR3 | R66 | R94 |
| H-CDR3 | D95 | V96, F98, F99 |
| FR4 | — | — |

TABLE 25

Variable light chain amino acid residues involved in antigen binding as identified by crystal structure analysis of P1AD9820

| VL | VEGF-A | ANG2 |
|---|---|---|
| FR1 | I2, Y3 | — |
| L-CDR1 | Y27, W27a, E32 | E32, |
| FR2 | — | L46, F49 |
| L-CDR2 | — | D50, F53, K54, V55, Y56 |
| FR3 | — | E57 |
| L-CDR3 | R92, Y93, H94, P95 | Y91 |
| FR4 | — | — |

The invention claimed is:

1. An antibody or antigen binding fragment thereof that binds to human vascular endothelial growth factor A (VEGF-A) and to human angiopoietin-2 (ANG2), comprising a VH amino acid sequence of SEQ ID NO:19 and a VL amino acid sequence of SEQ ID NO:20.

2. An antibody or antigen-binding fragment thereof that binds to human VEGF-A and to human ANG2 having a heavy chain that comprises the amino acid sequence of SEQ ID NO: 24 and having a light chain that comprises the amino acid sequence of SEQ ID NO: 25.

3. The antibody or antigen binding fragment of claim 1 or 2, which is an Fab fragment.

4. A pharmaceutical formulation comprising the antibody or antigen binding fragment of claim 3 and a pharmaceutically acceptable carrier.

5. A pre-filled syringe containing the pharmaceutical formulation of claim 4.

6. An implantable port delivery device comprising a refillable reservoir containing the antibody or antigen-binding fragment of claim 3.

7. A pharmaceutical formulation comprising the antibody or antigen binding fragment of claim 1 or 2 and a pharmaceutically acceptable carrier.

8. A pre-filled syringe containing the pharmaceutical formulation of claim 7.

9. An implantable port delivery device comprising a refillable reservoir containing the antibody or antigen-binding fragment of claim 1 or 2.

* * * * *